United States Patent
Higuchi et al.

(10) Patent No.: US 9,956,201 B2
(45) Date of Patent: May 1, 2018

(54) COMPOSITIONS COMPRISING BIOREVERSIBLE DERIVATIVES OF HYDROXY N-SUBSTITUTED-2-AMINOTETRALINS, AND RELATED DOSAGE FORMS

(71) Applicant: Spriaso LLC, Salt Lake City, UT (US)

(72) Inventors: William I. Higuchi, Salt Lake City, UT (US); Firoozeh Aminian Patel, Salt Lake City, UT (US)

(73) Assignee: SPRIASO LLC, Salt Lake City, UT (US)

( * ) Notice: Subject to any disclaimer, the term of this patent is extended or adjusted under 35 U.S.C. 154(b) by 118 days.

(21) Appl. No.: 14/337,037

(22) Filed: Jul. 21, 2014

(65) Prior Publication Data
US 2016/0015684 A1    Jan. 21, 2016

(51) Int. Cl.
*A61K 31/381* (2006.01)
*A61K 31/135* (2006.01)
*A61K 45/06* (2006.01)
*C07D 333/20* (2006.01)
*A61K 31/245* (2006.01)
*A61K 31/24* (2006.01)
*C07C 215/64* (2006.01)
*C07C 219/26* (2006.01)

(52) U.S. Cl.
CPC .......... *A61K 31/381* (2013.01); *A61K 31/135* (2013.01); *A61K 31/24* (2013.01); *A61K 31/245* (2013.01); *A61K 45/06* (2013.01); *C07D 333/20* (2013.01); *C07C 215/64* (2013.01); *C07C 219/26* (2013.01); *C07C 2101/08* (2013.01); *C07C 2101/14* (2013.01)

(58) Field of Classification Search
CPC .... A61K 31/381; A61K 31/135; A61K 45/06; A61K 31/245; A61K 31/24; C07D 333/20; C07C 215/64; C07C 219/26; C07C 2101/08; C07C 2101/14
See application file for complete search history.

(56) References Cited

U.S. PATENT DOCUMENTS

| | | | |
|---|---|---|---|
| 5,442,117 A | 8/1995 | Stahly et al. | |
| 6,929,801 B2 | 8/2005 | Klose et al. | |
| 7,309,497 B2 | 12/2007 | Rimpler et al. | |
| 7,632,859 B2 | 12/2009 | Li et al. | |
| 7,683,040 B2 | 3/2010 | Krämer et al. | |
| 7,872,041 B2 | 1/2011 | Scheller | |
| 8,246,979 B2 | 8/2012 | Schacht et al. | |
| 8,283,376 B2 | 10/2012 | Scheller et al. | |
| 8,604,076 B2 | 12/2013 | Rimpler et al. | |
| 8,609,641 B2 | 12/2013 | Scheller et al. | |
| 8,617,591 B2 | 12/2013 | Schacht et al. | |
| 8,647,314 B2 | 2/2014 | Asmussen et al. | |
| 2003/0180352 A1* | 9/2003 | Patel et al. ................. | 424/465 |
| 2007/0093546 A1 | 4/2007 | Scheller et al. | |
| 2008/0260846 A1 | 10/2008 | Zhang | |
| 2008/0274061 A1 | 11/2008 | Schollmayer et al. | |
| 2011/0104281 A1 | 5/2011 | Beyreuther et al. | |
| 2012/0148675 A1 | 6/2012 | Chickmath et al. | |

FOREIGN PATENT DOCUMENTS

WO    2005058296 A1    6/2005

OTHER PUBLICATIONS

Sozio et al (Expert Opin. Drug Discov. (2012) 7(5):385-406).*
Daas et al (Naunyn-Schmiedeberg's Arch Pharmacol (1990) 341:186-191).*
Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Internet Archive, accessed Jun. 23, 2016.
EMEA (http://www.ema.europa.eu/docs/en_GB/document_library/EPAR_-_Scientific_Discussion/human/000626/ WC500026394.pdf, accessed Jun. 23, 2016, published May 7, 2013).
Den Daas et al (Naunyn-Schmiedeberg's Arch Pharmacal (1990) 341 : 186-191).
Duty et al (British Journal of Pharmacology (2011) 164 1357-1391).
Boullata et al (Handbook of Drug-Nutrient Interactions, Mar. 17, 2010, Springer Science & Business Media).

* cited by examiner

Primary Examiner — Angela C Brown-Pettigrew
(74) Attorney, Agent, or Firm — TraskBritt, P.C.

(57) ABSTRACT

Described are compositions that may be orally administered that comprise a bioreversible derivative of hydroxy N-substituted-2-aminotetralin or an enantiomer or salt or prodrug thereof, and a pharmaceutically acceptable carrier suitable for oral administration in the amount present, wherein the composition is orally bioavailable when administered to a subject. The bioreversible derivative has an intrinsic lipophilicity C log P value of about 7 to about 11.5. A method comprises oral administering such composition to a human subject in need of hydroxy N-substituted-2-aminotetralin therapy.

22 Claims, No Drawings

COMPOSITIONS COMPRISING BIOREVERSIBLE DERIVATIVES OF HYDROXY N-SUBSTITUTED-2-AMINOTETRALINS, AND RELATED DOSAGE FORMS

TECHNICAL FIELD

The disclosure relates generally to pharmaceuticals and medicine.

BACKGROUND

Some of the hydroxy N-substituted-2-aminotetralins, such as (S)-6-[propyl(2-thiophen-2-ylethyl)amino]-5,6,7,8-tetrahydronaphthalen-1-ol (also known as rotigotine), 5-hydroxy-dipropylaminotetralin (5-OH-DPAT), 8-hydroxy-dipropylaminotetralin (8-OH-DPAT), and 7-hydroxy-dipropylaminotetralin (7-OH-DPAT), exhibit agonist-like activity through, among other receptors, dopamine and serotonin receptors distributed in various body tissues and address various diseases, particularly central nervous system (CNS) disorders. However, these compounds are prone to poor absorption and significant pre-systemic inactivation limiting their oral utility.

Dopamine is an essential neurotransmitter of the central nervous system. The activity of dopamine is mediated via binding to multiple different dopamine receptors. These receptors can be sorted by their morphology and their manner of signal transduction into classes "D1-like" (D1 and D5) as well as "D2-like" (D2, D3 and D4 receptors). The D3 receptor was first cloned by Sokoloff (*Nature* 347, 1990, 146) and is especially expressed in the limbic system, in which emotional and cognitive processes are controlled. It is also expressed although somewhat less pronounced in the striatal motor tissue where it serves the purpose of fine regulation of movement processes (Joyce, *Pharmacol. Ther* 90, 2001, 231-259). Recently, the D3 receptor has been considered a promising target for the development of active agents for the treatment of different psychiatric and motor diseases.

The serotonin receptors, also known as 5-hydroxytryptamine receptors or 5-HT receptors, are a group of G protein-coupled receptors (GPCRs) and ligand-gated ion channels (LGICs) found in the central and peripheral nervous systems. They mediate both excitatory and inhibitory neurotransmission. The serotonin receptors are activated by the neurotransmitter serotonin, which acts as their natural ligand. The serotonin receptors modulate the release of many neurotransmitters, including glutamate, gamma amino butyric acid (GABA), dopamine, epinephrine/norepinephrine, and acetylcholine, as well as many hormones, including oxytocin, prolactin, vasopressin, cortisol, corticotropin, and substance P, among others. The serotonin receptors influence various biological and neurological processes such as aggression, anxiety, appetite, cognition, learning, memory, mood, nausea, sleep, and thermoregulation. The serotonin receptors are the target of a variety of pharmaceuticals, including many antidepressants, antipsychotics, anorectics, antiemetics, gastroprokinetic agents, antimigraine agents, hallucinogens, and entactogens.

The 5-HT1A receptor is a subtype of 5-HT receptor that binds the endogenous neurotransmitter serotonin. The 5-HT1A receptor is the most widespread of all the 5-HT receptors. In the central nervous system, 5-HT1A receptors exist in the cerebral cortex, hippocampus, septum, amygdala, and raphe nucleus in high densities. Low amounts also exist in the basal ganglia and thalamus. The 5-HT1A receptor is thought to be involved in neuro-modulation.

The 5-HT7 receptor is a member of the GPCR superfamily of cell surface receptors and is activated by the neurotransmitter serotonin (5-hydroxytryptamine, 5-HT). The 5-HT7 receptor is expressed in a variety of human tissues, particularly in the brain, the gastrointestinal tract, and in various blood vessels. The 5-HT7 receptor plays a role in smooth muscle relaxation within the vasculature and in the gastrointestinal tract. The highest 5-HT7 receptor densities are in the thalamus and hypothalamus, and it is present at higher densities also in the hippocampus and cortex. The 5-HT7 receptor is involved in thermoregulation, circadian rhythm, learning and memory, and sleep. It is also speculated that this receptor may be involved in mood regulation, suggesting that it may be a useful target in the treatment of depression and this receptor gene is a candidate locus for involvement in autistic disorder and other neuropsychiatric disorders.

A dopamine agonist is a compound that activates dopamine receptors in the absence of dopamine. Dopamine agonists activate signaling pathways through the dopamine receptor and trimeric G-proteins, ultimately leading to changes in gene transcription. Dopamine agonists directly stimulate the receptors in nerves in the brain that normally would be stimulated by dopamine. Unlike levodopa, a dopamine agonist is not changed (converted) into dopamine when it enters the body, but it behaves like dopamine.

Parkinson's disease occurs as a result of a chronic, progressive degeneration of neurons, the cause of which has not yet been completely understood. It is clinically manifested in the form of the cardinal symptoms of resting tremors, rigidity, bradykinesia and postural instability.

Dopamine agonists may be used in the early stages of Parkinson's disease to reduce symptoms. This approach is often effective in people who have been newly diagnosed with the disease (especially those younger than 60), because it can delay the need for levodopa and thus postpone the motor fluctuations that may occur with long-term levodopa therapy.

A dopamine agonist may be added to treatment with a dopaminergic agent such as levodopa in the later stages of Parkinson's disease when levodopa no longer is able to adequately control symptoms on its own, and increasing the dose to provide adequate control of symptoms would cause excessive side effects.

Typically, patients with Parkinson's disease only develop the motor disturbances once approximately 70% to 80% of the dopaminergic neurons in the substantia nigra (SN) have been irreversibly damaged. Generally, the therapy of Parkinson disease normally is initiated with the onset of symptoms such as bradykinesis, resting tremors, rigidity, postural instability, etc.; however, at this point in time the chances of a therapy with lasting effects are minimal. Therefore, it is desirable to commence therapy as early as possible for prophylactic or preventative purposes.

D3 agonists in particular have neuroprotective potential for the treatment and prophylaxis of neurodegenerative disorders (Pulvirenti et al., Trends Pharmacol. Sci. 23, 2002, 151-153; Joyce, Pharmacol. Ther. 90, 2001, 231-259; EP Patent No. 0 988 296; PCT Patent Application Publication Nos. WO 2003/029233 and WO 1993/023035).

D3 agonists could also represent valuable therapeutics for the treatment or prophylaxis of different types of depression, in particular endogenous monophasic depression ("major depression"), pain, anxiety disorders, sexual dysfunctions, especially male erectile dysfunction or female sexual disorder or SSRI induced sexual dysfunction, glaucoma, cognitive disorders, restless leg syndrome, especially moderate to severe restless leg syndrome, restless limb disorder, neurodevelopmental type disorder, attention deficit hyperactivity syndrome (ADHS) or attention deficit hyperactivity disorder (ADHD), hyperkinetic disorder, obsessive compulsive disorder, impulsive disorder, hyperprolactinemia, hyperprolactinoma, eating disorders, neurogenerative disorder, Parkinson-associated movement disorders, dopa and neuroleptic induced/sensitive movement disorders, e.g., akathisia, rigor, dystonia and dyskinesia, as well as cocaine, alcohol, opiate and nicotine addiction, galactorrhea, ovarian hyperstimulation disorder, acromegaly and Parkinson-associated movement disorders, e.g., rigor, dystonia and dyskinesia; L-dopa-induced disorders, idiopathic dystonia, in particular Segawa syndrome, neuroleptic-induced (tardive) dyskinesia, dystonia and akathisia, as well as Parkinson plus syndrome.

2-aminotetratlin derivatives are compounds that are similar in structure to dopamine, likely underlying their pharmacology. Class of compounds with a high affinity for, e.g., D2 "like" and 5HT1A and 5HT7 receptors are the hydroxy N-substituted-2-aminotetralins, e.g. 5-OH-DPAT, (S)-6-[propyl(2-thiophen-2-ylethyl)amino]-5,6,7,8-tetrahydronaphthalen-1-ol (also known as rotigotine or N-0437, hereinafter "rotigotine"), 7-OH-DPAT, and 5,6-dihydroxy-DPAT. Due to amphipathic (having both acidic and basic functionalities) nature of these molecules they have potential to ionize at physiological pHs; therefore, these compounds are prone to issues related to their existence as highly charged species such as zwitterions and lack of sufficient unionized fraction at pHs encountered in the gastrointestinal tract when these compounds are given orally for absorption.

Preclinical data (Swart and Zeeuw, Pharmazie (1992), 47, 613-615) show that hydroxy N-substituted-2-aminotetralins, such as rotigotine, display zero to limited activity upon oral administration. A major disadvantage of the hydroxy N-substituted-2-aminotetralin is that they undergo considerable inactivation by glucuronidation in the gut and the liver, and have insignificant or inappreciable amounts of these compounds existing in the unionized form at pHs encountered in the gastrointestinal tract. One of the strategies to circumvent the problem of low oral bioavailability of the hydroxy N-substituted-2-aminotetralins is to search for suitable bioreversible derivatives.

For efficacy of one such hydroxy N-substituted-2-aminotetralin, rotigotine, maximum steady state levels, Css-max, greater than 0.1 ng/ml of rotigotine, are desired for effective therapy. Importantly, however, to date the oral effectiveness of rotigotine has been elusive, due to a distinct first-pass effect. The bioavailability of N-0923, an enantiomer of rotigotine, after oral administration when tested in animal model was merely about 0.5% (Swart and Zeeuw, Pharmazie (1992), 47, 613-615). Therefore, rotigotine has been previously administered to patients mainly by transdermal delivery methods (see, e.g., U.S. Pat. Nos. 8,617,591; 8,246,979; and 6,929,801; PCT Application Publication Nos. WO 1994/07468 and WO 1999/49852). Other non-oral approaches have also been reported for delivery of rotigotine, such as iontophoretic transdermal (U.S. Pat. No. 7,632,859), intranasal (U.S. Pat. No. 7,683,040), transmucosal (U.S. Application Publication No. 2008/0274061), gingival (U.S. Pat. No. 8,647,314), sublingual, and injectable (U.S. Pat. Nos. 7,309,497 and 8,604,076).

A viable oral dosage form with adequate bioavailability of rotigotine would be desirable for necessary therapeutic applications of such an agent and is expected to be more patient friendly than non-oral forms.

Prodrug or a bioreversible derivatization approach to improve oral bioavailability of drugs prone to first pass inactivation has been reported. (Stella V. J., Charman, W. N. A. and Naringrekar V. H.; Drugs (1985), 29, 455-473). Rodenhuis et. al. (Chapter 6, Neuropharmacological Evaluation of a New Dopaminergic Prodrug with Anti-Parkinsonian Potential, 97-106, 2000—in preparation) have reported data on bioactivity in an animal model of a pharmacophore equivalent, a di-hydro derivative of analogue of 5-OH DPAT, in an attempt to provide oral options for these agents. Specific approaches to improve oral bioactivity of rotigotine via carbamate [den Daas et. al, J. Pharm Pharmacol (1991), 43(1), 11-16] and ester [den Daas et. al., Naunyn Schmiedebergs, Arch Pharmacol (1990), 341(3), 186-191] prodrugs have been attempted in preclinical models; however, identification of specific bioreversible derivatives or compositions, or dosage forms or methods of achieving safe and effective levels of these agents after oral administration, especially rotigotine, in humans still remain an unmet need.

Moreover, the bioreversibility of any prodrug/derivative needs to be managed to get adequate and sustained levels of the drug derived from prodrug in vivo without adding any safety issues associated with the prodrug or its metabolite. Such safety issues will probably be related to the safety of the prodrug entity itself and its bioreversion rate to the parent drug in vivo. A rapid bioreversion rate may be desirable from a safety and efficacy standpoint, but too rapid bioreversion rate may allow the drug to become available in the absorption/distribution pathway too rapidly leading to substantial deactivation of the drug. Therefore, in addition to overcoming absorption challenges with bioreversible hydroxy N-substituted-2-aminotetralin derivative, an adequate bio-reversion rate into the parent drug remain an important design element in prodrug/bioreversible derivative design and is of particular challenge with hydroxy N-substituted-2-aminotetralin compounds due to their being a ready substrate for fast inactivation.

Approaches to date have failed to disclose any specific bioreversible derivative, its compositions, dosage forms and/or methods of use that would be particularly useful in overcoming poor aqueous intrinsic solubility and/or oral delivery/absorption challenges associated with such as bioreversible derivatives.

Therefore, attaining adequate oral bioavailability of hydroxy N-substituted-2-aminotetralins, such as rotigotine, remains a challenge and an unmet need for such compounds. No known approaches including a prodrug/bioreversible derivatives approach to date have been able to successfully deliver orally to attain therapeutically meaningful levels of these important agents.

Thus, there remains a need for an orally bioavailable composition and dosage form that enables safe and efficacious levels of hydroxy N-substituted-2-aminotetralin.

BRIEF SUMMARY

Disclosed are, among other things, pharmaceutical compositions and dosage forms suitable for oral delivery comprising bioreversible derivatives of hydroxy N-substituted-2-aminotetralins, such as rotigotine, and related methods.

In one embodiment, described is an oral pharmaceutical composition comprising: a bioreversible derivative of a compound of formula (I) or an enantiomer or salt or prodrug thereof,

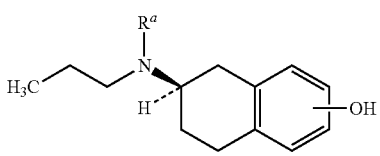

(I)

wherein $R^a$ is selected from the group consisting of H, 2-thiophen-2-ylethyl, and n-propyl; and a pharmaceutically acceptable carrier that may be administered orally in the amount present. The bioreversible derivative has an intrinsic lipophilicity C log P value of about 7 to about 11.5, and the composition is orally bioavailable when administered to a subject. In some embodiments, the bioreversible derivative has an intrinsic lipophilicity C log P value of about 8 to about 11. In further embodiments, the bioreversible derivative has an intrinsic lipophilicity C log P value of about 8.5 to about 10.5.

In some embodiments, the bioreversible derivative is a salt or a free base.

In some embodiments, the compound of formula (I) is selected from the group consisting of (S)-6-[propyl(2-thiophen-2-ylethyl)amino]-5,6,7,8-tetrahydronaphthalen-1-ol compound of formula, (6S)-(−)-5-hydroxy-N-propyl-2-aminotetralin, 8-hydroxy-N,N-dipropyl-2-aminotetralin, 5-hydroxy-N,N-dipropyl-2-aminotetralin, and 7-hydroxy-N,N-dipropyl-2-aminotetralin.

In some embodiments, the bioreversible derivative has the following structure:

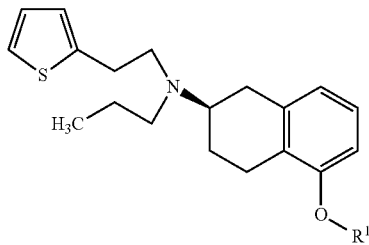

wherein $R^1$ is selected from the group consisting of alkyl, alkenyl, alkynyl, cycloalkyl, cycloalkenyl, cycloalkynyl, aryl, aralkyl, acyl, alkoxycarbonyl, cycloalkoxycarbonyl, aryloxycarbonyl, aralkoxycarbonyl, acetal, ketal, —C(O)NR$^2$R$^3$, —C(O)NHR$^2$, —S(O)$_2$R$^2$, —S(O)$_2$OR$^2$, —P(O$_2$H)OR$^2$; R$^2$ and R$^3$ are independently selected from the group consisting of H, $C_{1-16}$ alkyl or alkenyl or alkynyl, $C_{3-16}$ cycloalkyl or cycloalkenyl or cycloalkynyl, benzyl, and phenyl.

In some embodiments, the bioreversible derivative has the following structure:

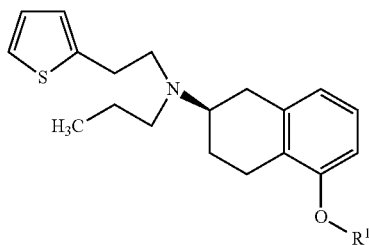

wherein $R^1$ is selected from the group of $C_{6-14}$ alkylcarbonyl, $C_{3-14}$ cycloalkylcarbonyl, benzoyl, —C(O)NR$^2$R$^3$, and —C(O)NHR$^2$, and R$^2$ and R$^3$ are independently selected from the group consisting of $C_{1-12}$ alkylcarbonyl, and $C_{3-12}$ cycloalkylcarbonyl.

The bioreversible derivative, when administered to a human body, is cleaved, processed or metabolized to compound of formula 1 such as (S)-6-[propyl(2-thiophen-2-ylethyl)amino]-5,6,7,8-tetrahydronaphthalen-1-ol, or a non-hydroxy prodrug or metabolite thereof.

The bioreversible derivative may comprise a moiety selected from the group consisting of a carbonyl, carbamate, carbonate, ketal, acetate, phosphate, phosphonate, sulfate, and sulfonate. The bioreversible derivative may be partially or fully solubilized in the composition.

The pharmaceutically acceptable carrier of the composition comprises at least one additive selected from the group consisting of lipophilic additives and hydrophilic additives. The solubility of the bioreversible derivative in a lipophilic additive is from about 5 mg/g to about 300 mg/g.

The lipophilic additive includes a constituent selected from the group consisting of lipophilic surfactant(s), triglyceride(s), oil(s), fatty acid(s), fatty acid glyceride(s), tocopherol(s), tocopherol derivative(s), and mixtures comprising any thereof. In some embodiments, the lipophilic additive comprises at least about 30% by weight of the carrier. The bioreversible derivative may not be fully dissolved in the lipophilic additive at 20° C.

In some embodiments, the lipophilic surfactant is selected from the group consisting of glyceryl monolinoleate, mono- and di glycerides of caprylic, capric acid, glyceryl monooleate, glyceryl palmitostearate, PEG-6 corn oil, PEG-6 almond oil, PEG-6 apricot kernel oil, lipophilic polyoxyethylene-polyoxypropylene block copolymers, propylene glycol mono-caprylate, sorbitan fatty acid esters, glyceryl palmitostearate, glyceryl stearate, glyceryl distearate, glyceryl monostearate, oleic acid, linoleic acid, phytosterols, phytosterol fatty acid esters, and mixtures thereof.

The hydrophilic additive includes a constituent selected from the group consisting of hydrophilic surfactant(s), hydrophilic triglyceride, cellulose(s), polyvinyl acetate, polyvinyl alcohol, polyvinylpyrrolidone, vinylpyrrolidone-vinyl acetate copolymer, polyethylene glycol, macrogol fatty acid ester, macrogol fatty acid ether, macrogol glycerol fatty acid ester, and combinations comprising any thereof.

In some embodiments, the hydrophilic surfactant is selected from the group consisting of PEG-8 caprylic/capric glycerides, lauroyl macrogol-32 glyceride, stearoyl macrogol glyceride, PEG-40 hydrogenated castor oil, PEG-35 castor oil, sodium lauryl sulfate, sodium dioctyl sulfosuccinate, polyethylene glycol fatty acids mono- and di-ester mixtures, polysorbate 80, polysorbate 20, polyethylene glycol 1000 tocopherol succinate, phytosterols, phytosterol fatty acid esters, and mixtures thereof.

The composition may further comprise at least one other active agent selected from the group consisting of an anticonvulsant, an opioid, a CGRP antagonist, a NMDA receptor blocker, a cannabinoid, a bradykinin antagonist, acetaminophen, dextromethorphan, a NSAID, a COX-2 selective inhibitor, a sedative, an antidepressant, a tranquilizer, a neuroprotective agent, an antipsychotic, an anxiolytic, an anti-migraine agent, and mixtures of any thereof.

The bioreversible derivative may be a crystalline solid, a non-crystalline solid, semi-solid, or liquid. When the bioreversible derivative is a crystalline solid, it may be a solvate, a polymorph, or a clathrate, etc. Additionally, the crystalline bioreversible derivative may be an anhydrate or a hydrate.

When the bioreversible derivative is a non-crystalline solid, it may be amorphous. The solid bioreversible derivative may be milled, micronized, nanosized or used as is.

In some embodiments, the composition may be a liquid, solution, solid solution, suspension, semi-solid, paste, jelly, powder, granule, emulsion, dispersion, or aggregate.

Also disclosed is an oral unit dosage form for a human subject in need of (S)-6-[propyl(2-thiophen-2-ylethyl)amino]-5,6,7,8-tetrahydronaphthalen-1-ol or (6 S)-(−)-5-hydroxy-N-propyl-2-aminotetralin. The oral unit dosage form comprises a 5-hydroxy bioreversible derivative of (S)-6-[propyl(2-thiophen-2-ylethyl)amino]-5,6,7,8-tetrahydronaphthalen-1-ol, or an enantiomer or salt or prodrug thereof; and a pharmaceutically acceptable carrier comprising at least one additive selected from the group consisting of lipophilic additives and hydrophilic additives. The oral unit dosage form provides a daily dose of the (S)-6-[propyl(2-thiophen-2-ylethyl)amino]-5,6,7,8-tetrahydronaphthalen-1-ol, or the prodrug or salt or enantiomer thereof, of about 0.5 mg to about 400 mg of the (S)-6-[propyl(2-thiophen-2-ylethyl)amino]-5,6,7,8-tetrahydronaphthalen-1-ol equivalent, based on single unit or multiple unit oral dosing.

The dosage form may be, for example, a capsule, matrix tablet, layered tablet, coated tablet, or osmotic pump tablet.

In some embodiments, the oral unit dosage form provides a daily dose of the (S)-6-[propyl(2-thiophen-2-ylethyl)amino]-5,6,7,8-tetrahydronaphthalen-1-ol, or the prodrug or salt or enantiomer thereof; of about 1 mg to about 250 mg of the (S)-6-[propyl(2-thiophen-2-ylethyl)amino]-5,6,7,8-tetrahydronaphthalen-1-ol equivalent, based on single unit or multiple unit oral dosing.

In some embodiments, the oral unit dosage form provides a daily dose of the (S)-6-[propyl(2-thiophen-2-ylethyl)amino]-5,6,7,8-tetrahydronaphthalen-1-ol, or the prodrug or salt, ester, or enantiomer thereof, of about 10 mg to about 100 mg of the (S)-6-[propyl(2-thiophen-2-ylethyl)amino]-5,6,7,8-tetrahydronaphthalen-1-ol equivalent, based on single unit or multiple unit oral dosing.

In some embodiments, the oral unit dosage form provides a mean Cmax value in a subject orally administered such an oral dosage form of at least about 0.04 ng/ml after a single dose. In some embodiments, the an oral unit dosage form provides a mean Cmax value in a subject orally administered such an oral dosage form of no greater than about 6 ng/ml, after a single dose. In some embodiments, the oral unit dosage form provides a mean Cmax value in a subject orally administered such an oral dosage form of at least about 0.04 ng/ml, but not greater than about 6 ng/ml, after a single dose.

In some embodiments, the oral unit dosage form provides a ratio of mean maximum serum concentration of the hydroxy N-substituted aminotetralin to the hydroxy N-substituted aminotetralin equivalent dose, Cmax/mg, value in a subject orally administered such oral dosage form of about $1.0 \times 10^{-10}$ ml$^{-1}$ to about $12 \times 10^{-6}$ ml$^{-1}$. In further embodiments, the oral unit dosage form provides a ratio of mean maximum serum concentration of the hydroxy N-substituted aminotetralin to the hydroxy N-substituted aminotetralin equivalent dose, Cmax/mg, value in a subject orally administered such oral dosage form of about $2.0 \times 10^{-9}$ to about $6 \times 10^{-6}$ ml$^{-1}$.

In some embodiments, the oral unit dosage form provides a ratio of mean maximum steady state serum concentration of the hydroxy N-substituted aminotetralin to the hydroxy N-substituted aminotetralin equivalent dose, Css-max/mg, value in a subject orally administered such an oral dosage form of at least about $2.5 \times 10^{-10}$ ml$^{-1}$. In some embodiments, the oral unit dosage form provides a ratio of mean maximum steady state serum concentration of the hydroxy N-substituted aminotetralin to the hydroxy N-substituted aminotetralin equivalent dose, Css-max/mg, value in a subject orally administered such an oral dosage form of no greater than about $20 \times 10^{-6}$ ml$^{-1}$. In some embodiments, the oral unit dosage form provides a ratio of mean maximum steady state serum concentration of the hydroxy N-substituted aminotetralin to the hydroxy N-substituted aminotetralin equivalent dose, Css-max/mg, value in a subject orally administered such an oral dosage form of about $2.5 \times 10^{-10}$ ml$^{-1}$ to about $20 \times 10^{-6}$ ml$^{-1}$.

In some embodiments, the oral unit dosage form provides a Cavg value in a subject orally administered such an oral dosage form of at least about 0.04 ng/ml. In some embodiments, the oral unit dosage form provides a Cavg value in a subject orally administered such an oral dosage form of no greater than about 4 ng/ml. In some embodiments, the oral unit dosage form provides a Cavg value in a subject orally administered such an oral dosage form of at least about 0.04 ng/ml, but not greater than about 4 ng/ml.

In further embodiments, the oral unit dosage form provides a Cavg value of no greater than about 3.0 ng/ml. In still further embodiments, the oral unit dosage form provides a Cavg value of no greater than about 2 ng/ml.

Also disclosed is a dosage form that may be orally administered to a mammal subject in need of (S)-6-[propyl(2-thiophen-2-ylethyl)amino]-5,6,7,8-tetrahydronaphthalen-1-ol therapy. The dosage form comprises a 5-hydroxy bioreversible derivative of (S)-6-[propyl(2-thiophen-2-ylethyl)amino]-5,6,7,8-tetrahydronaphthalen-1-ol, or an enantiomer or salt or prodrug thereof; and a pharmaceutically acceptable carrier. The dosage form provides a mean serum $AUC_{0-24}$ of (S)-6-[propyl(2-thiophen-2-ylethyl)amino]-5,6,7,8-tetrahydronaphthalen-1-ol of at least about 0.5 ng·hr·ml$^{-1}$ after a single dose oral administration of a therapeutically effective amount to the mammal subject when administered with a meal to the subject. In one particular embodiment, the dosage form is orally administered to the mammal subject with a meal that comprises at least about 15 g of fat.

In some embodiments, the dosage form provides a mean serum (S)-6-[propyl(2-thiophen-2-ylethyl)amino]-5,6,7,8-tetrahydronaphthalen-1-ol $AUC_{0-24}$ per mg of the bioreversible 5-hydroxy derivative equivalent administered of about $2.5 \times 10^{-10}$ hr·ml$^{-1}$ to about $10 \times 10^{6}$ hr·ml$^{-1}$. In further embodiments, the dosage form provides a mean serum (S)-6-[propyl(2-thiophen-2-ylethyl)amino]-5,6,7,8-tetrahydronaphthalen-1-ol $AUC_{0-24}$ per mg of the bioreversible 5-hydroxy derivative equivalent administered of about $10 \times 10^{-9}$ hr·ml$^{-1}$ to about $1 \times 10^{-6}$ hr·ml$^{-1}$ In some embodiments, the dosage form provides a mean serum $AUC_{0-24}$ of (S)-6-[propyl(2-thiophen-2-ylethyl)amino]-5,6,7,8-tetrahydronaphthalen-1-ol of no greater than about 94 ng·hr·ml$^{-1}$, upon single dose oral administration to the mammal subject In some embodiments, the dosage form is administered as a TID, BID or a QD regimen. In some embodiments, the dosage form is a tablet, granule, film, capsule, sprinkle, drink, or a powder. The dosage form may further comprise any typical tablet, granule, film, capsule, sprinkle, or wafer additives known in the art. Such additives may be hydrophilic or lipophilic, and be a part of the carrier. Typical processing of such dosage form are known in the art.

In some embodiments, the dosage form comprises a salt of the bioreversible derivative of hydroxy N-substituted-2-aminotetralin. As a non-limiting example, the dosage form may comprise a hydrochloride salt of the bioreversible derivative of hydroxy N-substituted-2-aminotetralin. In some embodiments, the hydrochloride salt of the bioreversible derivative of hydroxy N-substituted-2-aminotetralin may be preferred. The salt of the bioreversible derivative of hydroxy N-substituted-2-aminotetralin may or may not be solubilized in the dosage form. By way of non-limiting examples, the dosage form may comprise a salt of the bioreversible derivative of hydroxy N-substituted-2-aminotetralin in a powder or granule form in a capsule, or in a typical tablet.

In some embodiments, the dosage form is a controlled release, delayed release, extended release, or immediate release. In one particular embodiment, the dose release is at least 60% in 2 hours in 8% triton aqueous dissolution media.

Also disclosed is a composition for administration to a human subject in need of hydroxy N-substituted-2-aminotetralin therapy. The composition comprises a bioreversible derivative of hydroxy N-substituted-2-aminotetralin, or an enantiomer, or salt or prodrug thereof; and a pharmaceutically acceptable carrier. The bioreversible derivative has an apparent lipophilicity log $D_{7.4}$ value at pH 7.4 of about 4 to about 9. Upon oral administration of the bioreversible derivative of the hydroxy N-substituted-2-aminotetralin to the human subject, at least about 1% of the hydroxy N-substituted-2-aminotetralin equivalent dose is bioavailable as hydroxy N-substituted-2-aminotetralin to the human subject.

In some embodiments, upon mixing the composition with a surfactant free aqueous phosphate buffer at pH 7.4, at least about 0.001% of the bioreversible derivative exists in unionized form in an aqueous mixture. In some embodiments, upon mixing the composition with a surfactant free aqueous phosphate buffer at pH 7.4, at least about 0.01% of the bioreversible derivative exists in unionized form in an aqueous mixture. In other embodiments, at least about 0.1% of the bioreversible derivative exists in unionized form in an aqueous mixture upon mixing the composition with an aqueous phosphate buffer at pH 7.4.

Additionally disclosed is a method of treating a human subject for at least one of the following symptoms: depression, pain, anxiety disorders, sexual dysfunctions, glaucoma, cognitive disorders, restless leg syndrome, restless limb disorder, neurodevelopmental type disorder, attention deficit hyperactivity syndrome (ADHS), attention deficit hyperactivity disorder (ADHD), hyperkinetic disorder, obsessive compulsive disorder, impulsive disorder, hyperprolactinemia, hyperprolactinoma, eating disorders, neurodegenerative disorder, Parkinson-associated movement disorders, dopa- and neuroleptic-induced/sensitive movement disorders, galactorrhea, ovarian hyperstimulation disorder, neuroleptic-induced (tardive) dyskinesia, dystonia, akathisia, Parkinson plus syndrome, and addiction to cocaine, alcohol, opiate or nicotine. The method comprises orally administering the disclosed composition or dosage form to the subject.

In some embodiments, the composition is administered with a meal. In further embodiments, the composition is administered with a meal that comprises at least about 15 g of fat.

In one particular embodiment, a method of treating a human subject for at least one syndrome selected from the group consisting of Parkinson's disease and restless leg syndrome is disclosed. The method may comprise orally administering the disclosed composition to the human subject.

DETAILED DESCRIPTIONS

Definitions

"Alkyl" may be either a branched or unbranched alkyl group which preferably has 1 to 14 C atoms. Alkyl groups may additionally be substituted with one or more substituents, for example, with halogen.

"Alkenyl" is a group containing at least one C=C double bond. Alkenyl may be either a branched or unbranched alkenyl group. Alkenyl groups may additionally be substituted with one or more substituents, for example, with halogen.

"Alkynyl" is a group containing at least one C≡C triple bond. Alkynyl may be either a branched or unbranched alkynyl group. Alkynyl groups may additionally be substituted with one or more substituents, for example, with halogen.

"Cycloalkyl" is an alkyl group, which may consist only of ring-forming carbon atoms or may optionally further carry branched carbon atoms. Cycloalkyl may include 3 to 14, C atoms, more preferred 3 to 12 C atoms.

Cycloalkenyl" is an alkenyl group, which may consist only of ring-forming carbon atoms or may optionally further carry branched carbon atoms.

Cycloalkynyl" is an alkynyl group, which may consist only of ring-forming carbon atoms or may optionally further carry branched carbon atoms.

"Alkoxy" is an —O-alkyl group, wherein alkyl is preferably selected from the above mentioned groups for "alkyl." Preferred as alkoxy is a $C_{1-14}$ alkoxy group, more preferred is a $C_{3-12}$ alkoxy group.

"Aryl" is preferably phenyl. Phenyl may be, where appropriate, additionally substituted in one or more positions, e.g., with alkoxy, alkyl, halogen or nitro.

"Aralkyl" is an -alkyl-aryl group, wherein alkyl and aryl are preferably selected from the above mentioned "alkyl" and "aryl" groups, respectively. "Aralkyl" is preferably benzyl.

"Acyl" encompasses in particular the groups —C(O)-alkyl ("alkylcarbonyl"), —C(O)-cycloalkyl ("cyclo alkyl carbonyl"), —C(O)-aryl ("arylcarbonyl") and —C(O)-alkyl-aryl ("aralkylcarbonyl"), wherein "alkyl," "cycloalkyl," "aryl" and "aralkyl" are preferably selected from the above-mentioned groups for "alkyl," "cycloalkyl," "aryl" and "aralkyl," whereby —C(O)$C_{3-14}$ alkyl and —C(O)-phenyl are most preferred. Acyl is, for example, acetyl, propionyl, butyryl or —C(O)-phenyl ("benzoyl").

"Alkoxycarbonyl" is a —C(O)—O-alkyl group, wherein "alkyl" is preferably selected from the aforementioned group "alkyl." Alkoxycarbonyl is preferably a $C_{3-14}$ alkoxycarbonyl group.

"Cycloalkoxycarbonyl" is a —C(O)—O-cycloalkyl group, wherein "cycloalkyl" is preferably selected from the aforementioned "cycloalkyl" groups.

"Aryloxycarbonyl" is a —C(O)—O-aryl group, wherein "aryl" is preferably selected from the aforementioned "aryl" groups.

"Aralkoxycarbonyl" is a —C(O)—O-aralkyl group, wherein "aralkyl" is preferably selected from the aforementioned "aralkyl" groups.

"Ketal" is in particular the group —CR'R"—O-alkyl or —CR'R"—O-aryl bound to the phenolic oxygen atom, wherein "alkyl" and "aryl" are preferably selected from the above-mentioned groups "alkyl" and "aryl" and wherein R' and R" independently represent alkyl or aryl groups. "Acetal" differs from "ketal" in that the substituent R' in acetal is a hydrogen.

As used herein, the term "bioreversible derivative of hydroxy N-substituted-2-aminotetralin" means and includes a compound that is a hydroxy derivative of hydroxy N-substituted-2-aminotetralin group or a non hydroxy bioreversible derivative of hydroxy N-substituted-2-aminotetralin that when in therapeutically effective amounts in the human body, particularly in plasma or during entry through the gastrointestinal tract, it is cleaved, processed or metabolized to hydroxy N-substituted-2-aminotetralin or its non hydroxy derivative As used herein, the term "non-hydroxy bioreversible derivative of hydroxy N-substituted-2-aminotetralin" means and includes a compound that is derivatized at moiety other than the hydroxy moiety of the hydroxy N-substituted-2-aminotetralin to impart desired physicochemical properties, such as lipophilicity, pKa, etc., and such compound is cleaved, processed, or metabolized in vivo to a non-hydroxy derivative of the hydroxy N-substituted-2-aminotetralin or a hydroxy N-substituted-2-aminotetralin.

As used herein, the term "treatment," when used in conjunction with the administration of pharmaceutical compositions and dosage forms containing bioreversible derivative of hydroxy N-substituted-2-aminotetralin, refers to the administration of the dosage forms (for, e.g., capsule or tablet or solution or suspension dosage form) and pharmaceutically acceptable compositions to subjects who are either asymptomatic or symptomatic. In other words, "treatment" may both be to reduce or eliminate symptoms associated with a condition present in a subject, or it may be prophylactic treatment, i.e., to prevent the occurrence of the symptoms in a subject. Such prophylactic treatment may also be referred to as prevention of the condition.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Furthermore, the term "dosage form" may include one or more formulation(s) or composition(s) provided in a format for administration to a subject. When any of the above terms is modified by the term "oral" such terms refer to compositions, formulations, or dosage forms formulated and intended that may be orally administered to subjects.

As used herein, the term "fatty acid" refers to unionized carboxylic acids with a long aliphatic tail (chain), either saturated or unsaturated, conjugated or non-conjugated, branched or unbranched, cyclic or straight chained unless otherwise specified, the term C6 to C18 fatty acid glycerides refers to a mixture glycerides of mono-, di-, esters of medium to long chain (C6 to C18) fatty acids.

As used herein, the term "solidifying agent" or "solidifying additive" are used interchangeably and refer to a pharmaceutically acceptable additive that is in a solid physical state at 20° C. Similarly, a "solid lipophilic additive" refers to a lipophilic compound or component that is in a solid physical state at 20° C. and/or renders the composition or dosage form non-liquid, such as solid or semi-solid.

As used herein, the terms "not solubilized," when used to describe the state of the bioreversible derivative of hydroxy N-substituted-2-aminotetralin in the carrier, additive composition and/or capsule fill, dosage form, refer to the presence of some non-liquid state, which is predominantly crystalline or non-crystalline bioreversible derivative of hydroxy N-substituted-2-aminotetralin.

As used herein, the term "soluble" is as a measure or characteristic of the prodrug (e.g., bioreversible derivative of hydroxy N-substituted-2-aminotetralin) with regards to its ability to dissolve in a given solvent. The solubility of a bioreversible derivative of hydroxy N-substituted-2-aminotetralin in a particular component of the composition, or in the compositions of the current disclosure refers to the amount of the bioreversible derivative of hydroxy N-substituted-2-aminotetralin dissolved to form a visibly clear solution at a specified temperature such as room temperature or about 25° C. or about 37° C.

As used herein, the term "lipophilic," refers to compounds that are not freely soluble in water or freely soluble in lipids; and the term "lipophilic surfactant" refers to surfactants that have HLB values of about 10 or less. Conversely, the term "hydrophilic" refers to compounds that are freely soluble in water; and the term "hydrophilic surfactant" refers to surfactants that have HLB values of more than about 10.

As used herein, the term "capsule fill" refers to the composition disposed in a capsule dosage form.

As used herein, "subject" refers to a mammal that may benefit from the administration of a drug composition or method of this disclosure. Examples of a subject include a human in need of hydroxy N-substituted-2-aminotetralin.

The term "oral administration" represents any method of administration in which an active agent can be administered by swallowing, chewing, or sucking of the dosage form. The composition of the current disclosures may be admixed with food or drink prior to being orally consumed.

As used herein, a "dosing regimen" or "regimen" such as an "initial dosing regimen" or "starting dose" or a "maintenance dosing regimen" refers to how, when, how much, and for how long a dose of the compositions of the disclosure can be administered to a subject. For example, an initial or starting dose regimen for a subject may provide for a total daily dose of up to 400 mg administered as one dose or in 2-3 divided doses at least 8 hours apart with meals having from about 15 g to about 55 g of fat content, or fasted, or independent of meal or independent of meal content repeated daily for multiple days.

As used herein, the term "daily dose" refers to the amount of prodrug agent (e.g., bioreversible derivative of hydroxy N-substituted-2-aminotetralin) administered to a subject over a 24 hour period of time as hydroxy N-substituted-2-aminotetralin equivalent. The daily dose may be administered one, two or more administrations during the 24 hour period. In one embodiment, the daily dose provides for two or three administrations in a 24 hour period. With this in mind, an "initial dose" or "initial daily dose" refers to a dose administered during the initial regimen or period of a dosing regimen. The daily dose may be adjusted up or down as need based on patient's blood levels of the active at steady state. For example, an initial daily dose may be from about 0.5 mg to about 100 mg daily, but may be adjusted up to four times in equal or unequal increments as needed.

As used herein, "non-liquid," when used to refer to the state of the disclosed composition, refers to the physical state of the disclosed composition as being a gel, semi-solid or solid.

As used herein, the term "solid" and "semi-solid" refer to the physical state of a composition that supports its own weight at standard temperature and pressure, and has adequate viscosity or structure to not freely flow. Semi-solid materials may conform to the shape of a container under applied pressure.

As used herein, the term "steady state" refers to the achievement of stable serum total hydroxy N-substituted-2-aminotetralin levels upon a continuous dosing regimen (e.g., once daily, twice daily, thrice daily, etc.) of the administered bioreversible derivative hydroxy N-substituted-2-aminotetralin at a given dose, after at least 3 consecutive days.

Similarly, as used herein, the "steady state" serum concentration of a drug or chemical in a body fluid—usually plasma—at the time a "steady state" has been achieved, and rates of drug administration and drug elimination are equal. Css is a value approached as a limit and is achieved, theoretically, following the last of an infinite number of equal doses given at equal intervals. The maximum value under such conditions (Css-max) or "mean maximum steady state serum concentration (mean Css-max)" of hydroxy N-substituted-2-aminotetralin refers to the achievement of a stable serum total hydroxy N-substituted-2-aminotetralin concentration in a subject or group of subjects, respectively, in response to a continuous dosing regimen (e.g., once daily, twice or thrice daily, etc.) of the administered bioreversible derivative of hydroxy N-substituted-2-aminotetralin at a given dose as hydroxy N-substituted-2-aminotetralin equivalent, after at least 3 days, following the start of the dosing regimen.

As used herein, the terms "release" and "release rate" are used interchangeably to refer to the discharge or liberation of a substance, including without limitation a drug, from the dosage form into a surrounding environment such as an aqueous medium either in vitro or in vivo.

As used herein, an "effective amount" or a "therapeutically effective amount" of a drug refers to a sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, e.g., MEINER AND TONASCIA, *Clinical Trials: Design, Conduct, and Analysis*, Monographs in Epidemiology and Biostatistics, Vol. 8 (1986), incorporated herein by reference.

As used herein, the term "delayed release" refers to the release of the bioreversible derivative of hydroxy N-substituted-2-aminotetralin into an aqueous solution from the composition or oral dosage form in a time delayed manner attributed either to the inherent nature of the composition or to a coating, which may surround the composition or the oral dosage form. A traditional gelatin or non-gelatin non-enteric capsule shell does not alone constitute a delayed release mechanism.

The term "controlled release" in one embodiment, refers to a release such that at least about 60% of the bioreversible derivative of hydroxy N-substituted-2-aminotetralin is released within the first 60 minutes after the composition is contacted by the aqueous solution such as SIF or surfactant containing media such as 8% triton solution. The term. "immediate release" in one embodiment, refers to a release such that at least about 95% of the bioreversible derivative of hydroxy N-substituted-2-aminotetralin is released within the first 60 minutes after the composition is contacted by the aqueous solution such as SIF or surfactant containing media such as 8% Triton solution.

The terms "serum hydroxy N-substituted-2-aminotetralins levels," "serum bioreversible derivative of hydroxy N-substituted-2-aminotetralin concentration," "plasma hydroxy N-substituted-2-aminotetralin concentration," "bioreversible derivative hydroxy N-substituted-2-aminotetralin concentration in the blood," and "serum hydroxy N-substituted-2-aminotetralin concentration," are used interchangeably and refer to the "total" hydroxy N-substituted-2-aminotetralin concentration, which is the sum of the hydroxy N-substituted-2-aminotetralin including free and bound hydroxy N-substituted-2-aminotetralin concentrations.

As used herein, the average serum hydroxy N-substituted-2-aminotetralin concentration may be determined using methods and practices known in the art. Further, the plasma hydroxy N-substituted-2-aminotetralins concentration may be the determined by standard analytical procedures and methods available in the art, such as, for example, automated or manual immunoassay methods, liquid chromatography or liquid chromatography-tandem mass spectrometry (LC-MS/MS or GC/MS or ultra HPLC with electrochemical detection), etc.

As used herein, the term "AUCt1-t2" is the area under the curve of a plasma-versus-time graph determined for the analyte from the time "t1 to time t2." Wherein t1 and t2 are times (in hours) post dosing. For Example, t1 could be 0 hour (just immediately prior to administration) and t2 could be 2 hours.

As used herein, the term "Cavg," "Cave," or "C-average" are used interchangeably, and is determined as the mean AUC t1-t2 divided by the time period (|t1−t2|). For example, Cavg t0-t8 is the average plasma concentration over a period of 8 hours from t1=0 to t2=8 hours) post-dosing determined by dividing the AUC t0-t8 value by 8. Similarly, Cavg t0-t24 is the average plasma concentration over a period of 24 hours post-dosing determined by dividing the AUC t0-t24 value by 24 (t1=0-t2=24), and so on. Unless otherwise stated, all Cavg values are considered to be Cavg t0-t24 and unless otherwise stated, all the time values are expressed in hours (h). For example, the term Cavg t0-t24 denotes Cavg from time zero (0) to 24 hours post dosing.

As used herein, "Ct" refers to the serum concentration of hydroxy N-substituted-2-aminotetralin at time "t" prior to or after administration of the dosage of the current disclosure. The time "t" is generally in hours, unless otherwise specified. For example, a Ct of "C(−2 to 0)" refers to serum hydroxy N-substituted-2-aminotetralin concentration measured in sample collected between the time of about 2 hours before and just immediately prior to dosage administration to the subject tested. Similarly, Ct of "C (2 to 4)" refers to serum hydroxy N-substituted-2-aminotetralin concentration measured in sample collected between the time of about 2 hours and 4 hours after administration of a dosage to the subject tested.

As used herein "SIF" or "simulated intestinal fluid" refers to "intestinal fluid, simulated TS" in accordance with the USP. In one embodiment, the SIF does not contain pancreatic enzyme. In another embodiment, SIF may be a fed or fasted simulated intestinal aqueous solution comprising phosphatidyl choline and from about 2 mM to 20 mM bile salts.

As used herein "SGF" or "simulated gastric fluid" refers to "Gastric fluid, Simulated TS," in accordance with the USP. In one embodiment, the SGF does not contain the enzyme pepsin. In another embodiment, the SGF may also be a simple 0.1 N HCl solution in water. Alternatively, a surfactant containing aqueous dissolution media maybe used to monitor release of bioreversible derivative from the dosage form.

As used herein "single unit" when used to describe dosing of a subject refers to the dosage form being a single dosage form, e.g., a single tablet, capsule, etc. In contrast, "multiple unit" when used to describe dosing of a subject refers to the dosage including two or more dosage forms, e.g., 2 tablets, 3 capsules, etc. It is noteworthy that multiple unit dosage forms generally will be the same type of dosage forms (i.e., tablet or capsule) but are not required to be the same dosage form type.

As used herein, "free of" or "substantially free of" a particular compound or compositions refer to the absence of any separately added portion of the referenced compound or composition. Free of or substantially free of can include the presence of 5% weight or less (based on total composition weight) of the referenced compound, which may be present as a component or impurity of one or more of the ingredients.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Also described is a method for efficient and patient-friendly oral delivery to provide hydroxy N-substituted-2-aminotetralin in patients in need of such treatment. In particular, the compositions, dosage forms and related methods disclosed herein may provide serum rotigotine levels, Cavg, to effective therapeutic response of more than about 0.04 ng/ml in patient for longer periods of time post dosing in need thereof. Additionally, the compositions, dosage forms and related methods disclosed herein may offer the desirable results while providing patient-friendly regimens, such as, a practical rotigotine equivalent daily dose, less frequent administration in a day, and fewer number of dosage units per administration.

It is now found that only certain bioreversible derivative of hydroxy N-substituted-2-aminotetralins are suitable to provide safe and effective levels upon oral administration from a single administration through effective and pragmatic dosing regimens (dose, dosing frequency, dosage units) for utility in patients in need.

In one embodiment, an oral pharmaceutical compound comprises: a bioreversible derivative of a compound of formula (I) or an enantiomer or salt or prodrug thereof,

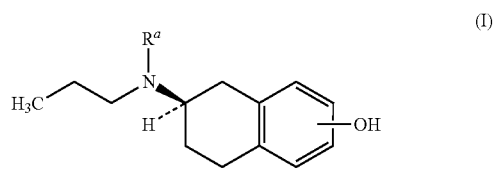

wherein $R^a$ is selected from the group consisting of H, 2-thiophen-2-ylethyl, and n-propyl; and a pharmaceutically acceptable carrier suitable that may be orally administered in the amount present, wherein the composition is orally bioavailable when administered to a subject. The bioreversible derivative has an intrinsic lipophilicity C log P value of about 7 to about 11.5.

The disclosed bioreversible derivatives of hydroxy N-substituted-2-aminotetralins may provide a corresponding hydroxy N-substituted-2-aminotetralins, or a prodrug or a metabolite thereof upon oral administration to a human body.

Non-limiting examples of the disclosed bioreversible derivatives may include, but are not limited to, a moiety selected from the group consisting of a carbonyl, carbamate, carbonate, ketal, acetate, phosphate, phosphonate, sulfate, and sulfonate.

The disclosed bioreversible derivatives of hydroxy N-substituted-2-aminotetralin may be prepared as described in the literatures. See, e.g., Hacksell et al., J. Med. Chem. (1979), 22, 1469; Sonesson, J. Med. Chem. (1995), 38, 1319; U.S. Pat. No. 5,442,117. The preparation of the disclosed bioreversible derivatives by reacting hydroxy N-substituted-2-aminotetralin with appropriate reactive precursors, such as acid chlorides, acid anhydrides, carbamoyl chlorides, sulfonyl chlorides, etc., is known to the skilled person in the field of biological chemistry. Examples for literature citations for the production of prodrugs are BUNDGAARD: Design of Prodrugs, Elsevier, Amsterdam (1985); Higuchi & Stella, *Prodrugs as Novel Drug Delivery Systems*, American Chemical Society, Washington D.C. (1975); SLOAN, Prodrugs—Topical and Ocular Drug Delivery, Ed: M. Dekker (1992); ROCHE, Design of biopharmaceutical properties through prodrugs and analogs, Washington D.C. (1977).

Ester is a reaction product of hydroxyl group (such as phenolic OH) and an inorganic or organic acid (such as carbonic acid, carboxylic acid, sulfuric acid, sulfonic acid or carbamic acid, phosphoric acid, phosphonic acid, boric acid, etc.) with elimination of water molecule. The carbonyl or sulfonyl acid may consist of a linear, branched, cyclic, saturated or unsaturated aliphatic group or substitutions thereof. Non-limiting examples of acids for esterification may include, but are not limited to, pidolic acid, nicotinic acid, pivalic acid, benzoic acid, anthranilic acid, naphthoic acid, naphthalene sulfonic acid, straight chain or cyclic carboxylic fatty acids, or C6-C18 fatty acids. The term "linear and branched C-1 to C-18 alkanoates" is denoted to mean aliphatic esters with chain lengths from 1 to 16 carbon atoms that are the aliphatic esters are made of 1 to 18 carbon atoms. Thus, in some embodiments of the disclosure, the bioreversible derivative is an ester wherein the ester group is a caproate, enanthate, a heptanoate (caprylate), a nanoate, a decanoate (caprate), an undecanoate, a dodecanoate (laurate), a tridecanoate, a tetradecanoate (myristate), a pentadecanoates, or a hexadecanoate (palmitate). Preferably, the ester group in the disclosed bioreversible derivatives replaces the hydroxy moiety of the hydroxy N-substituted-2-aminotetralin compounds.

The term "pharmaceutically acceptable salts" encompasses in particular non-toxic addition salts of bioreversible derivative of hydroxy N-substituted-2-aminotetralin with organic or inorganic acids as well as their hydrates and solvates. These acids may also suitable for esterification in preparation of bioreversible derivative ester. Non-limiting examples for inorganic acids may include, but are not limited to, HCl, HBr, sulfuric acid, sulfurous acid, phosphorous acid and phosphoric acid. Non-limiting examples for organic acids may include, but are not limited to, acetic acid, propionic acid, pyruvic acid, butyric acid, α-hydroxybutyric acid, β-hydroxybutyric acid, γ-hydroxybutyric acid, valeric acid, hydroxyvaleric acid, capronic acid, hydroxycapronic acid, caprylic acid, capric acid, lauric acid, myristic acid, palmitic acid, stearic acid, glycolic acid, lactic acid, D-glucuronic acid, L-glucuronic acid, D-galacturonic acid, glycine, benzoic acid, hydroxybenzoic acid, gallic acid, salicylic acid, vanillic acid, coumarinic acid, caffeic acid, hippuric acid, orotic acid, L-tartaric acid, D-tartaric acid, D,L-tartaric acid, meso-tartaric acid, fumaric acid, L-malic acid, D-malic acid, D,L-malic acid, oxalic acid, malonic acid, succinic acid, maleic acid, oxalic acetic acid, glutaric acid, hydroxyglutaric acid, ketoglutaric acid, adipinic acid, ketoadipinic acid, pimelic acid, glutamic acid, asparaginic acid, phthalic acid, propanetricarboxylic acid, citric acid, isocitric acid, methanesulfonic acid, toluene sulfonic acid, or trifluoromethanesulfonic acid.

Non-limiting examples of the disclosed bioreversible derivatives of hydroxy N-substituted-2-aminotetralins may include, but are not limited to, the bioreversible derivatives of hydroxy N-substituted-2-aminotetralin compounds (IA)-(IE) as shown below.

Compound (IA) is rotigotine.

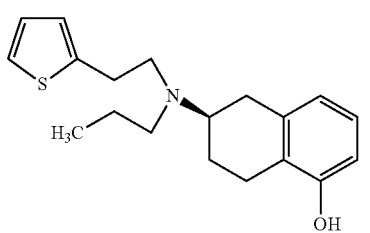

(IA)

Rotigotine is a D3 selective dopamine agonist. In particular, it behaves as a non-selective full agonist at most dopamine receptors and as an antagonist at the α2B-adrenergic receptor, and as a partial agonist at the 5-HT1A receptor. At clinical doses, rotigotine behaves mostly as a selective D2-like (D2, D3, and D4) and D5 receptor agonist. The exact mechanism of action of rotigotine has not been established, but it is thought to be related to its ability to stimulate dopamine receptors within the caudate-putamen in the brain.

Rotigotine has pKa values of about 7.9 and to about 10.3, and a calculated log P (C log P) of about 4 to about 4.9. Thus, rotigotine is expected to be present predominantly as charged species at physiological pH range and is most commonly used as its hydrochloride salt. Rotigotine is commercially available as a rotigotine transdermal system, but not as an oral delivery system. For example, NEUPRO® patch from UCB is a once-daily rotigotine transdermal system. Rotigotine is a dopamine agonist of the non-ergoline class of medications indicated for the treatment of Parkinson's disease (PD) and Willis-Ekbom Disease (WED), formerly known as restless legs syndrome (RLS) in Europe and the United States.

Rotigotine allows significant down titration of levodopa without severe adverse events. It is also known to inhibit prolactin secretion. Typical daily adult transdermal dose for the treatment of signs and symptoms of idiopathic Parkinson's disease (PD) is 2 mg (e.g. 2 mg recommended dose is achieved with a 4.5 mg strength per 10 cm² rotigotine patch releasing approximately 2 mg of rotigotine/24 hr) to 6 mg for Early-Stage PD, and 4 mg to 8 mg for Advanced-Stage PD. For the treatment of moderate to severe primary restless legs syndrome (RLS), typical daily adult transdermal dose is 1 mg to 3 mg. (Physician Desk Reference, prescribing information).

Use of rotigotine and its prodrugs for the treatment of depression have been disclosed in U.S. Patent Application Publication No. 2007/0093546; method for treating pain using hydroxy N-substituted-2-aminotetralin compound has been disclosed for treating pain (U.S. Patent Application Publication No. 2011/0104281); use of rotigotine and its prodrugs for treating and preventing Parkinson's plus syndrome (U.S. Pat. No. 7,872,041), and use of hydroxy N-substituted-2-aminotetralins for preventive treatment of Parkinson's disease (U.S. Pat. No. 8,283,376) has been disclosed. U.S. Pat. No. 8,609,641 and PCT Patent Application Publication No. WO 2005/058296 discloses utility of (6S)-(−)-5-hydroxy-N-propyl-2-aminotetralin, a metabolite of rotigotine, as a D3 agonist and its prodrugs for the treatment of dopamine sensitive treatment disorders. All of these patent documents are incorporated herein by this reference in their entirety.

In some embodiments, the disclosed bioreversible derivative of rotigotine may have the following chemical structure:

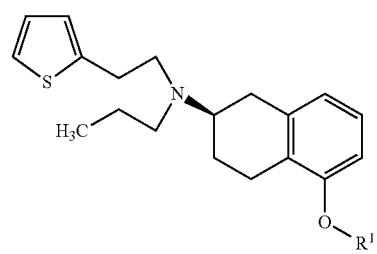

wherein $R^1$ is selected from the group consisting of alkyl, alkenyl, alkynyl, cycloalkynyl, cycloalkenyl, cycloalkyl, aryl, aralkyl, acyl, alkoxycarbonyl, cycloalkoxycarbonyl, aryloxycarbonyl, aralkoxycarbonyl, acetal, ketal, —C(O)NR²R³, —C(O)NHR², —S(O)₂R², —S(O)₂OR², —P(O₂H)OR²; and $R^2$ and $R^3$ are independently selected from the group consisting of H, $C_{1-16}$ alkyl, $C_{3-16}$ cycloalkyl, cycloalkenyl, cycloalkynyl, benzyl, and phenyl.

In some embodiments, the disclosed bioreversible derivative of rotigotine may have the following chemical structure

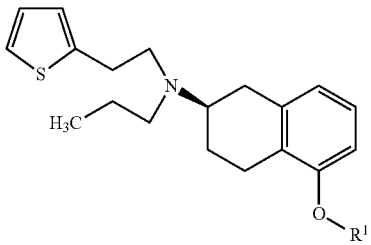

(IB)

wherein $R^1$ is selected from the group of $C_{6-14}$ alkylcarbonyl, $C_{3-14}$ cycloalkylcarbonyl, benzoyl, $C(O)NR^2R^3$, and —C(O)NHR², and $R^2$ and $R^3$ are independently selected from the group consisting of $C_{1-12}$ alkylcarbonyl, and $C_{3-12}$ cycloalkylcarbonyl.

Compound (IB) is (6S)-(−)-5-hydroxy-N-propyl-2-aminotetralin.

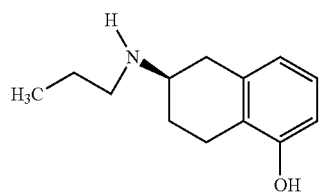

(IB)

(6S)-(−)-5-Hydroxy-N-propyl-2-aminotetralin is a metabolite of rotigotine. It is exhibits significant D3 selectivity with C log P of about 2.52±0.29 and pKa of about 10.6. Pure (S)-enantiomer of (6S)-(−)-5-hydroxy-N-propyl-2-aminotetralin has demonstrated a particular affinity to and functional selectivity for the D3 receptor as well as a pure agonistic activity, making the substance a valuable candidate for the treatment of diseases caused by dopamine deficiency.

Compound (IC) is 8-hydroxy-N,N-dipropyl-2-aminotetralin, also known as 8-OH-DPAT (hereinafter "8-OH-DPAT").

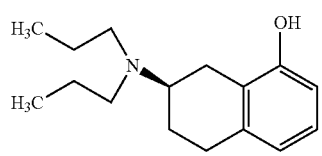

(IC)

8-OH-DPAT exhibits a mixed 5HT1A, 5HT7 receptor agonist, and as a serotonin reuptake inhibitor. 8-OH-DPAT has a C log P range of about 3.5 to 4.5, and pKa of about 10.54.

Compound (ID) is 5-hydroxy-N,N-dipropyl-2-aminotetralin, also known as 5-OH-DPAT (hereinafter "5-OH-DPAT").

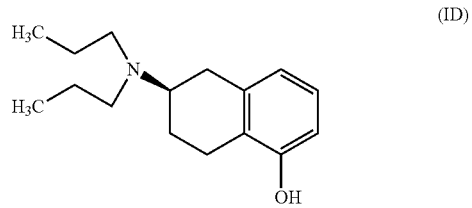 [SMILES: CCCN(CCC)[C@@H]1CCc2c(O)cccc2C1]

(ID)

The (S)-enantiomer of 5-OH-DPAT is active as an agonist acts as a dopamine receptor agonist with selectivity for the D2 receptor and D3 receptor subtypes D2/D3 receptor. 5-OH-DPAT has a C log P range of about 3.55 to about 4.3, and pKa of about 10.5.

Compound (IE) is 7-hydroxy-N,N-dipropyl-2-aminotetralin, also known as 7-OH-DPAT (hereinafter "7-OH-DPAT")

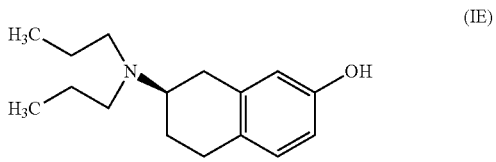 [SMILES: CCCN(CCC)[C@@H]1CCc2ccc(O)cc2C1]

(IE)

7-OH-DPAT acts as a dopamine receptor agonist with reasonable selectivity for the D3 receptor subtype. 7-OH-DPAT has a C log P range of from about 3.5 to about 4.5, and pKa of about 10.54.

Surprisingly, unlike any of the known bioreversible derivatives, the disclosed bioreversible derivatives of hydroxy N-substituted-2-aminotetralins possess certain desired physicochemical attributes, such as adequate lipid solubility, optimal lipophilicity, and appropriate ionization constants. Additionally, the disclosed oral compositions, dosage forms, and methods of oral administration allow for oral delivery of therapeutically meaningful levels of hydroxy N-substituted-2-aminotetralin drugs, thus making possible a more patient friendly approach in treating diseases.

The disclosed bioreversible derivatives of hydroxy N-substituted-2-aminotetralins are orally bioavailable when administered to a subject. Several characteristics of the bioreversible derivatives of hydroxy N-substituted-2-aminotetralins are required in order to achieve effective levels upon oral administration of the therapeutic amount of hydroxy N-substituted-2-aminotetralins in the subjects.

The log P value may be determined experimentally by measuring the partitioning of the species of interest between octanol and water or aqueous medium, and determining the amount of the species of interest in octanol and in the aqueous media, to provide a ratio of species concentration in octanol to aqueous media, which is known as partition efficiency. The intrinsic lipophilicity (P) or lipophilicity or partition efficiency is the preference of the uncharged species of interest for lipid or octanol over water. Log (logarithm to the base 10) of P (log P) is typically used to assess degree of lipophilicity or preference of the species of interest for lipid over water. Lipophilicity of the unionized species may be calculated, and designated as C log P based on its constituent as described below . . . .

In order to promote oral absorption and sustained levels, adequate lipophilicity of the drug is preferred. The lipophilicity of different bioreversible derivatives of hydroxy N-substituted-2-aminotetralin is expressed in terms of its octanol-water partition coefficient (log of partition efficiency) determined experimentally or calculated using a software program (C log P) with about ±0.5 units deviations noted in such calculations. For the straight chain esters of bioreversible derivative of hydroxy N-substituted-2-aminotetralin, the lipophilicity typically increases with the increasing carbon chain length of the ester moiety, as illustrated in the APPENDIX A-C and calculated using ACD/PHYSCHEM SUITE™, ACD/ChemSketch (FreeWare), version 12.00, Build 38526, Advanced Chemistry Development, Inc. (Toronto, Canada) on the Worldwide Web at acdlabs.com, 2010. It is understood that absolute and differential magnitude may vary depending on methodology, but trend is expected to be same. Additionally, it is not unusual for the experimental log P value and the C log P value to be non-identical sometimes by about 1 to 2 log units. It is understood that the C log P value is only a representative of the experimental log P value, and that the experimental log P value may be about 1 to 2 units above or below the C log P value due to the experimental deviation as needed or required for the performance of the compositions of the present disclosure.

The C log P values of rotigotine and (6S)-(−)-5-hydroxy-N-propyl-2-aminotetralin are about 4.96±0.35 and about 2.52±0.29, respectively. The C log P value of 5-OH-DPAT is about 3.55 to about 4.3, while the C log P value of 7-OH-DPAT and 8-OH-DPAT about 3.5 to about 4.5. It is now found that these hydroxy N-substituted-2-aminotetralins are inadequately lipophilic at physiological pHs (e.g., pH 7.4) to enable effective lipid/membrane/chylomicron partitioning. Additionally, these hydroxy N-substituted-2-aminotetralins are absorbed in the intestinal tract and prone to "first pass effect", rendering these compounds to be a substrate for hepatic inactivation.

In one particular embodiment, the bioreversible derivative of hydroxy N-substituted-2-aminotetralins of the disclosure has an intrinsic lipophilicity C log P value of about 7 to about 11.5.

In other embodiment, the disclosed bioreversible derivative has an intrinsic lipophilicity C log P value of about 8 to about 11. In further embodiment, the disclosed bioreversible derivative has an intrinsic lipophilicity C log P value of about 8.5 to about 10.5.

The log $D_{pH=7.4}$ value is a log of the distribution efficiency (ratio of concentrations of the disclosed bioreversible derivatives in octanol solvent to a pH 7.4 aqueous surfactant free buffer media).

In one particular embodiment, a composition for administration to a human subject in need of hydroxy N-substituted-2-aminotetralin therapy is disclosed, which composition is orally bioavailable in a mammalian subject. The composition comprises a bioreversible derivative of hydroxy N-substituted-2-aminotetralin, or an enantiomer, or salt or prodrug thereof; and a pharmaceutically acceptable carrier. The bioreversible derivative has an apparent lipophilicity log $D_{7.4}$ value at pH 7.4 of about 4 to about 9.

In some embodiments, the bioreversible derivative has an apparent lipophilicity log $D_{7.4}$ value at pH 7.4 of about 5 to about 8.5. In some further embodiments, the bioreversible derivative has an apparent lipophilicity log $D_{7.4}$ value at pH 7.4 of about 5.5 to about 8. In still some further embodiments, the bioreversible derivative has an apparent lipophilicity log $D_{7.4}$ value at pH 7.4 of about 5.5 to about 7.5.

The disclosed bioreversible derivatives of rotigotine may include from about 27 to about 35 carbon atoms, and from about 37 to about 51 hydrogen atoms.

The disclosed bioreversible derivatives of (6S)-(−)-5-hydroxy-N-propyl-2-aminotetralin may include from about 24 to about 31 carbon atoms, and from about 40 to about 51 hydrogen atoms.

The disclosed bioreversible derivatives of 8-OH-DPAT, 7-OH-DPAT, and 5-OH-DPAT, each may include from about 25 to about 31 carbon atoms, and from about 39 to about 50 hydrogen atoms.

It has been found that not all prodrugs (e.g., bioreversible derivative of hydroxy N-substituted-2-aminotetralin) that have a log P of more than about 5 and having an oil solubility of at least about 5 mg/mL are suitable for effective delivery of the ester derivatives for longer-lasting oral activity. The bioreversible derivative of hydroxy N-substituted-2-aminotetralin need not be fully dissolved in a mixture comprising one or more lipophilic additive and one or more hydrophilic additive in order to provide the desired bioavailability and PK parameters. Additionally, the bioreversible derivative of hydroxy N-substituted-2-aminotetralin may remain "not solubilized" at or above 30° C., in the components of the delivery system (e.g., lipophilic or hydrophilic additive, or carrier or their mixtures) that contribute, in part to solubilizing the bioreversible derivative.

In some embodiments, the disclosed bioreversible derivatives may have solubility in a lipophilic additive of from about 5 mg/g to about 300 mg/g. In some embodiments, the disclosed bioreversible derivatives may have solubility in a lipophilic additive of from about 10 mg/g to about 200 mg/g. In some embodiments, the disclosed bioreversible derivatives may have solubility in a lipophilic additive of from about 50 mg/g to about 150 mg/g, or of from about 75 mg/g to about 125 mg/g Additionally, it is now found that a solubility of the bioreversible derivatives of hydroxy N-substituted-2-aminotetralins in lipophilic additive, such as fatty acid or fatty acid glyceride (mono, di or triglyceride or mixtures thereof), of at least about 5 mg/g facilitates adequate partitioning into the formulation or physiologically generated chylomicron, thus enhancing their effective oral bioavailability. Thus, adequate solubility of the bioreversible derivatives of hydroxy N-substituted-2-aminotetralin in lipids (at least 5 mg/g) is desired for effective oral absorption. However, excessive lipid solubility in medium/long chain fatty acids and food glycerides (such as greater than 300 mg/g) may not cause sufficient de-partitioning of the bioreversible derivatives out of chylomicrons, and thus not be adequately bioavailable.

Furthermore, in one particular embodiment, under physiological pH (e.g. surfactant free aqueous buffer of pH of about 7.4), at least about 0.001% of the disclosed bioreversible derivatives of hydroxy N-substituted-2-aminotetralins may exist in unionized form in an aqueous mixture with surfactant free aqueous buffer of pH of about 7.4 to enable effective lipid/membrane/chylomicron partitioning.

In other embodiment, at least about 1% of the disclosed bioreversible derivatives may exist in unionized form under physiological pH (e.g. surfactant free aqueous buffer of pH of about 7.4). In still other embodiment, at least about 0.1% of the disclosed bioreversible derivatives may exist in unionized form under physiological pH in an aqueous mixture (e.g. surfactant free aqueous buffer of pH of about 7.4). In still further other embodiment, at least about 0.01% of the disclosed bioreversible derivatives may exist in unionized form under physiological pH in an aqueous mixture (e.g. surfactant free aqueous buffer of pH of about 7.4). In further embodiment, at least about 5% of the disclosed bioreversible derivatives may exist in unionized form under physiological pH in an aqueous mixture (e.g. surfactant free aqueous buffer of pH of about 7.4).

With this in mind, in one embodiment hereof, an oral pharmaceutical composition for administration to subjects in need of bioreversible derivative of hydroxy N-substituted-2-aminotetralin is provided. The composition comprises a bioreversible derivative of hydroxy N-substituted-2-aminotetralin and a pharmaceutically acceptable carrier.

Non-limiting examples of lipophilic additives can include lipophilic surfactants, triglycerides, oils, tocopherol, tocopherol derivatives and combinations thereof. In one embodiment, the lipophilic additive can include a fatty acid or fatty acid glyceride. In another embodiment, lipophilic additive can include the fatty acid glyceride, and the fatty acid glyceride can be a monoglyceride, a diglyceride, or mixtures thereof. Non-limiting examples of fatty acid glycerides that can be used in the oral pharmaceutical compositions and dosage forms of the disclosure include monoglycerides and/or diglycerides derived from sources such as maize oil, poppy seed oil, safflower oil, sunflower oil, borage seed oil, peppermint oil, coconut oil, palm kernel oil, castor oil, and mixtures thereof.

The pharmaceutically acceptable carrier suitable for the disclosure may include, but are not limited to, lipophilic additives, hydrophilic additives, or both.

In some embodiments, a pharmaceutically acceptable carrier may be any carrier suitable for delivering an efficacious amount of a bioreversible derivative of hydroxy N-substituted-2-aminotetralin, e.g., a rotigotine alkyl ester, to an individual. In some embodiments, the pharmaceutically acceptable carrier comprises a hydrophilic carrier (e.g., a hydrophilic surfactant or hydrophilic additive). In certain embodiments, the pharmaceutically acceptable carrier comprises a lipophilic carrier (e.g., a lipophilic surfactant or lipophilic additive). In some embodiments, the pharmaceutically acceptable carrier comprises a hydrophilic carrier (e.g., a hydrophilic surfactant or hydrophilic additive) and a lipophilic carrier (e.g., a lipophilic surfactant or lipophilic additive). In certain embodiments, the hydrophilic carrier comprises a hydrophilic triglyceride.

In specific embodiments, the hydrophilic triglyceride is a polyoxylated vegetable oil such as castor oil, corn oil, soyabean oil, coconut oil, palm kernel oil or a polyoxylated hydrogenated vegetable oil such as castor oil, corn oil, soyabean oil, coconut oil, palm kernel oil. In some embodiments, any pharmaceutical composition provided herein consists essentially of a lipophilic carrier or combination of lipophilic carriers. In some embodiments, the pharmaceutical composition comprises a carrier (e.g., a hydrophilic carrier and/or a lipophilic carrier), and the pharmaceutical composition is a solid, a semi-solid, a gel, a jelly, a paste, or the like. In certain embodiments, e.g., wherein a pharmaceutical composition comprising a hydrophilic carrier and/or a lipophilic carrier, a viscosity enhancing agent or a solidifying agent is utilized to afford a pharmaceutical composition that is a solid, a semi-solid, a gel, a jelly, a paste, or the like. Thus, in certain embodiments, a pharmaceutically acceptable carrier is a hydrophilic carrier (e.g., a hydrophilic surfactant or hydrophilic additive) and a viscosity enhancing or solidifying agent. In certain embodiments, the at least one pharmaceutically acceptable carrier is a lipophilic carrier (e.g., a lipophilic surfactant or lipophilic additive) and a viscosity enhancing or solidifying agent. In some embodiments, the at least one pharmaceutically acceptable carrier is or comprises a hydrophilic carrier (e.g., a hydrophilic surfactant or hydrophilic additive), a lipophilic carrier (e.g., a lipophilic surfactant or lipophilic additive), and a viscosity enhancing or solidifying agent. In some embodiments, the at least one pharmaceutically acceptable carrier is or comprises an amphiphilic or zwitterionic carrier (e.g., an amphiphilic surfactant or amphiphilic additive). In certain embodiments, the pharmaceutically acceptable carrier is any carrier suitable for achieving one or more of the pharmacokinetic and/or pharmacodynamic profiles set forth herein.

Additives useful herein include chemical substances that are generally pharmacologically inactive. Further, the additive may be solid, liquid or semi-solid in nature at about ambient room temperature. Furthermore, the additive may be hydrophilic or lipophilic. In certain instances, a "hydrophilic additive" is a substance that has at least one polar side group in its chemical structure which will attract water; whereas, a "lipophilic additive" exhibits a tendency to repel water.

In some embodiments, the hydrophilic or lipophilic additive is contained within the components forming a composition and/or pharmaceutical dosage form thereof. In certain embodiments, the hydrophilic or lipophilic additive is in an encapsulation coat in compositions. Alternatively, the additives can be comprised in the pharmaceutical composition but not as part of the composition itself. Specific, non-limiting examples of additives are described below.

Suitable additives include any additive that may facilitate the processes involving the preparation of a pharmaceutical composition and/or dosage form described herein. In some instances, such additives include those commonly utilized to facilitate the processes involving the preparation of a composition and/or a pharmaceutical dosage form described herein. These processes include agglomeration, air suspension chilling, air suspension drying, balling, coacervation, comminution, compression, pelletization, cryopelletization, encapsulation, extrusion, granulation, homogenization, inclusion complexation, lyophilization, nanoencapsulation, melting, mixing, molding, pan coating, solvent dehydration, sonication, spheronization, spray chilling, spray congealing, spray drying, or other processes known in the art. In certain instances, the additive is optionally pre-coated or encapsulated. Suitable additives are optionally utilized to influence the drug release from the composition and/or pharmaceutical dosage form.

Suitable additives utilized in various embodiments described herein include, by way of non-limiting example, adsorbing agents, anti-adherents, anticoagulants, antifoaming agents, antioxidants, anti-caking agents, anti-static agents, binders, bile acids, bufferants, bulking agents, chelating agents, coagulants, colorants, co-solvent, opaquants, congealing agents, coolants, cryoprotectants, diluents, dehumidifying agents, desiccants, desensitizers, disintegrants, dispersing agents, enzyme inhibitors, granulating agent, glidants, fillers, hydrating agent, super disintegrants, gums, mucilages, hydrogen bonding agents, enzymes, flavorants, humectants, humidifying agents, lubricant oils, ion-exchange resins, lubricants, plasticizers, pH modifying agents, preservatives, solidifying agent, solvents, solubilizers, spreading agent sweeteners, stabilizers, surface area enhancing agents, suspending agent, thickeners, viscosity increasing agents, waxes and mixtures thereof.

Some non-limiting examples of the additives suitable for the present disclosure may be: alcohols and/or polyols (e.g. ethanol, isopropanol, butanol, benzyl alcohol, ethylene glycol, propylene glycol, glycerol, sorbitol, mannitol, dimethyl isosorbide, polyethylene glycol, fatty acid alcohol, vinyl alcohol polypropylene glycol, polyvinylalcohol, tocopherols, cellulose cyclodextrins, other derivatives, forms, mixtures thereof, or the like); ethers of polyethylene glycols having an average molecular weight of about 200 to about 20,000 (e.g. tetrahydrofurfuryl alcohol PEG ether, methoxy PEG, or the like); amides (e.g. 2-pyrrolidone, 2-piperidone, 8-caprolactam, N-alkylpyrrolidone, N-hydroxyalkylpyrrolidone, N-alkylpiperidone, N-alkylcaprolactam, dimethylacetamide, polyvinylpyrrolidone and the like); esters (e.g. ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, 8-caprolactone and isomers thereof, 6-valerolactone and isomers thereof, β-butyrolactone and isomers thereof; and other additives known in the art, such as dimethyl acetamide, dimethyl isosorbide, N-methylpyrrolidones, monooctanoin, diethylene glycol monoethyl ether, or the like); amino acids (e.g. p-aminobenzamidine, sodium glycocholate) mesylate; amino acids and modified amino acids (e.g. aminoboronic acid derivatives and n-acetylcysteine; peptides and modified peptides (e.g. bacitracin, phosphinic acid dipeptide derivatives, pepstatin, antipain, leupeptin, chymostatin, elastin, bestatin, phoshporamindon, puromycin, cytochalasin potatocarboxy peptidase inhibitor, amastatin, or the like); polypeptide protease inhibitors; mucoadhesive polymers (e.g. polyacrylate derivatives, chitosan, cellulosics, chitosan-EDTA, chitosan-EDTA-antipain, polyacrylic acid, carboxymethyl cellulose etc.) or the like; or combinations thereof.

Some more examples of suitable additives for compositions and/or dosage forms described herein include, by way of non-limiting example, talc, magnesium stearate, silica (e.g. fumed silica, micronized silica, magnesium aluminum silicate etc.) and/or derivatives, polyethylene glycols, surfactants, waxes, oils, cetyl alcohol, polyvinyl alcohol, stearic acid, stearic acid salts, stearic acid derivatives, starch, hydrogenated vegetable oils, hydrogenated castor oils, sodium benzoate, sodium acetate, leucine, PEG, alkyl sulfate salts; acetylated monoglycerides; long-chain alcohols; silicone derivatives; butylated hydroxy toluene (BHT), butylated hydroxyl anisole (BHA), gallic acid, propyl gallate, ascorbic acid, ascorbyl palmitate, 4-hydroxymethyl-2,6-ditert-butyl phenol, dry starch, dry sugars, polyvinyl pyrrolidones, starch paste, methacrylic copolymers, bentonite, sucrose, polymeric cellulose derivatives, shellac, sugar syrup; corn syrup; polysaccharides, acacia, tragacanth, guar gum, xanthan gums; alginates; gelatin; gelatin hydrolysate; agar; sucrose; dextrose; PEG, vinyl pyrrolidone copolymers, poloxamers; pregelatinized starch, sorbitol, glucose); acetic acid, hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, vinegar, pharmaceutically acceptable bases, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanol amine, ethylenediamine, triethanolamine, triethylamine, triisopropanolamin; salt of a pharmaceutically acceptable cation and an anion; EDTA and EDTA salts; titanium dioxide, food dyes, lakes, natural vegetable colorants, iron oxides, silicates, sulfates, magnesium hydroxide and aluminum hydroxide; halogenated hydrocarbons, trichloroethane, trichloroethylene, dichloromethane, fluorotrichloromethane, diethylether, trehalose, phosphates, citric acid, tartaric acid, gelatin, dextran and mannitol, lactose, mannitol, sodium chloride, potassium chloride, spray-dried lactose, hydrolyzed starches, directly compressible starch, microcrystalline cellulose, cellulosic derivatives, sorbitol, sucrose, sucrose-based materials, calcium sulfate, dibasic calcium phosphate, dextrose, croscarmellose sodium, starch, starch derivatives, clays, gums, cellulose, cellulose derivatives, alginates, crosslinked polyvinylpyrrolidone, sodium starch glycolate and microcrystalline cellulose, magnesium oxide, magnesium carbonates; desensitizers, spray-dried flavors, essential oils, ethyl vanillin, styrene/divinyl benzene copolymers, quaternary ammonium compounds, polyethylene glycol, citrate esters (such as triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl sebacate, ascorbic acid, boric acid, sorbic acid, benzoic acid, and salts thereof, parabens, phenols, benzyl alcohol, and quaternary ammonium compounds; alcohols, ketones, esters, chlorinated hydrocarbons water; sweeteners, (e.g. maltose, sucrose, glucose, sorbitol, glycerin and dextrins, aspartame, saccharine, saccharine salts, glycyrrhizin), viscosity modifiers, sugars, polyvinylpyrrolidone, cellulosics, polymers, gums and/or alginates.

Additives may also be materials such as proteins (e.g., collagen, gelatin, Zein, gluten, mussel protein, lipoprotein); carbohydrates (e.g., alginates, carrageenan, cellulose derivatives, pectin, starch, chitosan); gums (e.g., xanthan gum, gum Arabic); spermaceti; natural or synthetic waxes; carnuaba wax; fatty acids (e.g., stearic acid, hydroxystearic acid); fatty alcohols; sugars; shellacs, such as those based on sugars (e.g., lactose, sucrose, dextrose) or starches; polysaccharide-based shellacs (e.g., maltodextrin and maltodextrin derivatives, dextrates, cyclodextrin and cyclodextrin derivatives); cellulosic-based polymers (e.g., ethyl cellulose, methyl cellulose, microcrystalline cellulose, sodium carboxymethyl cellulose, hydroxypropylmethyl cellulose, ethyl cellulose, hydroxypropyl cellulose, HPMC acid succinates, cellulose acetate, cellulose nitrate, cellulose acetate butyrate, cellulose acetate trimellitate, carboxymethylethyl cellulose, hydroxypropylmethyl cellulose phthalate), shellacs; inorganics, such as dicalcium phosphate, hydroxyapatite, tricalcium phosphate, talc and titania; polyols, such as mannitol, xylitol and sorbitol; polyethylene glycol esters; and polymers, such as alginates, poly(lactide coglycolide), gelatin, crosslinked gelatin, and agar-agar. Non-limiting examples of compounds that can be used as at least a part of the pharmaceutically acceptable carrier include without limitation celluloses; dextrins, gums, carbomers, methacrylates, sugars, lactoses, inorganic carbonates, oxides, chlorides, sulphates and the like; salts of calcium; salts of magnesium; salts of fatty acids; inorganic and organic acids, bases and salts; propylene glycol; glycerols; fatty acids; fatty alcohols; fatty acid esters; glycerol esters; mono-, di- or triglycerides; edible oils; omega oils; vegetable oils, hydrogenated vegetable oils; partially or fully hydrogenated vegetable oils; glycerol esters of fatty acids; waxes; alcohols; gelatin; polyethylene glycol; polyethylene oxide co-polymers; silicates; antioxidants, tocopherols, sugar stearates, starches, shellac, resins, proteins, acrylates; methyl copolymers; polyvinyl alcohol; starch; phthalates; and combinations thereof.

In one embodiment, the carrier may include at least one component selected from celluloses, dextrins, gums, carbomers, methacrylates, inorganic carbonates, salts of calcium, salts of magnesium, fatty acids, fatty acid esters, gelatin, lactoses, polyethylene glycol, polyethylene oxide co-polymers, silicates, partially hydrogenated vegetable oils, fully hydrogenated vegetable oils, waxes, antioxidants, tocopherol, sugar stearates, starches, shellac, resins, proteins, and combinations thereof.

In another embodiment, the carrier may include at least one component selected from celluloses, dextrins, gums, carbomers, methacrylates, sugars, lactoses, inorganic carbonates, salts of calcium, salts of magnesium, salts of fatty acids, inorganic and organic acids, bases and salts, propylene glycol, glycerols, fatty acids, fatty alcohols, fatty acid esters, glycerol esters, mono-glycerol esters of fatty acids, di-glycerol esters of fatty acids, mixtures of mono-glycerol and di-gylcerol esters of fatty acids, omega oils, waxes, alcohols, gelatin, polyethylene glycol, polyethylene oxide co-polymers, silicates, antioxidants, tocopherol, sugar stearates, starches, shellac, resins, proteins, acrylates, methyl copolymers, polyvinyl alcohol, starch, phthalates, and combinations thereof.

Non-limiting examples of additives as release modulators that may be used include lipophilic resins; ethyl cellulose (EC), methylethyl cellulose (MEC), carboxymethyl ethylcellulose (CMEC), hydroxyethyl cellulose (HEC), cellulose acetate (CA), cellulose propionate (CPr), cellulose butyrate (CB), cellulose acetate butyrate (CAB), cellulose acetate phthalate (CAP), cellulose acetate trimellitate (CAT), hydroxypropyl methyl cellulose phthalate (HPMCP), hydroxypropyl methyl cellulose acetate succinate (HPMCAS), hydroxypropyl methyl cellulose acetate trimellitate (HPMCAT), ion-exchange resin; poloxamers; and ethylhydroxy ethylcellulose (EHEC) tocopherol; shellac; and combinations thereof. Non-limiting examples of lipidic lipophilic release modulators include fatty acids; mono-, di-, tri-esters of fatty acids with glycerol; sucrose esters with fatty acids; cetyl alcohol; stearic acid; glyceryl monostearate; glyceryl distearate; glyceryl tristearate; glyceryl palmitostearate; hydrogenated castor oil; butyl and glycol esters of fatty acids; oleic acid; cetyl alcohol; stearyl alcohol; cetostearyl alcohol; hydrogenated vegetable oil; waxes; bees wax; lard; omega fatty acid esters; hydrogenated soybean oil; hydrogenated vegetable oil; hydrogenated cottonseed and castor oil; partially hydrogenated soybean oil; partially hydrogenated castor oil; partially soy and cottonseed oil; phospholipids; hydrogenated oils, and their derivatives and combinations thereof.

In another embodiment, the oral dosage form of this present disclosure may optionally include polyethylene glycol (PEG) having a molecular weight of about 400 to about 20,000, or mixtures of such polyethylene glycols. When included in an oral dosage faint, the amount of PEG may make up less than 30 wt % of the oral dosage form. In one embodiment, the amount of PEG can be about 5 wt % to about 30 wt %, about 5 wt % to about 25 wt %, about 5 wt % to about 20 wt %, about 5 wt % to about 15 wt %, or about 5 wt % to about 10 wt %. In a specific embodiment, the amount of PEG can make up about 10 wt % or less or about 5 wt % or less, of the oral dosage form.

Non-limiting examples of suspending agents or thickeners may include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and titanium dioxide. Non-limiting examples of anti-caking agents or fillers include silicon oxide and lactose. In the disclosed pharmaceutical compositions the carrier may be a solubilizer. Non-limiting examples of solubilizer may include organic co-solvents, such as ethanol, PEG 300, PEG 400, propylene glycol, glycerol, sorbitol, benzyl alcohol, benzyl benzoate, dimethyl acetamide, glycofurol, triacetin, or triethyl citrate.

It should be appreciated that there is considerable overlap between the above-listed additives/carriers in common usage, since a given hydrophilic or lipophilic additive is often classified differently by different practitioners in the field, or is commonly used for any of several different or overlapping functions. Thus, the above-listed hydrophilic or lipophilic additives should be taken as merely examples, and not limiting, of the types of additives that can be included in compositions of the present invention. In certain embodiments, the amounts of such additives are optionally adjusted and/or determined by one skilled in the art, according to the particular properties desired.

In certain embodiments, the pharmaceutically acceptable carrier comprises at least one hydrophilic carrier (e.g., hydrophilic surfactant). In some embodiments, the hydrophilic carrier is a polyoxylated glyceride (e.g., mono-, di-, or tri-glyceride), a polyoxylated vegetable oil, a polyoxylated hydrogenated vegetable oil, a polyoxylated fatty acid (mono-, or di-substituted), combinations thereof, or the like. In certain embodiments, the at least one pharmaceutically acceptable carrier comprises or further comprises a lipophilic carrier. Lipophilic carriers are selected from, by way of non-limiting example, a lipophilic surfactant, a vegetable oil (e.g., castor oil), a fatty acid, a fatty alcohol, a glyceride (e.g., mono-, di-, or tri-glyceride), a hydrogenated vegetable oil, a vitamin E compound (e.g., d,l-α-tocopherol), a triglyceride, a fatty acid, polyoxylated fatty acid, polyoxylated triglyceride, polyoxylated vegetable oil, or combinations thereof. In some embodiments, polyoxylated compounds include polyethoxylated compounds.

In certain embodiments, the at least one hydrophilic carriers make up about 1% to about 99% w/w, about 2% to about 80% w/w, about 2% to about 50% w/w, or about 10% to about 40% w/w of any pharmaceutical composition described herein. In some embodiments, lipophilic carriers make up about 1% w/w to about 99% w/w, about 2% to about 80% w/w, about 10% w/w to about 80% w/w, about 30% w/w, to about 80% w/w, or about 40% to about 80% w/w of any pharmaceutical composition described herein.

In specific embodiments, provided herein is a pharmaceutical composition comprising a hydrophilic carrier. In more specific embodiments, the hydrophilic carrier is or comprises a polyoxylated vegetable oil (e.g., a polyoxylated, hydrogenated vegetable oil). In still more specific embodiments, a polyoxylated vegetable oil is a polyoxylated castor oil (e.g., a polyoxylated, hydrogenated castor oil).

In certain specific embodiments provided herein is a pharmaceutical composition comprising an amphiphilic carrier. In more specific embodiments, the amphiphilic carrier is or comprises a zwitterionic choline (e.g., phosphatidylcholine).

The disclosed bioreversible derivatives of hydroxy N-substituted-2-aminotetralins may have solubility in a lipophilic additive of from about 5 mg/g to about 300 mg/g. Furthermore, the disclosed bioreversible derivatives of hydroxy N-substituted-2-aminotetralins may have solubility in a lipophilic additive of from about 20 mg/g to about 200 mg/g or of from about 50 mg/g to about 150 mg/g or of from about 75 mg/g to about 125 mg/g.

In some specific embodiments, provided herein is a pharmaceutical composition comprising a lipophilic carrier. In more specific embodiments, the lipophilic carrier is or comprises, by way of non-limiting example, a mono-, di- or triglyceride (e.g., glycerol monolinoleate), vitamin E compound.

In some embodiments, the at least one pharmaceutically acceptable carrier comprises at least one hydrophilic carrier, and at least one lipophilic carrier.

Non-limiting examples of lipophilic additives may include, but are not limited to, lipophilic surfactants, triglycerides, oils, fatty acids, fatty acid glycerides, tocopherols, tocopherol derivatives, or mixtures comprising any thereof.

As used herein, a surfactant is considered to be a lipophilic surfactant when it has an HLB value of 10 or less. Various lipophilic surfactants may be used including, but not limited to, mono-, di-glycerides of fatty acids like glyceryl monolinoleate (e.g., MAISINE® 35-1), mono- and di glycerides of caprylic, capric acid (e.g., CAPMUL® MCM), glyceryl monooleate, reaction mixtures of alcohols or polyalcohols with a variety of natural and/or hydrogenated oils such as PEG-5 hydrogenated castor oil, PEG-7 hydrogenated castor oil, PEG-9 hydrogenated castor oil, PEG-6 corn oil (e.g., LABRAFIL® M 2125 CS), PEG-6 almond oil (e.g., LABRAFIL®M 1966 CS), PEG-6 apricot kernel oil (e.g., LABRAFIL® M 1944 CS), PEG-6 olive oil (e.g., LABRAFIL® M 1980 CS), PEG-6 peanut oil (e.g., LABRAFIL® M 1969 CS), PEG-6 hydrogenated palm kernel oil (e.g., LABRAFIL® M 2130 BS), PEG-6 palm kernel oil (e.g., LABRAFIL® M 2130 CS), PEG-6 triolein (e.g., LABRAFIL® M 2735 CS), PEG-8 corn oil (e.g., LABRAFIL® WL 2609 BS), PEG-20 corn glycerides (e.g., CROVOL® M40), PEG-20 almond glycerides (e.g., CROVOL® A40), lipophilic polyoxyethylene-polyoxypropylene block co-polymers (e.g., PLURONIC® L92, L101, L121, etc.); propylene glycol fatty acid esters, such as propylene glycol monolaurate (e.g., Lauroglycol FCC), propylene glycol ricinoleate (e.g., Propymuls), propylene glycol monooleate (e.g., Myverol P-06), propylene glycol dicaprylate/dicaprate (e.g., CAPTEX® 200), and propylene glycol dioctanoate (e.g., CAPTEX® 800), propylene glycol monocaprylate (e.g., CAPRYOL® 90); propylene glycol oleate (e.g., Lutrol OP2000); propylene glycol myristate; propylene glycol mono stearate; propylene glycol hydroxy stearate; propylene glycol ricinoleate; propylene glycol isostearate; propylene glycol mono-oleate; propylene glycol dicaprylate/dicaprate; propylene glycol dioctanoate; propylene glycol caprylate-caprate; propylene glycol dilaurate; propylene glycol distearate; propylene glycol dicaprylate; propylene glycol dicaprate; mixtures of propylene glycol esters and glycerol esters such as mixtures composed of the oleic acid esters of propylene glycol and glycerol (e.g., ARLACEL® 186); sterol and sterol derivatives such as cholesterol, sitosterol, phytosterol, phytosterol fatty acid esters, PEG-5 soya sterol, PEG-10 soya sterol, PEG-20 soya sterol, and the like; glyceryl palmitostearate, glyceryl stearate, glyceryl distearate, glyceryl monostearate, or a combination thereof; sorbitan fatty acid esters such as sorbitan monolaurate (e.g., Arlacel 20), sorbitan monopalmitate (e.g., Span-40), sorbitan monooleate (e.g., Span-80), sorbitan monostearate, and sorbitan tristearate, sorbitan monolaurate, sorbitan monopalmitate, sorbitan monooleate, sorbitan trioleate, sorbitan sesquioleate, sorbitan tristearate, sorbitan monoisostearate, sorbitan sesquistearate, and the like; unionized fatty acids such as capric acid, caprylic acid, oleic acid, linoleic acid, myristic acid, menthol, menthol derivatives, lecithin, phosphatidyl choline, bile salts, and the like, and mixtures thereof. It is important to note that some lipophilic surfactants may also function as the solubilizer component of the compositions and oral dosage forms.

In certain embodiments, the lipophilic surfactant may be selected from the group consisting of glyceryl monolinoleate (e.g., MAISINE® 35-1), mono- and di glycerides of caprylic, capric acid (e.g., CAPMUL® MCM), glyceryl monooleate, propylene glycol mono caprylate, propylene glycol oleate, propylene glycol monostearate, propylene glycol monolaurate, propylene glycol mono-oleate, propylene glycol dicaprylate/dicaprate, sorbitan monooleate, PEG-5 hydrogenated castor oil, PEG-7 hydrogenated castor oil, PEG-9 hydrogenated castor oil, PEG-6 corn oil, PEG-6 almond oil, PEG-6 apricot kernel oil, PEG-6 olive oil, PEG-6 peanut oil, PEG-6 hydrogenated palm kernel oil, sorbitan monolaurate (e.g., Arlacel 20), sorbitan monopalmitate, sorbitan monooleate, sorbitan monostearate, sorbitan tristearate, sorbitan monolaurate, sorbitan monopalmitate, sorbitan monooleate, sorbitan trioleate, sorbitan sesquioleate, sorbitan tristearate, sorbitan monoisostearate, and combinations thereof.

In some embodiments, the lipophilic surfactants can comprise at least about 50% weight of the total pharmaceutically acceptable carrier. It should be noted that the combinations of two or more lipophilic surfactants from the same or different classes therein are also within the scope of this disclosure and are together can be referred to as the lipophilic surfactant, unless otherwise stated.

Non-limiting examples of hydrophilic additives may include, but are not limited to, hydrophilic surfactants; celluloses such as hydroxypropyl celluloses low molecular weight, low viscosity types (e.g., METHOCEL® E5, E6, E10 E15, LV100, etc., grades) and hydroxypropyl celluloses having higher molecular weight, medium to high viscosity (e.g., METHOCEL® K4M, K15M, K100M, etc.); polyvinyl pyrrolidone (e.g., Kollidon k17, K30, etc.), polyvinyl acetate, polyvinyl alcohol, polyvinylpyrrolidone, vinylpyrrolidone-vinyl acetate copolymer, polyethylene glycol; ionized fatty acids such as capric acid, caprylic acid, oleic acid, linoleic acid, myristic acid; and combinations comprising any thereof.

In one embodiment, the hydrophilic additive may be a hydrophilic surfactant. A surfactant is considered to be a hydrophilic surfactant when it has an HLB value of greater than 10. Non-limiting examples of hydrophilic surfactants include non-ionic surfactants, ionic surfactants and zwitterionic surfactants. Specifically, the hydrophilic surfactants suitable for the current disclosure may include, but are not limited to, alcohol-oil transesterification products; polyoxyethylene hydrogenated vegetable oils; polyoxyethylene vegetable oils; alkyl sulfate salts, dioctyl sulfosuccinate salts; polyethylene glycol fatty acids esters; polyethylene glycol fatty acids mono- and di-ester mixtures; polysorbates, polyethylene glycol derivatives of tocopherol and the like.

It should be noted that the combinations of two or more hydrophilic surfactants from the same or different classes are within the scope of this disclosure and together may be referred to as the hydrophilic surfactant, unless explicitly specified.

Non-limiting examples of hydrophilic surfactants may include PEG-8 caprylic/capric glycerides, lauroyl macrogol-32 glyceride, stearoyl macrogol glyceride, PEG-40 hydrogenated castor oil, PEG-35 castor oil, sodium lauryl sulfate, sodium dioctyl sulfosuccinate, polyethylene glycol fatty acids mono- and di-ester mixtures, polysorbate 80, polysorbate 20, polyethylene glycol 1000 tocopherol succinate, phytosterols, phytosterol fatty acid esters, and mixtures thereof.

In some embodiments, surfactants utilized in the disclosed pharmaceutical compositions may include sterols and derivatives of sterols. In various embodiments, these surfactants are hydrophilic or lipophilic. Examples of hydrophilic sterol surfactants are lanosterol PEG-24 cholesterol ether (e.g., Solulan C-24, Amerchol), PEG-30 soya sterol (e.g., Nikkol BPS-30, from Nikko), PEG-25 phyto sterol (e.g., Nikkol BPSH-25 from Nikko), PEG-30 cholestanol (e.g., Nikkol DHC, from Nikko). Examples of lipophilic sterol surfactants are cholesterol, sitosterol, phytosterol (e.g., GENEROL series from Henkel), PEG-5 soya sterol (e.g., Nikkol BPS-S, from Nikko), PEG-10 soya sterol (e.g., Nikkol BPS-10 from Nikko), PEG-20 soya sterol (e.g., Nikkol BPS-20 from Nikko).

In one embodiment, the hydrophilic additive may comprise at least about 20% weight of the total pharmaceutical carrier. In another embodiment, the hydrophilic additive can comprise at least about 5% weight of the carrier. In another embodiment, the hydrophilic additive may comprise less than about 5% weight of the carrier.

Hydrophilic or lipophilic additives may be an optional component in the compositions and dosage forms thereof, to achieve the mean serum rotigotine Cmax within the desirable effective therapeutic response upon single oral administration, such that the serum rotigotine levels may be sustained in most of the patients at levels more than 0.04 ng/ml for a large percentage of the dosing period with a patient-friendly regimen (i.e., practical hydroxy N-substituted-2-aminotetralin equivalent daily dose, less frequent administration in a day, and fewer number of dosage units per administration).

The disclosed pharmaceutical compositions may include other carrier solubilizers, including organic co-solvents, such as ethanol, PEG 300, PEG 400, propylene glycol, glycerol, sorbitol, benzyl alcohol, benzyl benzoate, dimethyl acetamide, glycofurol, triacetin, or triethyl citrate.

When appropriate, the disclosed composition may further include at least one other active agent selected from the group consisting of an anticonvulsant, an opioid, a CGRP antagonist, a NMDA receptor blocker, a cannabinoid, a bradykinin antagonist, acetaminophen, dextromethorphan, a NSAID, a COX-2 selective inhibitor, a sedative, an antidepressant, a tranquilizer, a neuroprotective agent, an antipsychotic, an anxiolytic, an anti-migraine agent, and mixtures of any thereof.

In another embodiment, the compositions or the dosage forms here include a bioreversible derivative of hydroxy N-substituted-2-aminotetralin that comprises about 0.04 wt % to about 50 wt % of the composition or the dosage form, and wherein the composition includes about 50 wt % to about 100 wt % of lipophilic additive and about 0 wt % to about 50 wt % of hydrophilic additive. In a specific embodiment, the lipophilic additive can be lipophilic surfactant and the hydrophilic additive may be hydrophilic surfactant.

In a further embodiment, the bioreversible derivative of hydroxy N-substituted-2-aminotetralins is not solubilized at 30° C., or above 30° C., or at a temperature range above 30° C., including 30° C. to about 40° C. In an additional more specific embodiment, the bioreversible derivative of hydroxy N-substituted-2-aminotetralin is not fully dissolved in the lipophilic additive or the composition at human body temperature.

In one embodiment, the hydrophilic additive may comprise at least about 20% weight of the composition. In another embodiment, the hydrophilic additive may comprise at least about 10 wt % of the composition. In another embodiment, the hydrophilic additive may comprise less than 5 wt % of the composition.

The bioreversible derivative of hydroxy N-substituted-2-aminotetralinpresent in the oral pharmaceutical compositions and dosage forms of this disclosure may be present in both dissolved and "not dissolved" form. For example, in one embodiment, the oral pharmaceutical composition or dosage form (e.g., capsule or tablet) may include a lipophilic additive and the bioreversible derivative of hydroxy N-substituted-2-aminotetralin is not fully dissolved in the lipophilic additive at 20° C. In another embodiment, the oral pharmaceutical composition or dosage form (e.g., capsule or tablet) may include a lipophilic additive and the bioreversible derivative of hydroxy N-substituted-2-aminotetralin is not fully dissolved in the lipophilic additive at human body temperature.

The compositions and the dosage forms (e.g., capsule or tablet) hereof may also include one or more of other additives selected from binders, buffers, diluents, disintegrants, flavors, colorants, taste-masking agents, resins, pH modifiers, lubricants, oxidants, thickening agent, opacifying agent, humectants, desiccants, effervescing agents, plasticizing agents and the like.

The disclosed oral compositions may be formulated, e.g., to take any dosage form commonly known in the pharmaceutical arts such as granules, tablet or capsule. In one embodiment, the oral pharmaceutical compositions of the disclosure may be formulated as oral dosage forms such as capsules or tablets or solutions or suspensions. In one embodiment, the oral dosage form may be a capsule having a pharmaceutical composition of the disclosure disposed therein. Both soft and hard gelatin and non-gelatin capsules may be used. The capsule size may be any size known in the art and can vary depending on the desired dosage amount. For instance, in one embodiment, the capsule may be a hard gelatin capsule having a fill volume of about 0.1 mL to about 1.1 mL. Similarly, in another embodiment, the capsule may be a soft gelatin capsule having a fill volume of about 0.05 mL to about 1.5 mL.

In a specific embodiment, the disclosed compositions may be formulated in the form of granules, powder mixtures or tablets. In a specific embodiment, the bioreversible derivative present in the dosage form may be present in the form of crystalline nanoparticles, crystalline milled, crystalline micronized or amorphous particles, or a mixture of both. In another specific embodiment, the bioreversible derivative present in these dosage form may be present in the form of crystalline, non-crystalline or amorphous particles or a mixtures thereof having an average particle size (diameter) of about 2000 nm or less, 1500 nm or less, 1000 nm, 800 nm or less, 600 nm or less, 500 nm or less, 400 nm or less, 300 nm or less, 250 nm or less, 200 nm or less, 100 nm or less, 50 nm or less, or 25 nm or less; or the average particle size or $D_{50}$ (median size distribution) of the crystalline, non-crystalline or amorphous particles or a mixtures thereof is in the range 10 nm to 2000 nm, 10 nm to 1500 nm, 10 nm to 1000 nm, 10 nm to 800 nm, 10 nm to 750 nm; 10 nm to 600 nm, 10 nm to 500 nm, 10 nm to 400 nm, 10 nm to 300 nm, 10 nm to 250 nm, 10 nm to 200 nm, or 10 nm to 100 nm.

In another specific embodiment, a solution of the bioreversible derivative of hydroxy N-substituted-2-aminotetralins in a carrier (e.g., lipophilic additive or hydrophilic additive or combinations thereof). Such solutions may be dispersed (e.g., by adsorption) in a solid carrier such colloidal silicon dioxide, lactose, calcium silicate, magnesium aluminum silicates, microcrystalline cellulose or combinations thereof, etc., and prepared as powder mixtures or granules or pellets to be disposed/filled into capsules or sachets, or admixed with tableting aids and compressed as tablets. Such sachets, capsules or tablets can also be formulated to contain an additional amount of the respective bioreversible derivative of hydroxy N-substituted-2-aminotetralin in crystalline and/or non-crystalline form, such that in the final composition or dosage form the total bioreversible derivative amount exists as a combination of at least two of the forms including solution, crystalline and non-crystalline forms, at about 20° C. or at about human body temperature or at 30° C. or above 30° C. including the range 30° C. to 40° C. In a further embodiment, these dosage forms provide serum hydroxy N-substituted-2-aminotetralin levels and the pharmacokinetic parameters disclosed in the current disclosure for the select hydroxy N-substituted-2-aminotetralin upon single administration or two consecutive or three consecutive administrations or upon steady state.

The dosage forms (e.g., capsule or tablet) may be immediate release, controlled release such as extended release, targeted release, enteric release, delayed release dosage form or combinations thereof. When formulated as oral dosage forms, including the disclosed capsule or tablet dosage forms, the dosage forms may be formulated for once-a-day administration or for twice-a-day administration or thrice-a-day administration. The compositions and oral dosage forms may be formulated for administration without the meal. Alternatively, the compositions and oral dosage forms may be formulated for administration with a meal, including once-a-day administration with a meal. Thus, the compositions and oral dosage forms may be administered with a meal, or without the meal (fasted state) or independent of meal or meal content.

In one embodiment, the composition or dosage form (e.g., capsule or tablet) may be administered with a meal, such as a meal that provides about 200 to about 1000 calories of energy of which 20-35% come from fats in the meal. In another embodiment, the composition or the dosage form may be administered with a standard meal. In another embodiment, the composition or capsule dosage form may be administered with a meal that provides about 50% of the calories derived from the fat. In another embodiment, the composition or the dosage form may be administered with a high-fat, high calorie meal. In another embodiment, the composition or the dosage form may be administered with a meal that provides about 500 to about 1000 calories of energy. In another embodiment, the composition or the dosage form may be administered with a meal that provides about 400 to about 700 calories derived from the fat therein. The compositional make-up of the meals that are administered may vary depending on the tastes and dietary needs of a subject. However, in some situations it may be beneficial to administer the compositions and oral dosage forms with meals that provide low or no fat or up to about 50 g of fat. In one embodiment, the meal may provide about 10 g to about 50 g of fat. In yet a further embodiment, the meal can provide about 20-35 g of fat.

In another embodiment, the disclosed composition or the disclosed dosage form may be administered orally to a subject, along with a meal such as breakfast, snack, food, lunch, dinner, etc. In a specific embodiment, the meal may comprise from about 15% to about 55% fat. In another specific embodiment, the meal may comprise from, about 20% to about 35% fat. In another specific embodiment, the meal may comprise about 20-55% fat. In another specific embodiment, the meal may comprise about 15-55% fat.

In a specific embodiment, the compositions and the dosage forms containing bioreversible derivative of hydroxy N-substituted-2-aminotetralin may enable to provide the pharmacokinetic benefits to a subject when administered orally along with meal containing about 35 g±20 g fat content. In another embodiment, the serum T pharmacokinetic benefit provided by the select bioreversible derivative of hydroxy N-substituted-2-aminotetralin compositions and dosage forms of this disclosure when administered with a meal containing about 30% to 35% fat is not statistically significantly different compared that when administered with a meal containing as low as 15% to 20% fat or a meal containing as high as 50% to 55% fat.

The oral pharmaceutical composition or the oral dosage forms (e.g., capsule or tablet) may be formulated to provide specific desirable pharmacokinetic outcomes. In one embodiment, upon single dose administration to human, the composition or the dosage form provides a mean peak serum hydroxy N-substituted-2-aminotetralin Cmax per mg of bioreversible derivative of hydroxy N-substituted-2-aminotetralin equivalent administered of at least about $2.5 \times 10^{-10}$ $ml^{-1}$.

In one embodiment, when ester is the bioreversible derivative of hydroxy N-substituted-2-aminotetralin, the daily dose of the ester may be about 0.5 mg to about 400 mg of hydroxy N-substituted-2-aminotetralin equivalent for Parkinson's disease. However, therapeutic effective doses may be higher or lower for other therapies, e.g., dose for RLS are typically half to a third or to fourth or eighth of doses need for Parkinson's disease therapy.

In another embodiment, when ester is the bioreversible derivative of hydroxy N-substituted-2-aminotetralin, the daily dose of the ester may be from about 1 mg to about 250 mg, or form about 10 mg to about 100 mg of the hydroxy N-substituted-2-aminotetralin equivalent.

In one embodiment, the bioreversible derivative of hydroxy N-substituted-2-aminotetralin may comprise about 0.05% to 50% by weight of the oral pharmaceutical composition or capsule dosage form. In another embodiment, the bioreversible derivative of hydroxy N-substituted-2-aminotetralin may comprise about 0.1% to about 30%, or about 0.5% to about 20%, or more specifically, about 0.1%, about 0.2%, about 0.3%, about 0.5%, about 0.6%, about 0.7%, about 1%, about 2%, or about 5% by weight composition, of the oral pharmaceutical composition or dosage form (e.g., capsule or tablet).

The compositions and dosage forms (e.g., capsule or tablet), described herein, can include a variety of pharmaceutically acceptable carriers known in the art. Non-limited examples of components that can be included as components of the pharmaceutical carrier include lipophilic additives, lipophilic surfactants, hydrophilic additives, hydrophilic surfactants, triglycerides, oils, fatty acid, or fatty acid glycerides, and combinations thereof.

Also provided is a method of treating a human subject in need of hydroxy N-substituted-2-aminotetralin therapy is provided. The method may include administering any of the oral pharmaceutical compositions or dosage forms (e.g., capsule or tablet), disclosed herein. The oral pharmaceutical compositions and the dosage forms of the disclosure may be used to treat any condition associated with hydroxy N-substituted-2-aminotetralin need.

In one particular embodiment, an oral unit dosage form for a human subject in need of rotigotine or (6S)-(−)-5-hydroxy-N-propyl-2-aminotetralin is disclosed. The oral unit dosage form comprises a 5-hydroxy bioreversible derivative of rotigotine, or an enantiomer or salt or prodrug thereof; and a pharmaceutically acceptable carrier. The pharmaceutically acceptable carrier may include at least one additive selected from the group consisting of lipophilic additives and hydrophilic additives. The oral unit dosage form provides a daily dose of the rotigotine or the prodrug or salt or enantiomer thereof, of about 0.5 mg to about 400 mg of the rotigotine equivalent, based on single unit or multiple unit oral dosing.

All doses of the disclosed bioreversible derivative of hydroxy N-substituted-2-aminotetralins are expressed as equivalent of hydroxy N-substituted-2-aminotetralins that the patient is in need of. For example, a dose of the decanoate ester bioreversible derivative of rotigotine (FW 469.7) is expressed as dose of rotigotine (FW 315.47) equivalent; therefore, 12 mg of rotigotine free base equivalent of rotigotine decanoate free base equals to 17.9 mg of rotigotine decanoate. Also, to note that for example 10 mg of rotigotine free base is equivalent to 11.2 mg of rotigotine hydrochloride salt, and for example 14.9 mg of rotigotine decanoate free base is equivalent to 16 mg of rotigotine decanoate hydrochloride salt. Therefore it is also to be noted that for example 10 mg of rotigotine free base is equivalent to 16 mg of rotigotine decanote hydrochloride. In the present disclosure, the hydroxy N-substituted-2-aminotetralin equivalent or rotigotine equivalent is to be interpreted as its dose equivalent of its corresponding free base independent of the salt or ester form of the hydroxy N-substituted-2-aminotetralin.

In some embodiments, the oral unit dosage form provides a daily dose of the rotigotine or the prodrug or salt or enantiomer thereof, of about 1 mg to about 250 mg of the rotigotine equivalent, based on a single unit or multiple unit oral dosing.

In some embodiments, the oral unit dosage form provides a daily dose of the rotigotine or the prodrug or salt or enantiomer thereof, of about 10 mg to about 100 mg of the rotigotine equivalent, based on a single unit or multiple unit oral dosing.

In some embodiments, the oral unit dosage form provides a hydroxy N-substituted-2-aminotetralin mean Cmax value in a subject of hydroxy N-substituted-2-aminotetralin orally administered such oral dosage form of at least about 0.04 ng/ml after single dose. In some embodiments, the oral unit dosage form provides a hydroxy N-substituted-2-aminotetralin mean Cmax value in a subject of hydroxy N-substituted-2-aminotetralin orally administered such oral dosage form of no greater than about 6 ng/ml, after single dose. In some embodiments, the oral unit dosage form provides a hydroxy N-substituted-2-aminotetralin mean Cmax value in a subject of hydroxy N-substituted-2-aminotetralin orally administered such oral dosage form of at least about 0.04 ng/ml, but not greater than about 6 ng/ml, after single dose. In some embodiments, the oral unit dosage form provides a hydroxy N-substituted-2-aminotetralin Cmax value in a subject orally administered such oral dosage form of no greater than about 6 ng/ml after single dose In some embodiments, the oral unit dosage form provides a ratio of mean serum level of hydroxy N-substituted-2-aminotetralin to hydroxy N-substituted-2-aminotetralin equivalent dose in mg, Cmax/mg, value in a subject orally administered such oral dosage form of about $1.0 \times 10^{-10}$ ml$^{-1}$ to about $12 \times 10^{-6}$ ml$^{-1}$.

In some embodiments, the oral unit dosage form provides a ratio of mean serum level of hydroxy N-substituted-2-aminotetralin to hydroxy N-substituted-2-aminotetralin equivalent dose in mg, Cmax/mg, value in a subject orally administered such oral dosage form of about $5 \times 10^{-10}$ ml$^{-1}$ about $8 \times 10^{-6}$ ml$^{-1}$.

In some embodiments, the oral unit dosage form provides a ratio of mean maximum steady state serum levels of hydroxy N-substituted-2-aminotetralin Css-max to hydroxy N-substituted-2-aminotetralin equivalent dose in mg, Css-max/mg, value in a subject orally administered such oral dosage form of about $2.5 \times 10^{-10}$ ml$^{-1}$ to about $20 \times 10^{-6}$ ml$^{-1}$.

In some embodiments, the oral unit dosage form provides a hydroxy N-substituted-2-aminotetralin Cavg value of at least about 0.04 ng/ml. In some embodiments, the oral unit dosage form provides a hydroxy N-substituted-2-aminotetralin Cavg value of no greater than about 4 ng/ml. In some embodiments, the oral unit dosage form provides a hydroxy N-substituted-2-aminotetralin Cavg value of at least about 0.04 ng/ml, but not greater than about 4 ng/ml.

In one particular embodiment, a dosage form that may be orally administered to a mammal subject in need of rotigotine therapy is disclosed. The dosage form comprises a 5-hydroxy bioreversible derivative of rotigotine, or an enantiomer or salt or prodrug thereof; and a pharmaceutically acceptable carrier. The dosage form provides a mean serum $AUC_{0-24}$ of rotigotine of at least about 0.5 ng·hr·ml$^{-1}$ after a single dose oral administration of a therapeutically effective amount to the mammal subject when administered with a meal to the subject. In some embodiments, a dosage form provides a mean serum $AUC_{0-24}$ of rotigotine of no greater than about 94 ng·hr·ml$^{-1}$. In some embodiments, a dosage form provides a mean serum $AUC_{0-24}$ of rotigotine of at least about 0.5 ng·hr/ml, but not greater than about 94 ng·hr·ml$^{-1}$. In one embodiment the dosage form provides a mean serum $AUC_{0-24}$ of rotigotine of at least about 0.5 ng·hr·ml$^{-1}$ after a single dose oral administration of a therapeutically effective amount to the mammal subject when administered independent of the meal to the subject.

In some embodiments, the dosage form provides a mean serum $AUC_{0-24}$ of rotigotine per mg of the rotigotine equivalent administered of about $1.25 \times 10^{-9}$ hr·ml$^{-1}$ to about $188 \times 10^{-6}$ hr·ml$^{-1}$.

In some embodiments, the dosage form is orally administered to the mammal subject with a meal that comprises at least about 15 grams of fat.

The disclosed compositions may be useful for treating several disease states, more particularly CNS disorders such as Parkinson's disease and restless leg syndrome.

It is noteworthy that the discussion relating to compositional components that can be used in the oral pharmaceutical compositions is also equally applicable to the dosage form embodiments (e.g., capsule dosage form) and related methods, disclosed herein, unless expressly stated to the contrary. It is also noteworthy that the discussion relating to compositional components that can be used in the oral pharmaceutical compositions is also equally applicable to the tablet dosage form embodiments and related methods, disclosed herein, unless expressly stated to the contrary. Thus, for example, teachings regarding the use of lipophilic additives and/or hydrophilic additives for use in the oral pharmaceutical compositions, disclosed herein, are also equally applicable to the capsule or tablet dosage forms and related methods, described herein, and vice versa.

It is to be understood that this disclosure is not limited to the particular process steps and materials disclosed herein below. The disclosure is extended to equivalents thereof, as would be recognized by those ordinarily skilled in the relevant arts. It should also be understood that terminology employed herein is used for the purpose of describing particular embodiments only and is not intended to be limiting.

Several derivatives of hydroxy N-substituted-2-aminotetralins were identified and evaluated for C log P values as shown in Appendix A-C. The derivatives were formulated into compositions as shown in TABLES 1 and 1A.

TABLES 1 and 1A show the typical components and their relative proportions of the tested compositions having the bioreversible derivative hydroxy N-substituted-2-aminotetralins or salt thereof shown in Appendix A-C. Carrier and adjuvant, if any, in TABLE 1A could be liquid or non liquid substance typically used and amenable into making dosage forms disclosed in this invention.

Examples of lipophilic additives may include, but not limited to, triglyceride, oil, lipophilic surfactant, sterol, or tocopherol. By way of non-limiting example, hydrophilic additives may be hydrophilic surfactant.

TABLE 1

Compositions by % weight of the Compositions 1-3

| Compound | Composition 1 | Composition 2 | Composition 3 |
|---|---|---|---|
| Bioreversible derivative of A2-A113 or salt thereof | 0.1-50 | | |
| Bioreversible derivative of B2-B10 or salt thereof | | 0.1-50 | |
| Bioreversible derivative of C4-C20 or salt therof | | | 0.1-50 |
| Carrier | 5-99.9 | 5-99.9 | 5-99.9 |
| Adjuvant | q.s. 100% | q.s. 100% | q.s. 100% |

TABLE 1A

Various Carriers for the Tested Compositions 1-3 of TABLE 1.

| Carrier | 1a | 1b | 1c | 1d | 2a | 2b | 2c | 2d | 3a | 3b | 3c | 3d |
|---|---|---|---|---|---|---|---|---|---|---|---|---|
| Lipophilic additive | 100 | | 5-95 | | 100 | | 5-95 | | 100 | | 5-95 | |
| Hydrophilic additive | | 100 | | 5-95 | | 100 | | 5-95 | | 100 | | 5-95 |

TABLE 1B shows each components and its relative proportions in the tested Composition 1C, which contains the bioreversible derivative of rotigotine. In TABLE 1B, the in U.S. Patent Application Publication No. 2012/0148675 for testosterone undecanoate were also included in the disclosure.

TABLE 1B

Various Dosage Forms Containing Composition 1C with Bioreversible Derivative of Rotigotine

| Component | 1c-1 | 1c-2 | 1c-3 | 1c-4 | 1c-5 | 1c-6 | 1c-7 | 1c-8 | 1c-9 | 1c-10 |
|---|---|---|---|---|---|---|---|---|---|---|
| Rotigotine Bioreversible Derivative | 0.1-50 | 0.1-50 | 0.1-50 | 0.1-50 | 0.1-50 | 0.1-50 | 0.1-50 | 0.1-50 | 0.1-50 | 0.5-15 |
| Oleic acid | 5-95 | | | | | | | | | 30-70 |
| Long chain triglyceride | | 5-95 | | | | | | | | |
| Long chain glyceride | | | 5-95 | | | | | | | |
| Medium chain triglyceride | | | | 5-95 | | | | | | |
| Medium chain glyceride | | | | | 5-95 | | | | | |
| Solubilizer | | | | | | 5-95 | | | | |
| Hydrophilic additive: e.g. CREMOPHOR ® RH 40 | | | | | | | 5-95 | | | 5-30 |
| Hydrophilic surfactant: e.g. TWEEN ™ 80 | | | | | | | | 5-95 | | |
| Hydrophilic surfactant: e.g. LABRASOL ® | | | | | | | | | 5-95 | |
| Adjuvant | q.s. to 100% | q.s. to 100% | q.s. to 100% | q.s. to 100% | q.s. to 100% | q.s. to 100% | q.s. to 100% | q.s. to 100% | q.s. to 100% | q.s. to 100% | long chain glyceride used is glyceryl monolinoleate, MAISINE® 35-1, medium chain glyceride is capmul, and solubilizer is PEG 400 or ethanol. Long chain triglyceride is corn oil, and medium chain triglyceride is Miglyol (fractionated coconut oil). CREMOPHOR® RH 40 compound is PEG-40 hydrogenated castor oil available from BASF Corporation. TWEEN™ 80 surfactant is an ethoxylated (20) sorbitan ester based on a natural fatty acid (oleic acid), available from Croda International Plc. Compound LABRASOL® is caprylocaproyl macrogolglyceride available from Gattefossé Co. Ltd. (Cedex, France).

Additionally, solid dosage forms of bioreversible derivatives of hydroxy N-substituted-2-aminotetralin as described Comparative Pharmacokinetic Study for the Compositions Comprising Various Bioreversible Derivative of Rotigotine For each of the bioreversible derivatives of rotigotine in TABLE 1C, dosage form 1c-10 was prepared. Various bioreversible derivatives were individually administered to human subjects in their respective dosage form with a standard meal, as a single 12 mg rotigotine equivalent dose to subjects.

Serial blood samples were drawn at predetermined time (e.g., t=0, 12, 24, etc.) and analyzed for rotigotine concentration using a validated HPLC-MS/MS analytical method. The rotigotine Cmax, ratio of rotiogtine peak levels to rotigotine equivalent, Cmax/mg, rotiogtine $Cavg_{t1-t2}$, rotigotine steady state maximum concentration, Css-max, rotigotine $AUC_{t1-t2}$ and ratio of rotigotine area under the curve to rotigotine equivalent dose in mg, $AUC_{t1-t2}$/mg, were calculated in the serum of the subjects. Pharmacokinetic and statistical analyses were performed on the data obtained from the subjects, the pharmacokinetic parameters were defined as follows:

$AUC_{t1-t2}$: the area under the serum concentration versus time curve, from time t1 (in hours) to time t2 (in hours) measurable concentration of the administered drug, as calculated by the linear trapezoidal method. For, e.g., $AUC_{t0-t24}$ refers to the area under the serum concentration versus time curve, from time 0 (zero) hours to time 24 hours post-administration of dose.

Cmax: the maximum measured serum concentration of the administered drug.

$Cavg_{t1-t2}$: the average serum concentration of bioreversible derivative of rotigotine obtained by dividing the $AUC_{t1-t2}/|t2-t1|$, where in t is time post-administration of dose expressed in hours.

mean: average value of measured parameter of all individual subjects. Unless mentioned otherwise, all pharmacokinetic parameters are mean values.

Dose is the single dose in mg administered of bioreversible derivative of rotigotine as equivalent of rotigotine, e.g., 17.9 mg of rotigotine decanoate free base is equivalent to 12 mg of rotigotine free base.

Css-max: the maximum steady state serum concentration of rotigotine typically achieved upon 3-7 days post daily dosing.

TABLE 1C shows comparative pharmacokinetic results for the tested Composition 1c-10 containing various bioreversible derivative of rotigotine.

TABLE 1C-continued

Pharmacokinetic Parameters for Serum Rotigotine of Tested Dosage Form of Compositions 1c-10 Containing Bioreversible Derivative of Rotigotine

| | Estimated ClogP | Mean Cmax (ng/ml) | Mean AUC (ng · hr · ml$^{-1}$) | $Cavg_{t1-t2}$ (ng/ml) | Mean Css-max (ng/ml) |
|---|---|---|---|---|---|
| A6-1c-10 caproate | 7.16 | <0.04 | <0.5 | <0.04 | <0.1 |
| A112-1c-10 2-methoxy phenyl | 6.80 | <0.04 | <0.5 | <0.04 | <0.1 |
| A110-1c-10 2-amino phenyl | 6.83 | <0.04 | <0.5 | <0.04 | <0.1 |
| A106-1c-10 benzoyl | 7.07 | <0.04 | <0.5 | <0.04 | <0.1 |
| A100-1c-10 propyl carbamate | 5.71 | <0.04 | <0.5 | <0.04 | <0.1 |
| A7-1c-10 enanthate | 7.69 | >0.04 | <0.5 | <0.04 | <0.1 |
| A8-1c-10 caprylate | 8.23 | >0.04 | >0.5 | >0.04 | >0.1 |
| A9-1c-10 nanoate | 8.76 | >0.04 | >0.5 | >0.04 | >0.1 |
| A10-1c-10 caprate | 9.29 | >0.04 | >0.5 | >0.04 | >0.1 |
| A11-1c-10 undecanoate | 9.82 | >0.04 | >0.5 | >0.04 | >0.1 |
| A12-1c-10 laurate | 10.3 | >0.04 | >0.5 | >0.04 | >0.1 |
| A14-1c-10 myristate | 11.4 | >0.04 | >0.5 | >0.04 | >0.1 |
| A15-1c-10 palmitate | 12.4 | <0.04 | <0.5 | <0.04 | <0.1 |

TABLE 2

Pharmacokinetic Parameters of the Tested Dosage Forms, at Varied Doses of Composition 1c-10 Containing an Example Bioreversible Derivative of Rotigotine, the Caprate Ester (Compound A10)

| Dose (mg) as rotigotine equivalent | Mean Cmax (ng/ml) | Mean Cmax/mg (ml$^{-1}$) | Mean Css-max (ng/ml) | Mean Css-max/mg (ml$^{-1}$) | Cavg (ng/ml) | Mean AUC (ng · hr · ml$^{-1}$) | Mean AUC/mg (hr.$^{-1}$) |
|---|---|---|---|---|---|---|---|
| 500 | >6 | >12 × 10$^{-6}$ | >10 | >20 × 10$^{-6}$ | >4 | >94 | >188 × 10$^{-6}$ |
| 0.1 | <0.04 | <1.0 × 10$^{-10}$ | <0.1 | <2.5 × 10$^{-10}$ | <0.04 | <0.5 | <1.25 × 10$^{-9}$ |
| 0.5-400 | >0.04 | 1.0 × 10$^{-10}$-12 × 10$^{-6}$ | >0.1 | 2.5 × 10$^{-10}$-20 × 10$^{-6}$ | 0.04-4 | 0.5-94 | 1.25 × 10$^{-9}$-188 × 10$^{-6}$ |
| 1-250 | >0.04 | 1.0 × 10$^{-10}$-12 × 10$^{-6}$ | >0.1 | 2.5 × 10$^{-10}$-20 × 10$^{-6}$ | 0.04-4 | 0.5-94 | 1.25 × 10$^{-9}$-188 × 10$^{-6}$ |
| 10-100 | >0.04 | 1.0 × 10$^{-10}$-12 × 10$^{-6}$ | >0.1 | 2.5 × 10$^{-10}$-20 × 10$^{-6}$ | 0.04-4 | 0.5-94 | 1.25 × 10$^{-9}$-188 × 10$^{-6}$ |

TABLE 1C

Pharmacokinetic Parameters for Serum Rotigotine of Tested Dosage Form of Compositions 1c-10 Containing Bioreversible Derivative of Rotigotine

| | Estimated ClogP | Mean Cmax (ng/ml) | Mean AUC (ng · hr · ml$^{-1}$) | $Cavg_{t1-t2}$ (ng/ml) | Mean Css-max (ng/ml) |
|---|---|---|---|---|---|
| A3-1c-10 propionate | 5.57 | <0.04 | <0.5 | <0.04 | <0.1 |
| A5-1c-10 valerate | 6.63 | <0.04 | <0.5 | <0.04 | <0.1 |

TABLE 2 shows pharmacokinetic results for the tested dosage forms at different doses of Composition 1c-10 containing Compound A10 of APPENDIX A, which was a bioreversible caprate (decanoate) ester derivative of rotigotine.

The dosage form of TABLE 2 were orally administered to human subjects with standard meal or without the meal (fasted) as single 12 mg rotigotine equivalent dose. Serial blood samples were drawn for the human subjects at pre-determined time (e.g., t=0, 12, 24, etc.) and analyzed to determine pharmacokinetic parameters in the serum of the subjects.

TABLE 3 shows the desired PK parameters of the tested dosage form of the example ester of TABLE 2 that gave desired PK parameters when administered with and without meals.

TABLE 3

PK Parameters with and without the Meal for Select Dosage Forms of TABLE 2

| Fed/Fasted Ratio Range of Mean AUC | Fed/Fasted Ratio Range of Mean Cmax |
|---|---|
| 2-5 | 2-8 |

TABLE 4 showed non-limiting examples of preferred bioreversible derivatives of rotigotine and other hydroxy N-substituted-2-aminotetralins. As discussed previously, the disclosed bioreversible derivatives had a C log P value of from about 7 to about 11.5, more preferably at a C log P value of from about 8 to about 11, most preferably at a C log P value of about 8.5 to about 10.5.

TABLE 4

Non-Limiting Examples of Bioreversible Derivatives of Rotigotine or Rotigotine Salts such as Hydrochloride and other Hydroxy N-Substituted-2-Aminotetralins or its Salts.

| Bioreversible Derivative | Preferred ClogP (7.0-11.5) | More preferred ClogP (8-11) | Most preferred ClogP (8.5-10.5) |
|---|---|---|---|
| Rotigotine | A6-caproate, A7-enanthate, A8-caprylate, A9-nanoate, A10-caprate, A11-undecanoate, A12-laurate, A13-tridecanoate, A14-myristate | A8-caprylate, A9-nanoate, A10-caprate, A11-undecanoate, A12-laurate, A13-tridecanoate | A8-caprylate, A9-nanoate, A10-caprate, A11-undecanoate, A12-laurate |
| (6S)-(-)-5-Hydroxy-N-propyl-2-aminotetralin | B2-laurate, B3-tridecanoate, B4-myristate, B5-palmitate, B6-stearate, B7-oleate | B3-tridecanoate, B4-myristate, B5-palmitate, B7-oleate | B3-tridecanoate, B4-myristate, B5-palmitate |
| Hydroxy DPAT | C4-caprylate, nanoate, C5-decanoate, C6-undecanoate, C7-laurate, C8-tridecanoate, C9-myristate, C11-cypionate, C12-buciclate | nanoate, C5-decanoate, C6-undecanoate, C7-laurate, C8-tridecanoate, C9-myristate, C12-buciclate | C5-decanoate, C6-undecanoate, C7-laurate, C8-tridecanoate, C12-buciclate |

TABLE 5 summarized the intrinsic lipophilicity and apparent lipophilicity of hydroxy N-substituted-2-aminotetralins in comparison with those of some examples of the corresponding bioreversible derivatives according to the disclosure.

TABLE 5

Comparison of the Intrinsic and Apparent Lipophilicity of Hydroxy N-Substituted-2-Aminotetralins and the Corresponding Bioreversible Derivatives

| Compound | Intrinsic Lipophilicity ClogP | Apparent Lipophilicity logD$_{7.4}$ |
|---|---|---|
| Rotigotine | 4.96 ± 0.35 | 1-1.9 |
| Decanoate Ester of Rotigotine (Compound A10) | 9.25 ± 0.35 | >4 |

TABLE 5-continued

Comparison of the Intrinsic and Apparent Lipophilicity of Hydroxy N-Substituted-2-Aminotetralins and the Corresponding Bioreversible Derivatives

| Compound | Intrinsic Lipophilicity ClogP | Apparent Lipophilicity logD$_{7.4}$ |
|---|---|---|
| (6S)-(-)-5-Hydroxy-N-propyl-2-aminotetralin | 2.52 ± 0.29 | -0.5 |
| Palmitate Ester of (6S)-(-)-5-Hydroxy-N-propyl-2-aminotetralin (Compound B5) | 10.03 ± 30 | 6.5-7.5 |
| Hydroxy DPAT | 3.5-4 | 0.5-1.5 |
| Laurate Ester of Hydroxy DPAT (Compound C7) | 9.66 ± 0.25 | 6.5-7.5 |

Accordingly, it has been found for the first time that a unique dose of the bioreversible derivatives of hydroxy N-substituted-2-aminotetralins may offer, upon single administration of compositions and dosage forms of these esters, adequate oral bioactivity and bioavailability, as compared to some other derivatives of hydroxy N-substituted-2-aminotetralins given orally.

Furthermore, it has been discovered that bioreversible derivative of hydroxy N-substituted-2-aminotetralins have a unique daily dose range for which, upon daily administration to subject, the following desirable pharmacokinetic parameters may be achieved:

Mean Cmax of at least about 0.04 ng/ml after single dose;

Mean Cmax of no greater than about 6 ng/ml after single dose;

Mean Cmax/mg of from about $1.0 \times 10^{-10}$ ml$^{-1}$ to about $12 \times 10^{-6}$ ml$^{-1}$, or from about $2 \times 10^{-10}$ ml$^{-1}$ to about $6 \times 10^{-6}$ ml$^{-1}$;

Mean Css-max/mg of from about $2.5 \times 10^{-10}$ ml$^{-1}$ to about $20.0 \times 10^{-6}$ ml$^{-1}$; and Ratio of mean Cmax to mean Cmin of from about 1 to about 6.

The disclosed dosage form may, upon single dose administration to a mammal subject, provide a mean serum AUC rotigotine of at least about 0.5 ng·hr·ml$^{-1}$. The disclosed dosage form may, upon single dose administration to a mammal subject, provide a mean serum AUC rotigotine of no greater than about 94 ng·hr·ml$^{-1}$. The disclosed dosage form may, upon single dose administration to a mammal subject, provide a mean serum AUC rotigotine of at least about 0.5 ng·hr·ml$^{-1}$, but not greater than about 94 ng·hr·ml$^{-1}$.

The disclosed dosage form may, upon single dose administration to mammal, provide a mean serum rotigotine AUC per mg of the bioreversible derivative of rotigotine equivalent administered of about $1.25 \times 10^{-9}$ hr·ml$^{-1}$ to about $188 \times 10^{-6}$ hr·ml$^{1}$ or a mean AUC/mg of about $2.5 \times 10^{-6}$ hr·ml$^{-1}$ to about $100 \times 10^{-6}$ hr·ml$^{-1}$.

The disclosed dosage form may, upon single dose administration to a mammal subject, provide a mean apparent $t_{1/2}$ of rotigotine of greater than about 30 minutes.

Accordingly, it has been found that an oral therapy for treatment of condition needing dopamine agonist that is convenient, safe, effective (e.g., mean Cavg t0-t24 within the therapeutic response of at least about 0.04 ng/ml or mean Cavg t0-t12 within the therapeutic response of at least about 0.04 ng/ml or mean Cavg t0-t8 within the therapeutic response of at least about 0.04 ng/ml.

A further embodiment of the disclosure is the use of prodrug derivatives of hydroxy N-substituted-2-aminotetralins, in particular as pure (S)-enantiomer, or the salts or prodrugs thereof for the preparation of a medicament for the treatment or prophylaxis of different types of depression in particular endogenous monophasic depression ("major depression"), pain, anxiety disorders, sexual dysfunctions especially male erectile dysfunction or female sexual disorder or SSRI induced sexual dysfunction, glaucoma, cognitive disorders, restless leg syndrome especially moderate to severe restless leg syndrome, restless limb disorder, neurodevelopmental type disorder, attention deficit hyperactivity syndrome (ADHS) or attention deficit hyperactivity disorder (ADHD), hyperkinetic disorder, obsessive compulsive disorder, impulsive disorder, hyperprolactinemia, hyperprolactinoma, eating disorders, neurogenerative disorder, Parkinson-associated movement disorders, dopa- and neuroleptic-induced/sensitive movement disorders, e.g., akathisia, rigor, dystonia and dyskinesia, as well as cocaine, alcohol, opiate and nicotine addiction, galactorrhea, ovarian hyperstimulation disorder, acromegaly, drug-supported ablactation after pregnancy, Parkinson-associated movement disorders, e.g., rigor, dystonia and dyskinesia; L-dopa-induced disorders, idiopathic dystonia, in particular Segawa syndrome; neuroleptic-induced (tardive) dyskinesia, dystonia and akathisia, as well as Parkinson plus syndrome. In this disclosure, under the term "opiates" both naturally occurring opiates, like morphine, as well as synthetic opiates, like heroin, are subsumed.

Further, the disclosed compositions may be suitable for the manufacture of dosage forms for treating L-dopa-sensitive movement disorders. Such movement disorders could be, for example, dyskinesia, dystonia, rigor and tremor. It is understood by the term "L-dopa-sensitive" that the movement disorder can be advantageously influenced via administration of medicaments, which influence the dopaminergic signal transduction. One typical example for this is the Segawa syndrome, an idiopathic dystonia, by which the use of L-dopa as diagnostic criteria can be used. Other examples for L-dopa-sensitive disorders are morbus Parkinson associated, or L-dopa or neuroleptic-induced movement disorders as well as the restless leg syndrome.

Morbus Parkinson associated or L-dopa or neuroleptic-induced movement disorders are, for example, dyskinesias, dystonias and walking disorders ("freezing"). With the use of L-dopa therapy, the so-called "wearing off" phenomenon regularly appears, which means a loss of activity of L-dopa, which can be mitigated or slowed through the use of monotherapy or combined therapy with suitable D3 dopamine agonists.

A preferred use of the bioreversible derivative compositions, thus, relates to the manufacture of a medicament for the treatment of movement disorders, such as dyskinesias, dystonias and walking disorders, which spontaneously appear in the process of Parkinson diseases, but which may also be induced by medication. Included in the medication-induced movement disorders, like dyskinesias and dystonias, are particularly those which are induced via L-dopa or dopamine antagonists.

In one particular embodiment, a method for treatment of dopaminergic cell loss in a subject or decreasing the progression of Parkinson's disease in a subject is disclosed. The method comprises: identifying a subject without clinically confirmed Parkinson's disease; and administering to the subject bioreversible derivative of rotigotine or a physiologically acceptable salt or enantiomer thereof, wherein the subject has at least one clinical symptom selected from the group consisting of an olfactory disorder, depression, a sleep disorder of the "REM behavior disorder" type, constipation and a short-term movement anomaly, or wherein the subject displays a mutation in a PARK gene and/or a modification to alpha synuclein or neuromelanin pattern, or wherein the subject displays a dopaminergic cell loss in substantia nigra of less than 60% before administering rotigotine or its bioreversible derivative of this disclosure wherein the subject has a UPDRS motor score of less than 10 before administering rotigotine or its bioreversible derivative or wherein the subject has a Hoehn-Yahr score of 0 or 1 or wherein the subject has one, two or three symptoms selected from the group consisting of rigor, resting tremor, bradykinesia and postural instability, to a partial degree.

In one particular embodiment, a method for treatment of dopaminergic cell loss in a subject or decreasing the progression of Parkinson's disease in a subject is disclosed. The method comprises: (a) identifying a subject without any of four cardinal symptoms of Parkinson's disease but having an increased risk of developing Parkinson's disease or wherein the subject displays a mutation in a PARK gene and/or a modification to alpha synuclein or neuromelanin pattern or wherein the subject displays a dopaminergic cell loss in substantia nigra of less than 50% before administering rotigotine or its bioreversible derivative of this disclosure; and (b) administering to the subject bioreversible derivative of rotigotine or a physiologically acceptable salt or enantiomer thereof.

In one particular embodiment, a method for treating pain in a subject is disclosed. The method comprises administering to the subject a therapeutically effective amount of bioreversible derivative of rotigotine or a pharmaceutically acceptable salt, enantiomer, prodrug or metabolite thereof wherein the pain comprises musculoskeletal pain, fibromyalgia, myofascial pain, back pain, myofascial pain syndrome, pain during menstruation, pain during osteoarthritis, pain during rheumatoid arthritis, pain during gastrointestinal inflammation, pain during inflammation of the heart muscle, pain during multiple sclerosis, pain during neuritis, pain during AIDS, pain during chemotherapy, tumor pain, headache, CPS, central pain, neuropathic pain, neuropathic pain encountered as a consequence of a metabolic disorder or degenerative disease of the nervous system, trigeminal neuralgia, shingles, stamp pain, phantom limb pain, temporo-mandibular joint disorder, nerve injury, migraine, post-herpetic neuralgia, neuropathic pain encountered as a consequence of injuries, amputation infections, metabolic disorders or degenerative diseases of the nervous system, neuropathic pain associated with diabetes, pseudesthesia, hypothyroidism, uremia, vitamin deficiencies or alcoholism, acute pain after injuries, postoperative pain, pain during acute gout, or pain from operations and wherein muscular hyperalgesia and/or muscular allodynia are reduced.

The disclosure further discloses a method for use of compositions of this disclosure for treating depression in a mammal. The method comprises administering a therapeutically effective quantity of bioreversible derivative of rotigotine or a metabolite, prodrug or physiologically acceptable salt thereof, to the mammal. wherein the depression is an endogenous depression or an organic depression not associated with Parkinson's disease or the depression is a unipolar depression (major depression) or a depressive episode of a manic-depressive disorder or the depression is an organic depression, which is independent of Parkinson's disease or the depression is a Parkinson's disease-associated depression or wherein co-medication with another antidepressant is absent.

The disclosure further discloses a method for treating a restless limb disorder such as restless leg disorder in particular moderate to severe restless leg disorder or the disorder comprises periodic limb movement disorder (PLMD), in a subject. The method comprises administering one or more doses as a monotherapy or as a co-therapy with another active agent for treatment of the disorder or a condition associated there with bioreversible derivative of rotigotine or a pharmaceutically acceptable salt, prodrug or metabolite thereof, wherein each such dose comprises an amount effective to reduce occurrence and/or severity of one or more symptoms of the disorder or is effective to effect improvement in sensory symptoms of RLS on a 0 to 10 scale or is effective to reduce severity of sensory symptoms of RLS by at least about 1 point on a 0 to 10 scale within a period of about 4 hours after administration or is effective to reduce severity of motor symptoms of RLS by at least about 3 PLMWI points or is effective to reduce severity of motor symptoms of RLS by at least about 10 PLMWI points.

The method of to treat restless leg syndrome and bioreversible derivative of the rotigotine or salt, prodrug or metabolite thereof is administered during or with about 2 hours prior to a wakeful sedentary period or a sleep period.

The disclosed pharmaceutical compositions may also be provided, independent from the diseases to be treated, as a combination preparation for simultaneous or sequential application.

For example, a dosage form unit to be sold which comprises a medication for treatment or prophylaxis of any CNS disorder such as Parkinson's disease or restless leg syndrome comprising dopaminergic agent such as L-dopa, can also encompass a pharmaceutical composition, which comprises bioreversible derivative of hydroxy N-substituted-2-aminotetralins or pharmaceutically acceptable salts or prodrugs or enantiomer thereof. In this case L-dopa and the compounds may be present in the same pharmaceutical formulation, e.g., in a combination tablet, or also in different application units, e.g., in the form of two separate tablets or in different application forms, e.g., as oral L-dopa medication and as oral bioreversible derivative of this disclosure, or as injectable or transdermal dosage forms of (S)-2-N-propylamino-5-hydroxytetralin formulation or rotigotine. As according to the need, both active agents can be applied simultaneously or separately over time.

The method of to treat pain may further comprise administering at least one further active agent wherein the at least one further active agent comprises an opioid, a CGRP antagonist, a NMDA receptor blocker, a cannabinoid, a bradykinin antagonist, acetaminophen, dextromethorphan, a NSAID, a COX-2 selective inhibitor, a sedative, an antidepressant, a tranquilizer and/or a neuroprotective agent.

The method of treat depression may further comprise administering to the mammal at least one additional active ingredient selected from the group consisting of antidepressants, antipsychotics, sedatives, anxiolytics and anti-migraine agents.

In a combination preparation, a sequential dose may be, for example, achieved by providing an administration form, e.g., an oral tablet, having two different layers with differing release profiles for the different pharmaceutically active components. It is clear to the skilled person that in the context of the current disclosure, different administration forms and application schedules are possible, all of which are subject matter of the disclosure.

A regimen for managing a restless limb disorder in a subject, may comprise: (a) administering a first dopamine agonist to the subject by an oral, transdermal or parenteral route in an amount effective for chronic treatment of the disorder; and (b) administering, orally a second dopamine agonist in an amount effective for p.r.n. treatment to reduce occurrence and/or severity of one or more breakthrough symptoms of the disorder; wherein the first and second dopamine agonists are the same or different.

In some embodiments of the regimen of above, at least the second dopamine agonist comprises bioreversible derivative of rotigotine or a pharmaceutically acceptable salt, prodrug or metabolite thereof.

Also disclosed is a regimen for treatment or propylaxis of symptoms of restless limb disorder comprising compositions of this disclosure and anticonvulsant such as gabapentin, gabapentin enacapril, pregabalin, or benzodiazepines such as diazepam, alprazolam, tamezepam, clonazepam, or dopaminergic agents such as L-dopa with carbidopa or opiates such as hydrocodone, alpha agonist such as clonidine or dopamine agonist such as amantadine, apomorphine, bromocriptine, cabergoline, carrnoxirole, (S)-didesmethylsibutramine, dopexamine, fenoldopam, ibopamine, lergotrile, lisuride, memantine, mesulergine, pergolide, piribedil, pramipexole, quinagolide, ropinirole, rotigotine, roxindole, talipexole, or a pharmaceutically acceptable salt, prodrug or metabolite thereof, or a combination thereof.

The compositions of the present disclosure may be used in treatment or prophylaxis of different types of depression in particular endogenous monophasic depression ("major depression"), pain, anxiety disorders, sexual dysfunctions especially male erectile dysfunction or female sexual disorder or SSRI induced sexual dysfunction, glaucoma, cognitive disorders, restless leg syndrome especially moderate to severe restless leg syndrome, restless limb disorder, neurodevelopmental type disorder, attention deficit hyperactivity syndrome (ADHS) or attention deficit hyperactivity disorder (ADHD), hyperkinetic disorder, obsessive compulsive disorder, impulsive disorder, hyperprolactinemia, hyperprolactinoma, eating disorders, neurogenerative disorder, Parkinson-associated movement disorders, dopa- and neuroleptic-induced/sensitive movement disorders, e.g., akathisia, rigor, dystonia and dyskinesia, as well as cocaine, alcohol, opiate and nicotine addiction, galactorrhea, ovarian hyperstimulation disorder, acromegaly treatment or prophylaxis of different types of depression in particular endogenous monophasic depression ("major depression"), pain, anxiety disorders, sexual dysfunctions especially male erectile dysfunction or female sexual disorder or SSRI induced sexual dysfunction, glaucoma, cognitive disorders, restless leg syndrome especially moderate to severe restless leg syndrome, restless limb disorder, neurodevelopmental type disorder, attention deficit hyperactivity syndrome (ADHS) or attention deficit hyperactivity disorder (ADHD), hyperkinetic disorder, obsessive compulsive disorder, impulsive disorder, hyperprolactinemia, hyperprolactinoma, eating disorders, neurogenerative disorder, Parkinson-associated movement disorders, dopa- and neuroleptic-induced/sensitive movement disorders, e.g., akathisia, rigor, dystonia and dyskinesia, as well as cocaine, alcohol, opiate and nicotine addiction, galactorrhea, ovarian hyperstimulation disorder, acromegaly drug-supported ablactation after pregnancy, Parkinson-associated movement disorders, e.g., rigor, dystonia and dyskinesia; L-dopa-induced disorders, idiopathic dystonia, in particular Segawa syndrome; neuroleptic-induced (tardive) dyskinesia, dystonia and akathisia, as well as Parkinson plus syndrome.

In one particular embodiment, the disclosed composition may be used for treating L-dopa-sensitive movement disorders. Such movement disorders include dyskinesia, dystonia, rigor and tremor, and morbus Parkinson associated, or L-dopa or neuroleptic-induced movement disorders as well as the restless leg syndrome.

According to one embodiment here, a pharmaceutical composition comprises: (a) the disclosed bioreversible derivative of hydroxy N-substituted-2-aminotetralin; and (b) at least one further active ingredient selected from the group consisting of antidepressants, antipsychotics, sedatives, anxiolytics and anti-migraine agents.

The disclosed pharmaceutical compositions may be used independent from the diseases to be treated, as a combination preparation for simultaneous or sequential application.

In one embodiment, the disclosed pharmaceutical composition may further comprise a medication for treatment or prophylaxis of any CNS disorder such as Parkinson's disease or restless leg syndrome; dopaminergic agent such as L-dopa. The L-dopa and the bioreversible derivative may be present in the same dosage form (e.g. in a combination tablet or a capsule), or in the form of two separate tablets or capsules forms (e.g. as oral L-dopa dosage form and as the bioreversible derivative dosage form).

Also described is a method of using the disclosed compositions for treating the patients with the early stages of Parkinson's disease to reduce symptoms or the patients with the later stages of Parkinson's disease when levodopa is no longer able to adequately control symptoms on its own.

In some embodiments, the disclosed method is for treating patients with Parkinson's disease, in whom approximately 70% to 80% of the dopaminergic neurons in the substantia nigra (SN) have been irreversibly damaged.

Also described is a method of using the disclosed compositions for treating patients with the onset of symptoms, such as bradykinesis, resting tremors, rigidity, and postural instability.

In some embodiments, the disclosed method is for treating dopaminergic cell loss in a subject or decreasing the progression of Parkinson's disease in a subject, wherein the subject has at least one clinical symptom selected from the group consisting of an olfactory disorder, depression, a sleep disorder of the "REM behavior disorder" type, constipation and a short-term movement anomaly.

Further described is a method for treating depression in a mammal. The method comprises administering a therapeutically effective quantity of the disclosed bioreversible derivative of hydroxy N-substituted-2-aminotetralin to the mammal, wherein the depression is an endogenous depression or an organic depression not associated with Parkinson's disease or the depression is a unipolar depression (major depression) or a depressive episode of a manic-depressive disorder or the depression is an organic depression which is independent of Parkinson's disease or the depression is a Parkinson's disease-associated depression, or wherein co-medication with another antidepressant is absent.

Further described is a method for using the disclosed oral composition for preventive uses in Parkinson's disease. In particular, disclosed are the methods for treatment of dopaminergic cell loss in a subject or decreasing the progression of Parkinson's disease in a subject without clinically confirmed Parkinson's disease, or wherein the subject has at least one clinical symptom selected from the group consisting of an olfactory disorder, depression, a sleep disorder of the "REM behavior disorder" type, constipation and a short-term movement anomaly or wherein the subject displays a mutation in a PARK gene and/or a modification to alpha synuclein or neuromelanin pattern, or wherein the subject displays a dopaminergic cell loss in substantia nigra of less than 60% before administering the disclosed bioreversible derivative of hydroxy N-substituted-2-aminotetralin, or wherein the subject has a UPDRS motor score of less than 10 before administering the disclosed bioreversible derivative of hydroxy N-substituted-2-aminotetralin, or wherein the subject has a Hoehn-Yahr score of 0 or 1, or wherein the subject has one, two or three symptoms selected from the group consisting of rigor, resting tremor, bradykinesia and postural instability, to a partial degree.

Also disclosed is a method of using a disclosed composition for treatment of dopaminergic cell loss in a subject or decreasing the progression of Parkinson's disease in a subject without any of four cardinal symptoms of Parkinson's disease but having an increased risk of developing Parkinson's disease, or wherein the subject displays a mutation in a PARK gene and/or a modification to alpha synuclein or neuromelanin pattern, or wherein the subject displays a dopaminergic cell loss in substantia nigra of less than 50% before administering rotigotine or its bioreversible derivative. The method comprises administering to the subject the bioreversible derivative of rotigotine or a physiologically acceptable salt thereof.

Additionally described is a method for using the disclosed oral composition in therapeutic effective amounts for treatment of pain, wherein the pain comprises musculoskeletal pain, fibromyalgia, myofascial pain, back pain, myofascial pain syndrome, pain during menstruation, pain during osteoarthritis, pain during rheumatoid arthritis, pain during gastrointestinal inflammation, pain during inflammation of the heart muscle, pain during multiple sclerosis, pain during neuritis, pain during AIDS, pain during chemotherapy, tumor pain, headache, CPS, central pain, neuropathic pain, neuropathic pain encountered as a consequence of a metabolic disorder or degenerative disease of the nervous system, trigeminal neuralgia, shingles, stamp pain, phantom limb pain, temporomandibular joint disorder, nerve injury, migraine, post-herpetic neuralgia, neuropathic pain encountered as a consequence of injuries, amputation infections, metabolic disorders or degenerative diseases of the nervous system, neuropathic pain associated with diabetes, pseudesthesia, hypothyroidism, uremia, vitamin deficiencies or alcoholism, acute pain after injuries, postoperative pain, pain during acute gout, or pain from operations and wherein muscular hyperalgesia and/or muscular allodynia are reduced.

Furthermore described is a method of using the disclosed oral composition in therapeutic effective amounts for treating a restless limb disorder such as restless leg disorder in particular moderate to severe restless leg disorder or the disorder comprises periodic limb movement disorder (PLMD), in a subject. The method comprises administering one or more doses as a monotherapy or as a co-therapy with another active agent for treatment of the disorder or a condition associated therewith.

In one embodiment of such method, the rotigotine equivalent dose range of about 0.5 mg to about 100 mg is used for the treatment. In other embodiment, the rotigotine equivalent dose range of about 1 mg to about 20 mg is used. In still other embodiment, the rotigotine equivalent dose range of about 3 mg to about 10 mg is used.

The disclosed composition may also be used for managing a restless limb disorder in a subject. The method of using the disclosed oral composition for treating a restless limb disorder comprises: (a) administering a first dopamine agonist to the subject by an oral, transdermal or parenteral route in an amount effective for chronic treatment of the disorder; and (b) administering, orally a second dopamine agonist in an amount effective for p.r.n. treatment to reduce occurrence and/or severity of one or more breakthrough symptoms of the disorder; wherein the first and second dopamine agonists are the same or different. In one embodiment the second dopamine agonist comprises bioreversible derivative of rotigotine or a pharmaceutically acceptable salt, or prodrug or metabolite or enantiomer thereof.

Further described is a method of using the disclosed oral composition in therapeutic effective amounts for treatment or prophylaxis of symptoms of restless limb disorder comprising anticonvulsant such as gabapentin, gabapentin enacapril, pregabalin, or benzodiazepines such as diazepam, alprazolam, tamezepam, clonezapam, or dopaminergic agents such as L-dopa with carbidopa or opiates such as hydrocodone, alpha agonist such as clonidine or dopamine agonist such as amantadine, apomorphine, bromocriptine, cabergoline, carmoxirole, (S)-didesmethylsibutramine, dopexamine, fenoldopam, ibopamine, lergotrile, lisuride, memantine, mesulergine, pergolide, piribedil, pramipexole, quinagolide, ropinirole, rotigotine, roxindole, talipexole, or a pharmaceutically acceptable salt, prodrug or metabolite thereof, or a combination thereof.

Moreover, the disclosed composition may be used for treating depression in a mammal, wherein the depression is an endogenous depression or an organic depression not associated with Parkinson's disease or the depression is a unipolar depression (major depression) or a depressive episode of a manic-depressive disorder or the depression is an organic depression which is independent of Parkinson's disease or the depression is a Parkinson's disease-associated depression or wherein co-medication with another antidepressant is absent. The method of using the disclosed oral composition for treating such depression comprises administering a therapeutically effective quantity of bioreversible derivative of rotigotine or a metabolite, or prodrug or physiologically acceptable salt or enantiomer thereof, to the mammal.

In one embodiment of such method, the composition may further comprises at least one antidepressant selected from the group consisting of selective serotonin reuptake inhibitors, mixed serotonin and noradrenalin reuptake inhibitors, selective noradrenaline reuptake inhibitors, monoamine oxidase inhibitors, alpha2 receptor modulators, serotonin receptor modulators, adenosine antagonists, sigma-opioid receptor ligands, NK antagonists, melatonin antagonists and modulators of the hypothalamus-hypophysis-adrenal axis.

In some embodiments hereof, the composition may be in a combination dosage form having two different layers with differing release profiles for the different pharmaceutically active components.

The term "oral bioavailability," as used herein, means that at least about 1% of the administered dose of the bioreversible derivative administered as hydroxy N-substituted aminotertralin equivalent that is available as an active hydroxy N-substituted aminotertralin after oral administration of such the bioreversible derivative to a subject.

In one embodiment, the disclosed composition may provide an oral bioavailability of at least about 1%. In one embodiment, the disclosed composition may provide an oral bioavailability of at least about 5%. In one embodiment, the disclosed composition may provide an oral bioavailability of at least about 10%.

In one embodiment, the disclosed composition may be taken orally with a meal. More particularly, in some embodiments, the disclosed composition may be taken orally with a meal composed of at least about 15 g of fat.

While the disclosure is susceptible to various modifications and alternative forms, specific embodiments have been shown by way of example in the drawings and have been described in detail herein. However, the disclosure is not intended to be limited to the particular forms disclosed. Rather, the disclosure is to cover all modifications, equivalents, and alternatives falling within the scope of the disclosure as defined by the following appended claims and their legal equivalents.

APPENDIX A

Rotigotine (A1) and Non-Limiting Examples of the Bioreversible Derivatives of Rotigotine (A2-A113) According to one Embodiment of the Disclosure, and their Corresponding Calculated logP (ClogP)

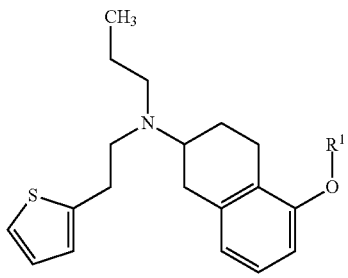

| Compound | R$^1$ | Structure | ClogP |
|---|---|---|---|
| A1 Rotigotine | H | 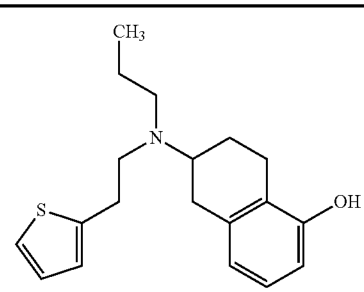 | 4.96 ± 0.35 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
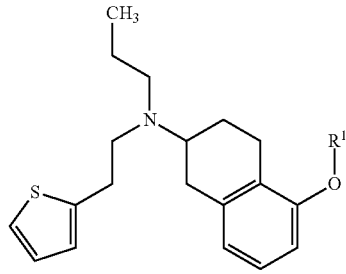
| Compound | R¹ | Structure | ClogP |
|---|---|---|---|
| A2 | Acetate (C1) | 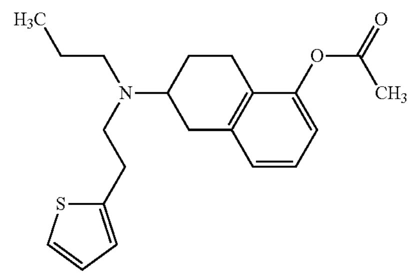 [SMILES: CCCN(CCc1cccs1)C1CCc2c(cccc2OC(C)=O)C1] | 5.04 ± 0.35 |
| A3 | Propionate (C3) | 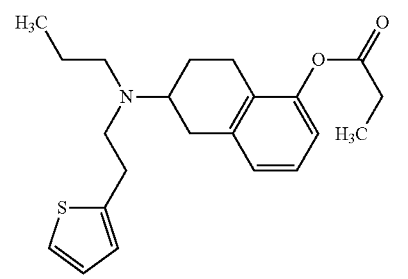 [SMILES: CCCN(CCc1cccs1)C1CCc2c(cccc2OC(=O)CC)C1] | 5.57 ± 0.35 |
| A4 | Butyrate (C4) | 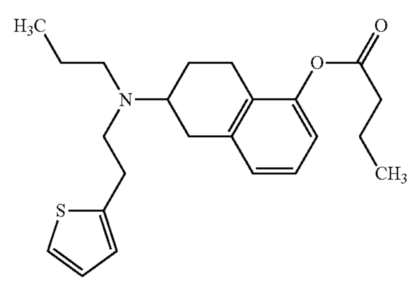 [SMILES: CCCC(=O)Oc1cccc2c1CCC(N(CCC)CCc1cccs1)C2] | 6.10 ± 0.35 |
| A5 | Valerate (C5) | 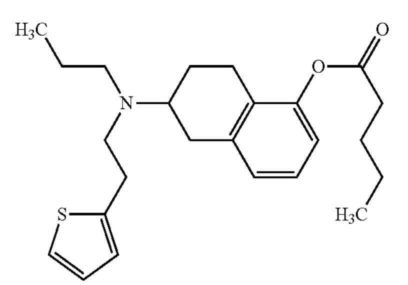 [SMILES: CCCCC(=O)Oc1cccc2c1CCC(N(CCC)CCc1cccs1)C2] | 6.63 ± 0.35 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
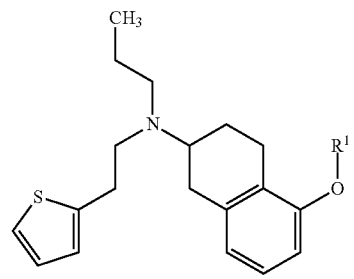
| Compound | R[1] | Structure | ClogP |
|---|---|---|---|
| A6 | Caproate (C6) | 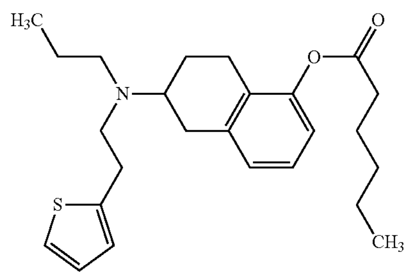 [SMILES: CCCCCC(=O)Oc1cccc2c1CCC(N(CCC)CCc1cccs1)C2] | 7.16 ± 0.35 |
| A7 | Enanthate (C7) | 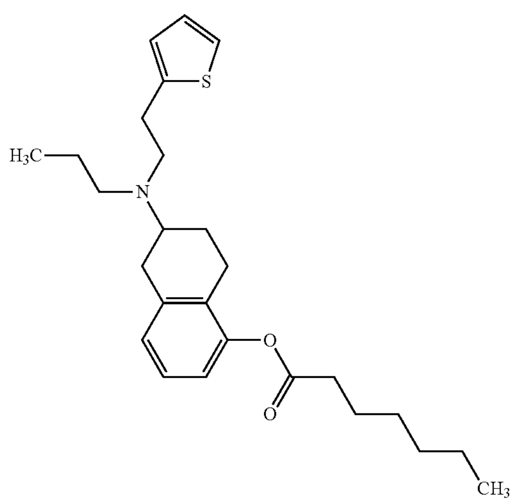 [SMILES: CCCCCCC(=O)Oc1cccc2c1CCC(N(CCC)CCc1cccs1)C2] | 7.69 ± 0.35 |
| A8 | Caprylate (C8) | 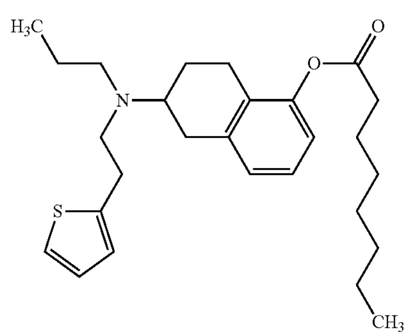 [SMILES: CCCCCCCC(=O)Oc1cccc2c1CCC(N(CCC)CCc1cccs1)C2] | 8.23 ± 0.35 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
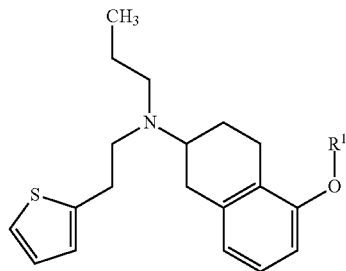
| Compound | R[1] | Structure | ClogP |
|---|---|---|---|
| A9 | Nanoate (C9) | 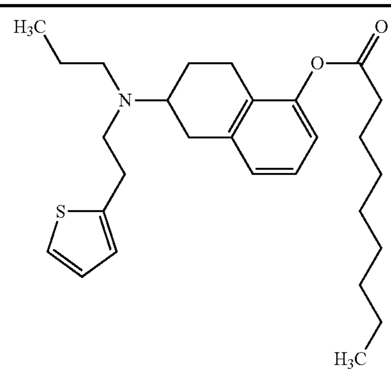 | 8.76 ± 0.35 |
| A10 | Caprate (C10) | 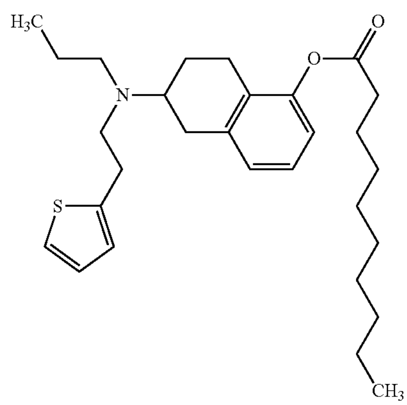 [SMILES: CCCCCCCCCC(=O)Oc1cccc2c1CCC(N(CCC)CCc1cccs1)C2] | 9.29 ± 0.35 |
| A11 | Undecanoate (C11) | 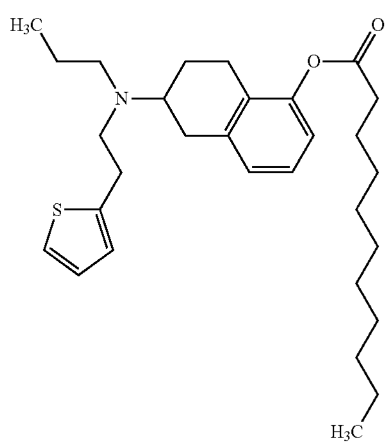 [SMILES: CCCCCCCCCCC(=O)Oc1cccc2c1CCC(N(CCC)CCc1cccs1)C2] | 9.82 ± 0.35 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
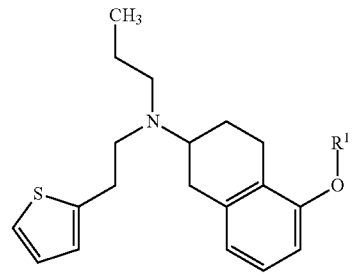
| Compound | R[1] | Structure | ClogP |
|---|---|---|---|
| A12 | Laurate (C12) | 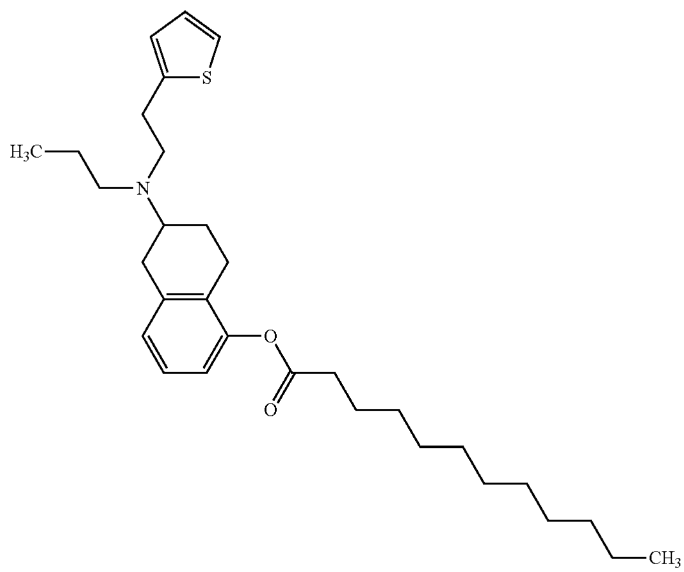 [SMILES: CCCCCCCCCCCC(=O)Oc1cccc2c1CCC(N(CCC)CCc1cccs1)C2] | 10.35 ± 0.35 |
| A13 | Tridecanoate (C13) | 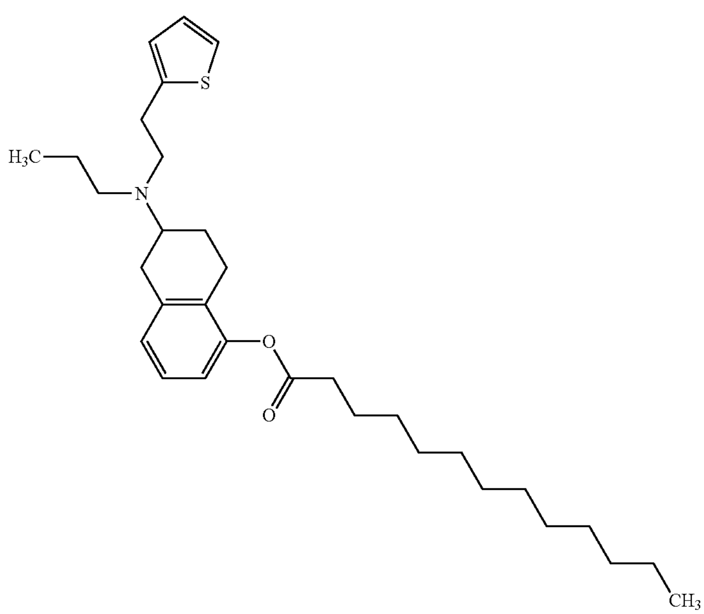 [SMILES: CCCCCCCCCCCCC(=O)Oc1cccc2c1CCC(N(CCC)CCc1cccs1)C2] | 10.88 ± 0.35 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
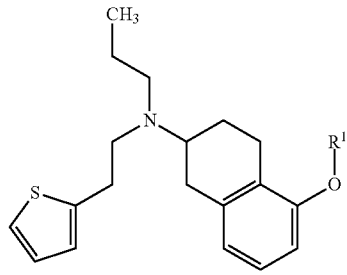
| Compound | R¹ | Structure | ClogP |
|---|---|---|---|
| A14 | Myristate (C14) | 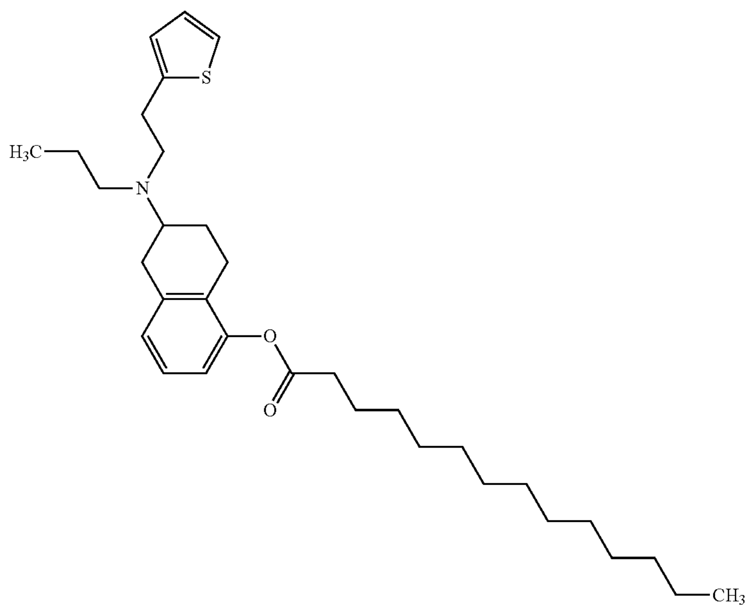 [SMILES: CCCCCCCCCCCCCC(=O)Oc1cccc2c1CCC(N(CCC)CCc1cccs1)C2] | 11.41 ± 0.35 |
| A15 | Palmitate (C16) | 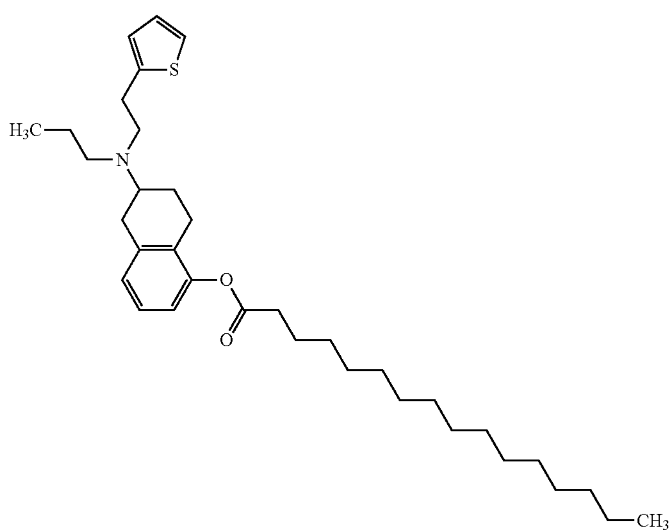 [SMILES: CCCCCCCCCCCCCCCC(=O)Oc1cccc2c1CCC(N(CCC)CCc1cccs1)C2] | 12.48 ± 0.35 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
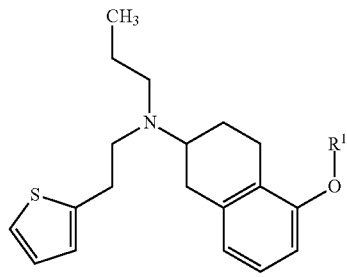
| Compound | R[1] | Structure | ClogP |
|---|---|---|---|
| A16 | t-Butyl (C5) | 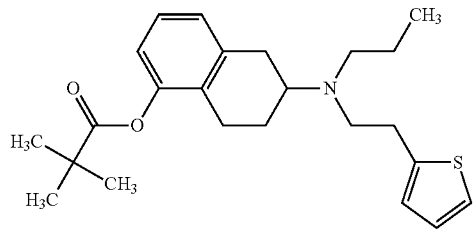 [SMILES: CCCN(CCc1cccs1)C1CCc2c(cccc2OC(=O)C(C)(C)C)C1] | 6.27 ± 0.36 |
| A17 | Isocaproate (C6) | 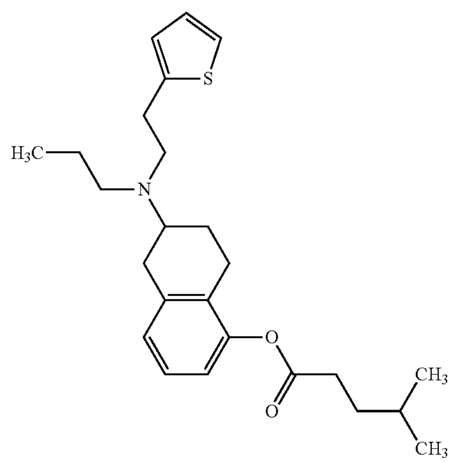 [SMILES: CCCN(CCc1cccs1)C1CCc2c(cccc2OC(=O)CCC(C)C)C1] | 6.98 ± 0.36 |
| A18 | Isoenanthate (C7) | 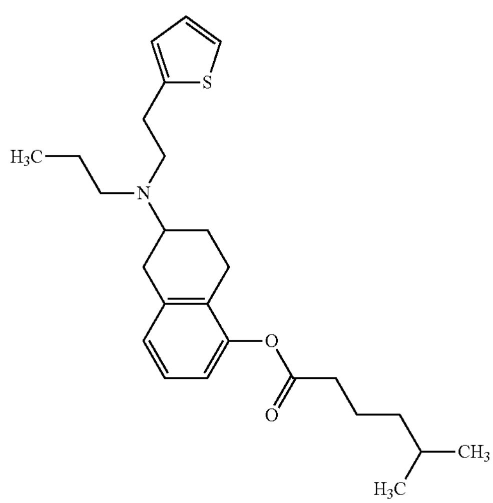 [SMILES: CCCN(CCc1cccs1)C1CCc2c(cccc2OC(=O)CCCC(C)C)C1] | 7.51 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
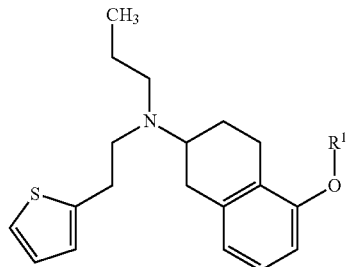
| Compound | R¹ | Structure | ClogP |
|---|---|---|---|
| A19 | Methyl Enanthate (C8) | 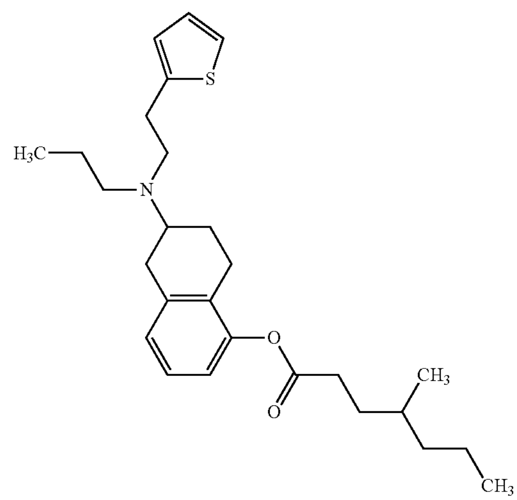 [SMILES: CCCC(C)CCC(=O)Oc1cccc2c1CCC(N(CCC)CCc1cccs1)C2] | 8.04 ± 0.36 |
| A20 | Ethyl Caproate (C8) | 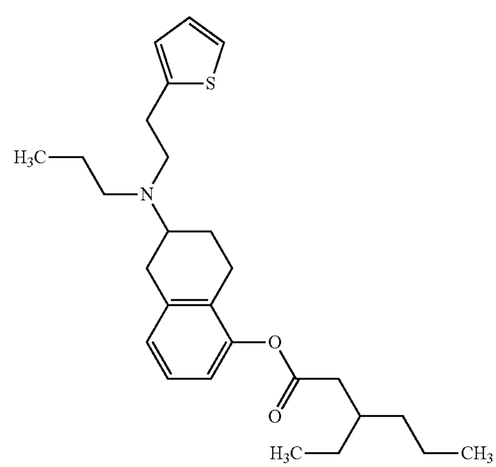 [SMILES: CCCC(CC)CC(=O)Oc1cccc2c1CCC(N(CCC)CCc1cccs1)C2] | 8.04 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
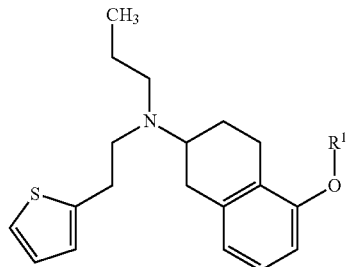
| Compound | R¹ | Structure | ClogP |
|---|---|---|---|
| A21 | Isocaprylate (C8) | 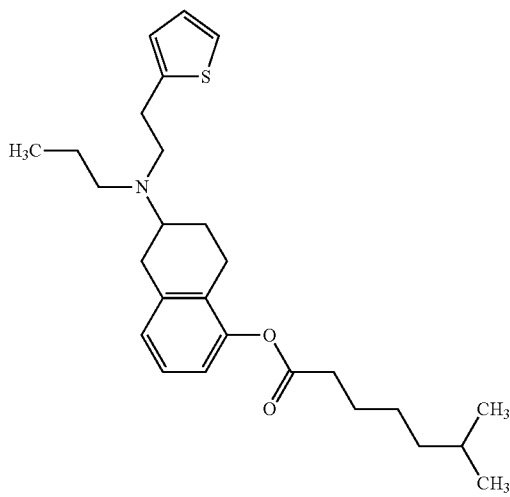 [SMILES: CCCN(CCc1cccs1)C1CCc2c(cccc2OC(=O)CCCCC(C)C)C1] | 8.04 ± 0.36 |
| A22 | Dimethyl Caproate (C8) | 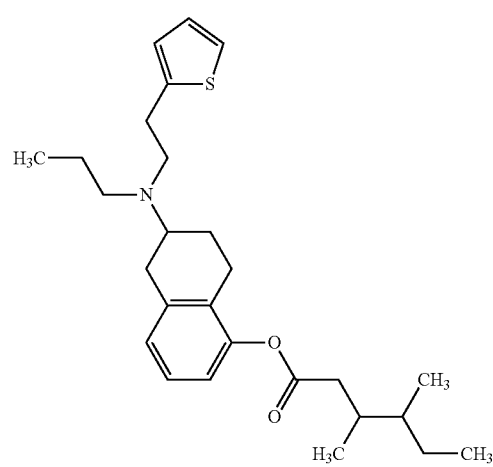 [SMILES: CCCN(CCc1cccs1)C1CCc2c(cccc2OC(=O)CC(C)C(C)CC)C1] | 7.86 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
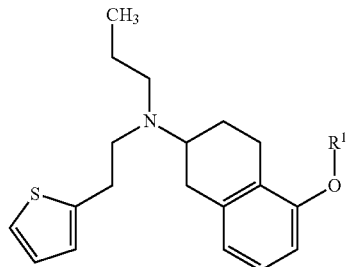
| Compound | R¹ | Structure | ClogP |
|---|---|---|---|
| A23 | Ethyl Methyl Caproate (C9) | 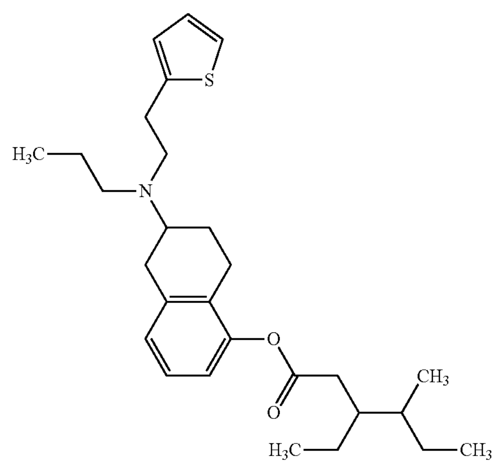 [SMILES: CCCN(CCc1cccs1)C1CCc2c(cccc2OC(=O)CC(CC)C(C)CC)C1] | 8.39 ± 0.36 |
| A24 | Dimethyl Enanthate (C9) | 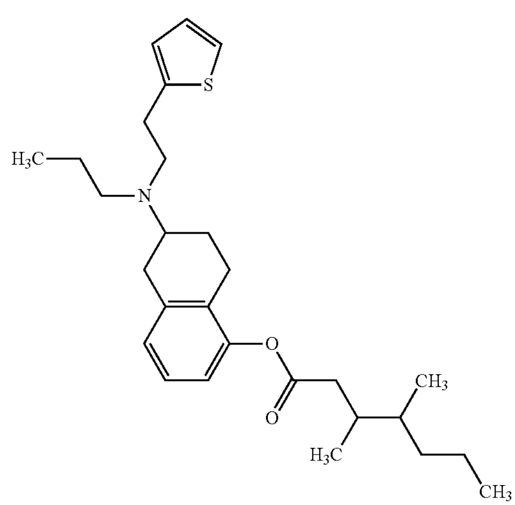 [SMILES: CCCC(C)C(C)CC(=O)Oc1cccc2c1CCC(N(CCC)CCc1cccs1)C2] | 8.39 ± 0.36 |

APPENDIX A-continued

Rotigotine (A1) and Non-Limiting Examples of the Bioreversible Derivatives of Rotigotine (A2-A113) According to one Embodiment of the Disclosure, and their Corresponding Calculated logP (ClogP)

| Compound | R[1] | Structure | ClogP |
|---|---|---|---|
| A25 | Ethyl Enanthate (C9) | 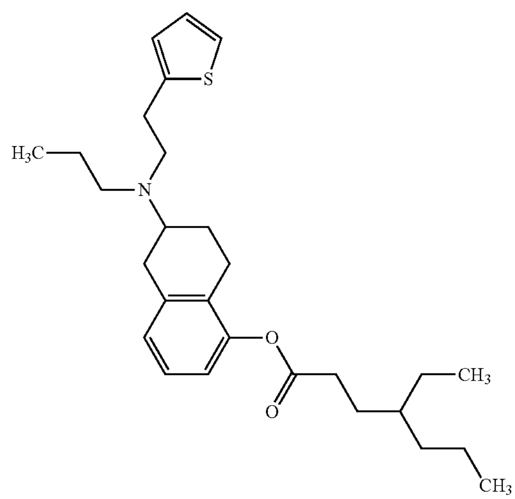 [SMILES: CCCC(CC)CCC(=O)Oc1cccc2c1CCC(N(CCC)CCc1cccs1)C2] | 8.57 ± 0.36 |
| A26 | Propyl Caproate (C9) | 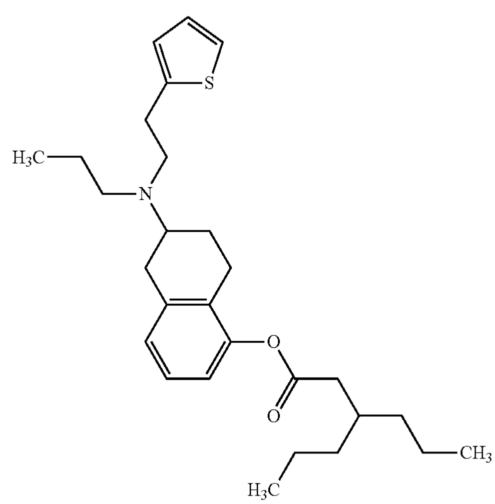 [SMILES: CCCC(CCC)CC(=O)Oc1cccc2c1CCC(N(CCC)CCc1cccs1)C2] | 8.57 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
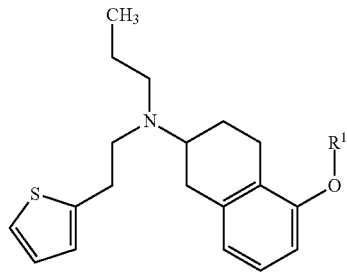
| Compound | R¹ | Structure | ClogP |
|---|---|---|---|
| A27 | Propyl Methyl Caproate (C10) | 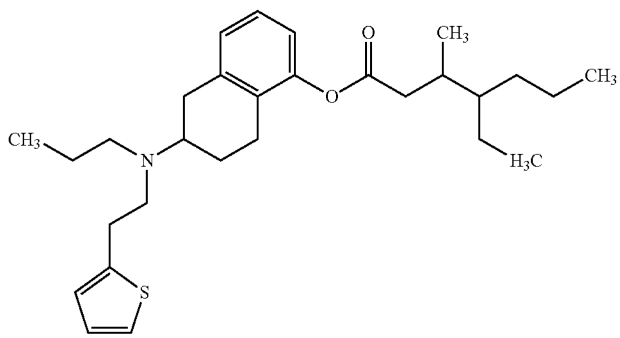 [SMILES: CCCC(CC)C(C)CC(=O)Oc1cccc2c1CCC(N(CCC)CCc1cccs1)C2] | 8.92 ± 0.36 |
| A28 | Diethyl Caproate (C10) | 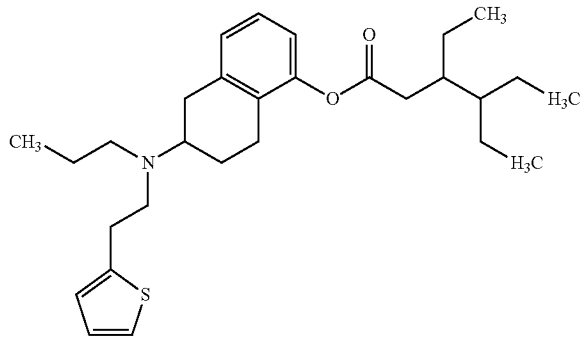 [SMILES: CCCN(CCc1cccs1)C1CCc2c(cccc2OC(=O)CC(CC)C(CC)CC)C1] | 8.92 ± 0.36 |
| A29 | Propyl Enanthate (C10) | 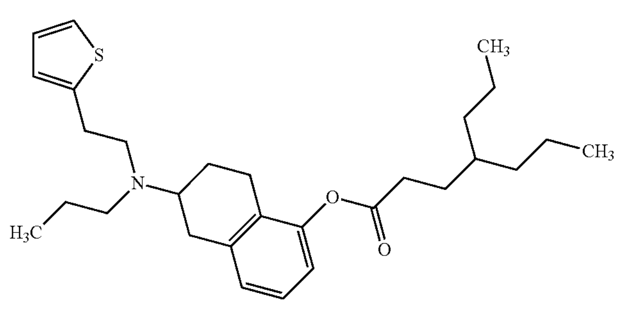 [SMILES: CCCC(CCC)CCC(=O)Oc1cccc2c1CCC(N(CCC)CCc1cccs1)C2] | 9.10 ± 0.36 |

APPENDIX A-continued

Rotigotine (A1) and Non-Limiting Examples of the Bioreversible Derivatives of Rotigotine (A2-A113) According to one Embodiment of the Disclosure, and their Corresponding Calculated logP (ClogP)

| Compound | R[1] | Structure | ClogP |
|---|---|---|---|
| A30 | Methyl, Ethyl Enanthate (C10) | 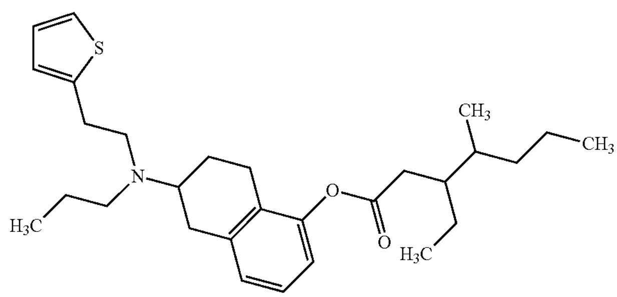 [SMILES: CCCC(C)C(CC)CC(=O)Oc1cccc2c1CCC(N(CCC)CCc1cccs1)C2] | 8.92 ± 0.36 |
| A31 | Butyl Caproate (C10) | 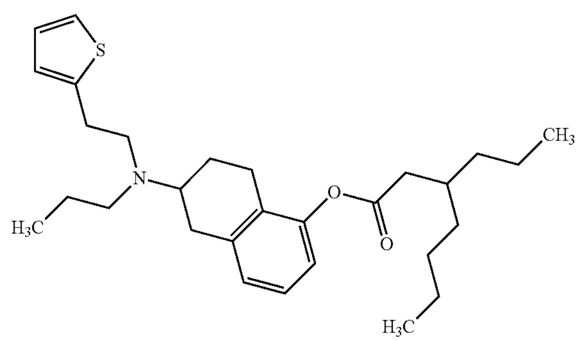 [SMILES: CCCCC(CCC)CC(=O)Oc1cccc2c1CCC(N(CCC)CCc1cccs1)C2] | 8.57 ± 0.36 |
| A32 | Isocaprate (C10) | 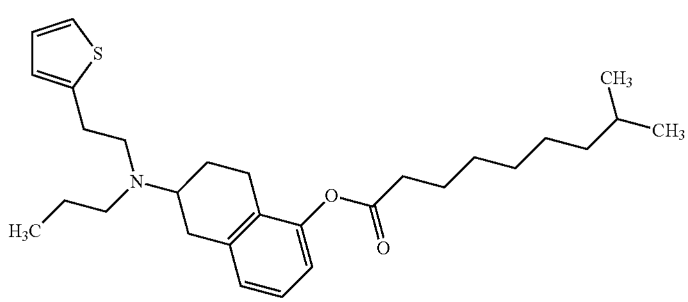 [SMILES: CCCN(CCc1cccs1)C1CCc2c(cccc2OC(=O)CCCCCCC(C)C)C1] | 9.10 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
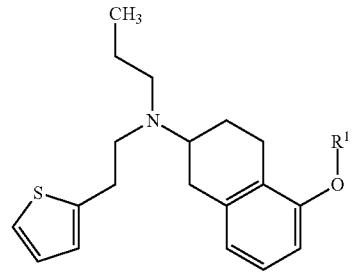
| Compound | R¹ | Structure | ClogP |
|---|---|---|---|
| A33 | Dimethyl Caprylate (C10) | 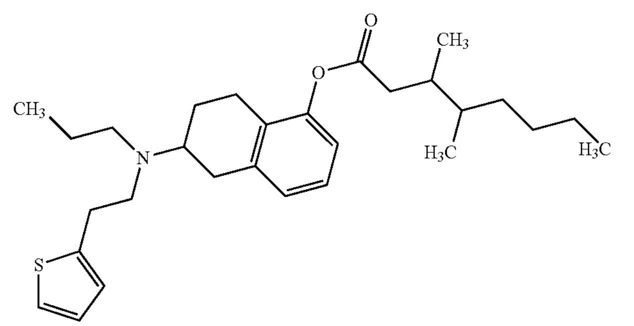 [SMILES: CCCCC(C)C(C)CC(=O)Oc1cccc2c1CCC(N(CCC)CCc1cccs1)C2] | 8.92 ± 0.36 |
| A34 | Methyl Nanoate (C10) | 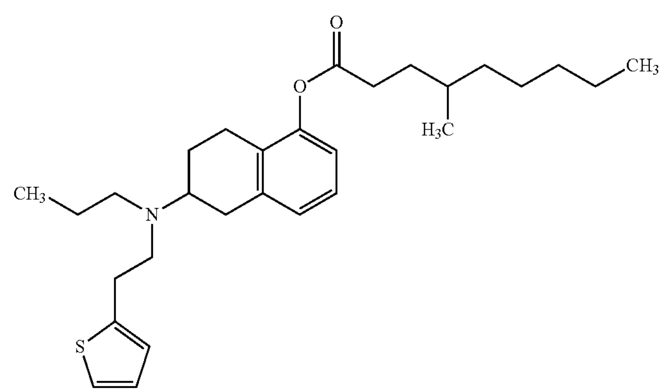 [SMILES: CCCCCC(C)CCC(=O)Oc1cccc2c1CCC(N(CCC)CCc1cccs1)C2] | 9.10 ± 0.36 |
| A35 | Butyl Enanthate (C11) | 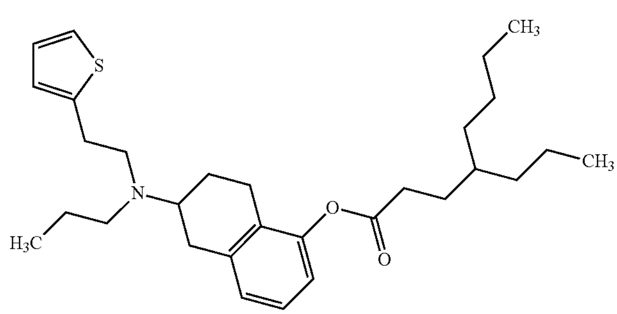 [SMILES: CCCCC(CCC)CCC(=O)Oc1cccc2c1CCC(N(CCC)CCc1cccs1)C2] | 9.64 ± 0.36 |

APPENDIX A-continued

Rotigotine (A1) and Non-Limiting Examples of the Bioreversible Derivatives of Rotigotine (A2-A113) According to one Embodiment of the Disclosure, and their Corresponding Calculated logP (ClogP)

| Compound | R¹ | Structure | ClogP |
|---|---|---|---|
| A36 | Methyl Isocaprate (C11) | 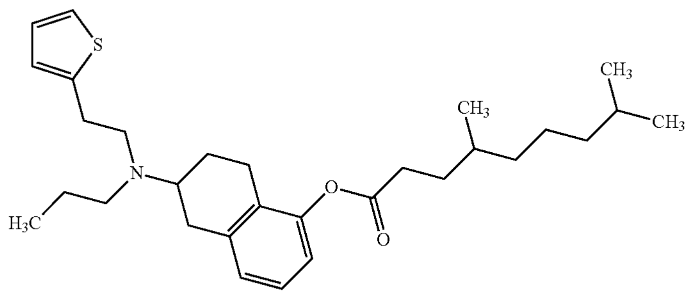 [SMILES: CCCN(CCc1cccs1)C1CCc2c(cccc2OC(=O)CCC(C)CCCC(C)C)C1] | 9.45 ± 0.36 |
| A37 | Methyl Caprate (C11) | 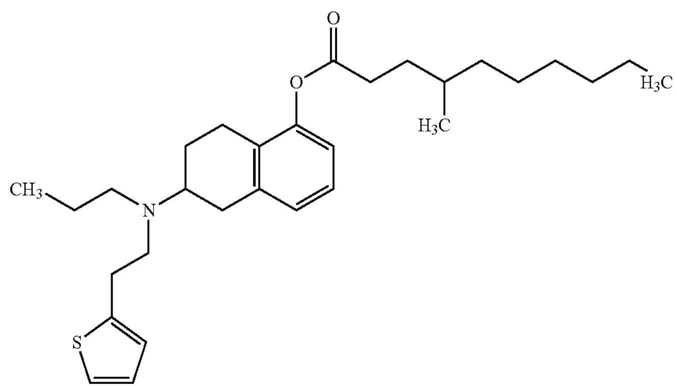 [SMILES: CCCCCCC(C)CCC(=O)Oc1cccc2c1CCC(N(CCC)CCc1cccs1)C2] | 9.64 ± 0.36 |
| A38 | Isoundecanoate (C11) | 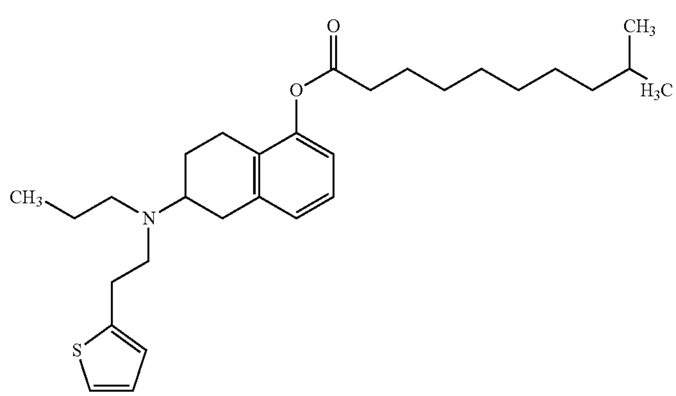 [SMILES: CCCN(CCc1cccs1)C1CCc2c(cccc2OC(=O)CCCCCCCC(C)C)C1] | 9.64 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
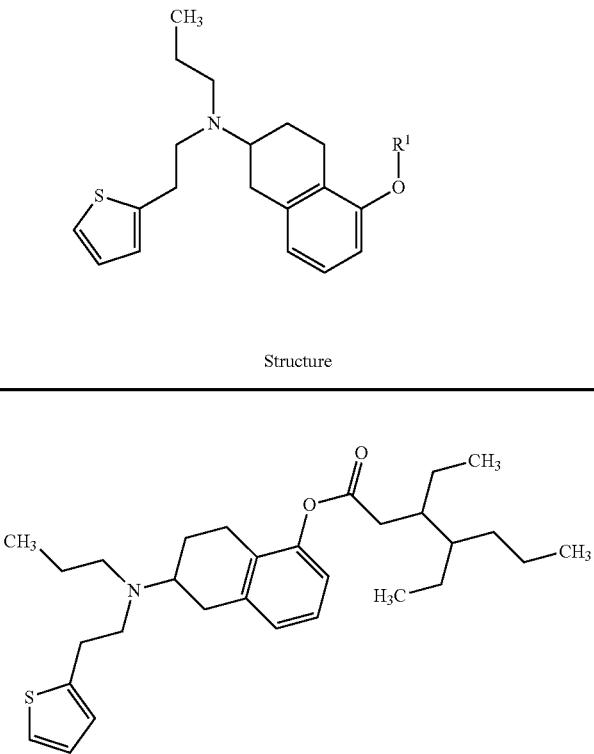
| Compound | R¹ | Structure | ClogP |
|---|---|---|---|
| A39 | Diethyl Enanthate (C11) | 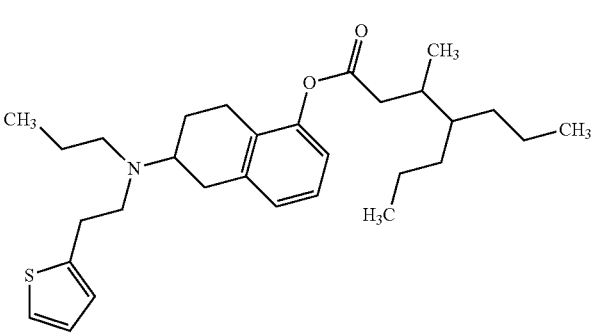 [SMILES: CCCC(CCC)C(C)CC(=O)Oc1cccc2c1CCC(N(CCC)CCc1cccs1)C2] | 9.45 ± 0.36 |
| A40 | Methyl Propyl Enanthate (C11) | 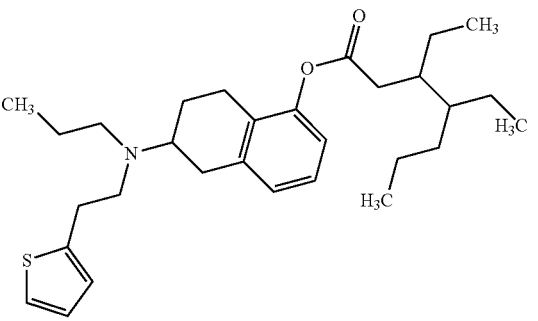 | 9.45 ± 0.36 |
| A41 | Ethyl Propyl Caproate (C11) | 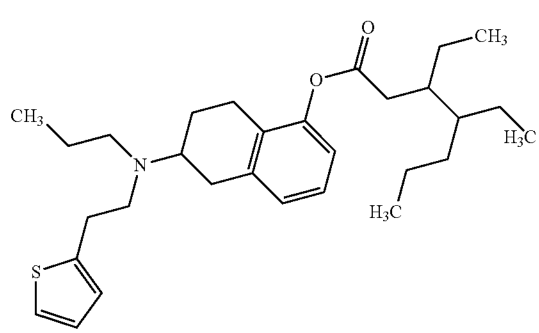 [SMILES: CCCC(CC)C(CC)CC(=O)Oc1cccc2c1CCC(N(CCC)CCc1cccs1)C2] | 9.45 ± 0.36 |

APPENDIX A-continued

Rotigotine (A1) and Non-Limiting Examples of the Bioreversible Derivatives of Rotigotine (A2-A113) According to one Embodiment of the Disclosure, and their Corresponding Calculated logP (ClogP)

| Compound | R¹ | Structure | ClogP |
|---|---|---|---|
| A42 | R-Methyl Undecanoate (C12) | 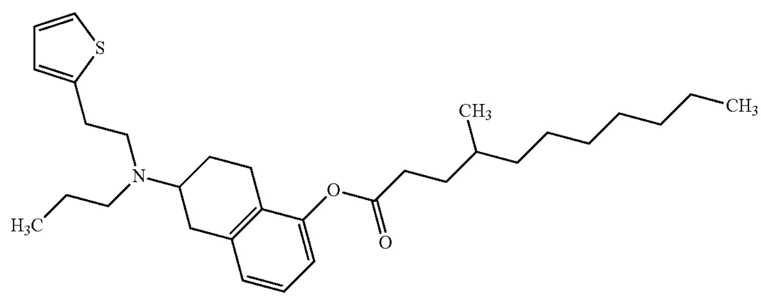 [SMILES: CCCCCCCC(C)CCC(=O)Oc1cccc2c1CCC(N(CCC)CCc1cccs1)C2] | 10.17 ± 0.36 |
| A43 | Dipropyl Caproate (C12) | 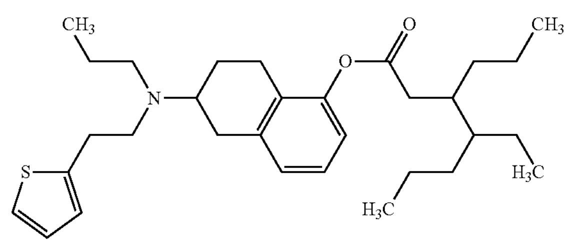 [SMILES: CCCC(CC)C(CCC)CC(=O)Oc1cccc2c1CCC(N(CCC)CCc1cccs1)C2] | 9.98 ± 0.36 |
| A44 | Ethyl Propyl Enanthate (C12) | 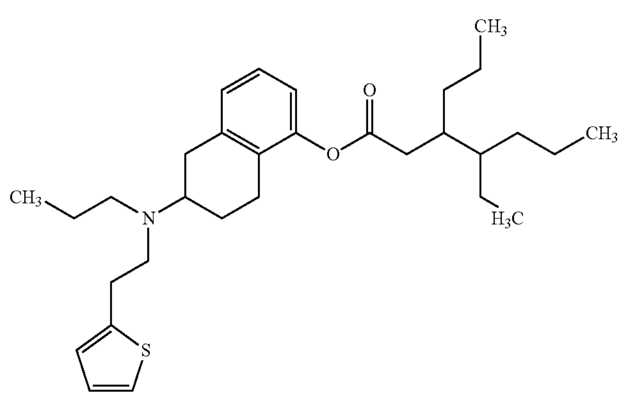 [SMILES: CCCC(CC)C(CCC)CC(=O)Oc1cccc2c1CCC(N(CCC)CCc1cccs1)C2] | 9.98 ± 0.36 |

APPENDIX A-continued

Rotigotine (A1) and Non-Limiting Examples of the Bioreversible Derivatives of Rotigotine (A2-A113) According to one Embodiment of the Disclosure, and their Corresponding Calculated logP (ClogP)

| Compound | R[1] | Structure | ClogP |
|---|---|---|---|
| A45 | Diethyl Caprylate (C12) | 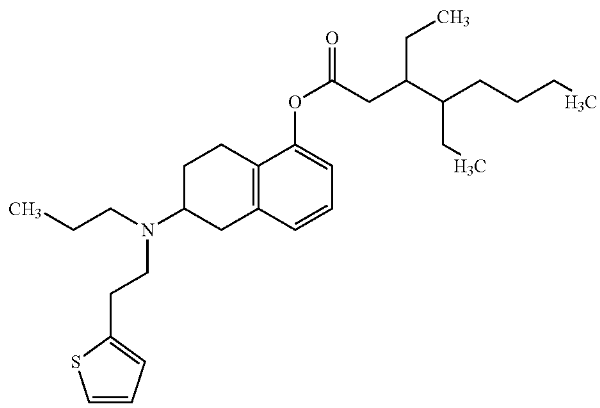 [SMILES: CCCCC(CC)C(CC)CC(=O)Oc1cccc2c1CCC(N(CCC)CCc1cccs1)C2] | 9.98 ± 0.36 |
| A46 | Propyl Methyl Caprylate C12) | 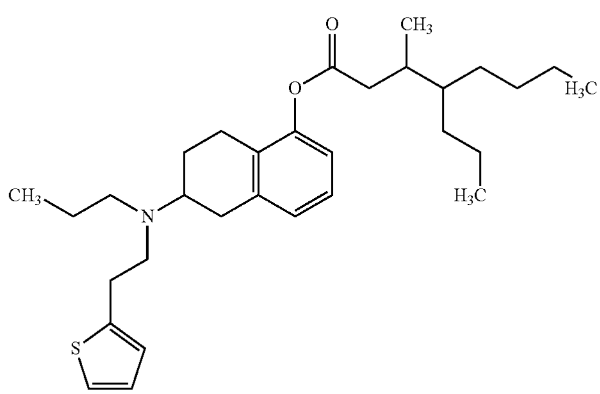 [SMILES: CCCCC(CCC)C(C)CC(=O)Oc1cccc2c1CCC(N(CCC)CCc1cccs1)C2] | 9.98 ± 0.36 |
| A47 | Methyl Isoundecanoate (C12) | 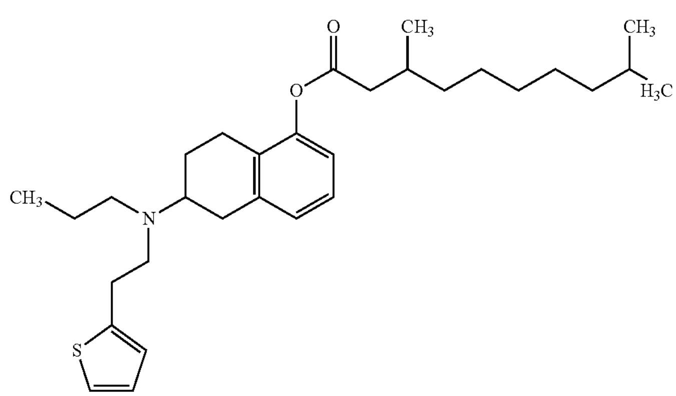 [SMILES: CCCN(CCc1cccs1)C1CCc2c(cccc2OC(=O)CC(C)CCCCCC(C)C)C1] | 9.98 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
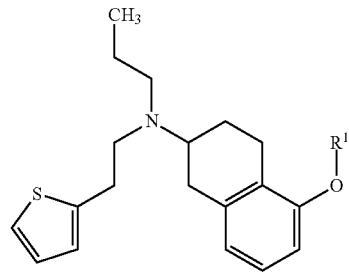
| Compound | R[1] | Structure | ClogP |
|---|---|---|---|
| A48 | Isolaurate (C12) | 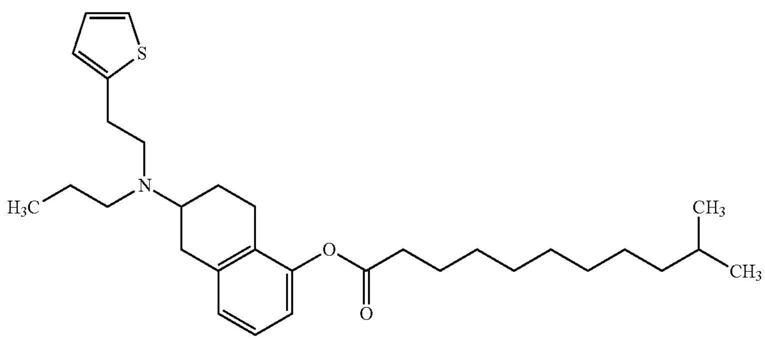 [SMILES: CCCN(CCc1cccs1)C1CCc2c(cccc2OC(=O)CCCCCCCCC(C)C)C1] | 9.10 ± 0.36 |
| A49 | Dimethyl Caprate (C12) | 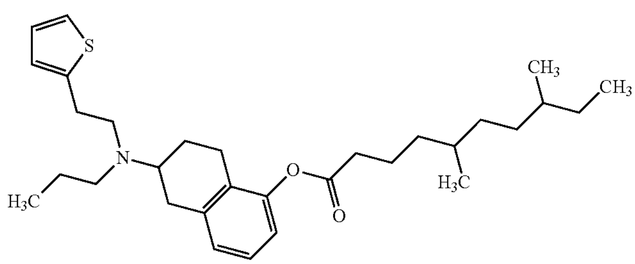 [SMILES: CCCN(CCc1cccs1)C1CCc2c(cccc2OC(=O)CCCC(C)CCC(C)CC)C1] | 9.10 ± 0.36 |
| A50 | Methyl Isolaurate (C13) | 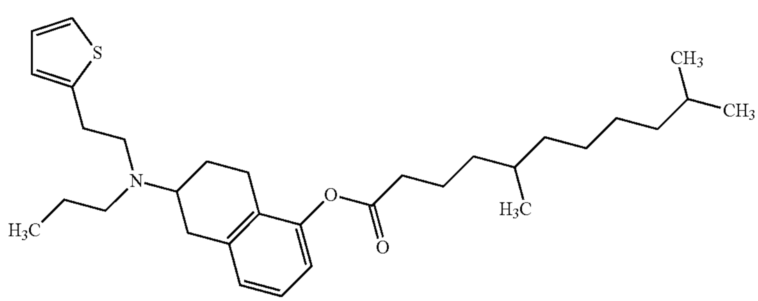 [SMILES: CCCN(CCc1cccs1)C1CCc2c(cccc2OC(=O)CCCC(C)CCCCC(C)C)C1] | 10.51 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
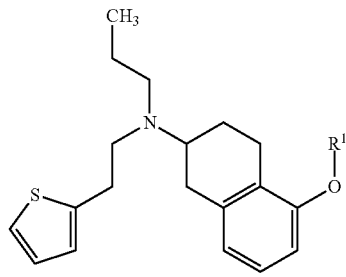
| Compound | R¹ | Structure | ClogP |
|---|---|---|---|
| A51 | Isotridecanoate (C13) | 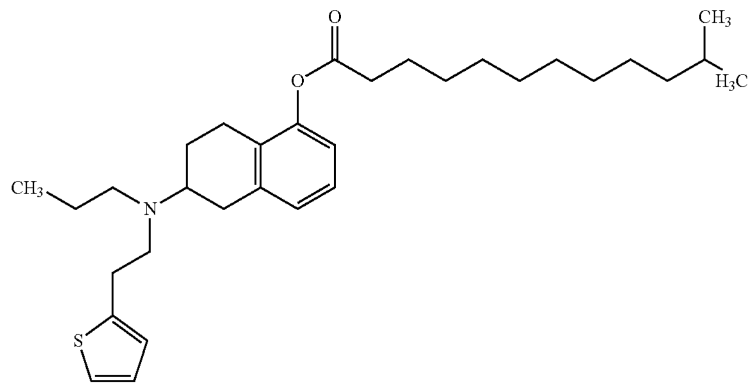 [SMILES: CCCN(CCc1cccs1)C1CCc2c(cccc2OC(=O)CCCCCCCCCC(C)C)C1] | 10.70 ± 0.36 |
| A52 | Propyl Caprate (C13) | 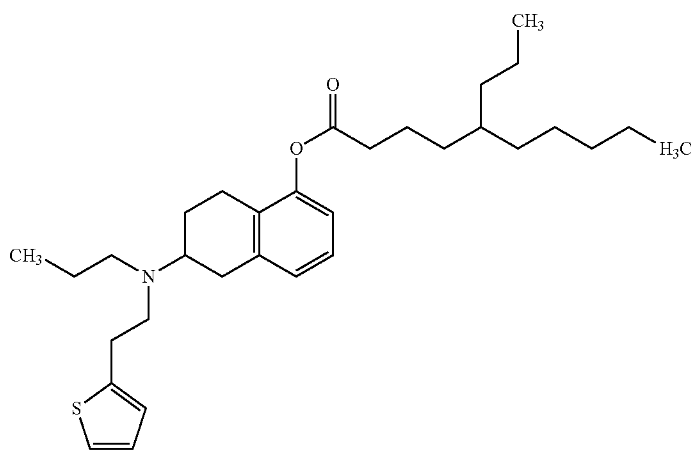 [SMILES: CCCCCC(CCC)CCCC(=O)Oc1cccc2c1CCC(N(CCC)CCc1cccs1)C2] | 10.70 ± 0.36 |
| A53 | Methyl, Ethyl Caprate (C13) | 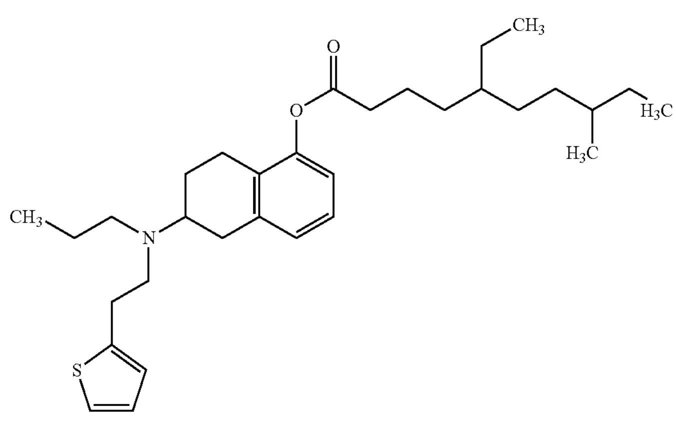 [SMILES: CCCN(CCc1cccs1)C1CCc2c(cccc2OC(=O)CCCC(CC)CCC(C)CC)C1] | 10.51 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
| Compound | $R^1$ | Structure | ClogP |
|---|---|---|---|
| A54 | Butyl Nanoate (C13) | 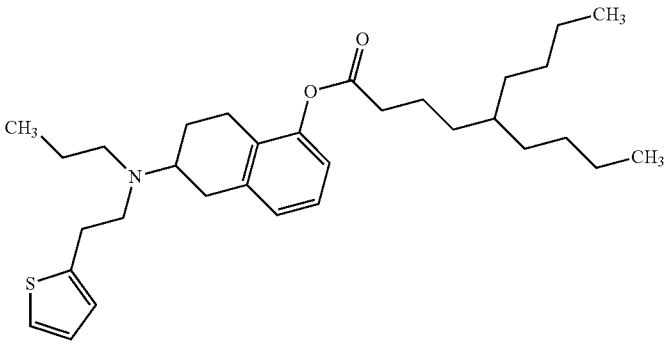 [SMILES: CCCCC(CCCC)CCCC(=O)Oc1cccc2c1CCC(N(CCC)CCc1cccs1)C2] | 10.70 ± 0.36 |
| A55 | Diethyl Nanoate (C13) | 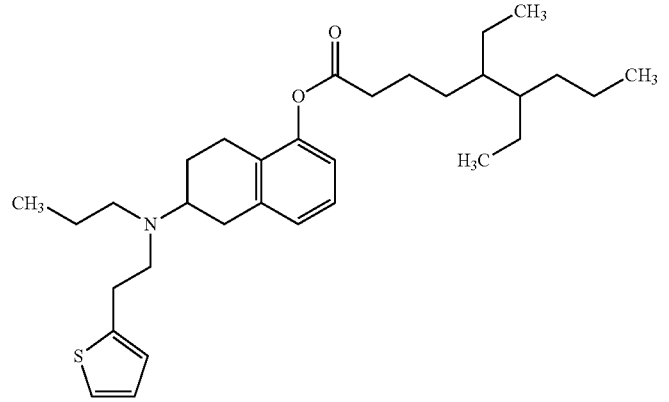 [SMILES: CCCC(CC)C(CC)CCCC(=O)Oc1cccc2c1CCC(N(CCC)CCc1cccs1)C2] | 10.51 ± 0.36 |
| A56 | Methyl, Propyl Nanoate (C13) | 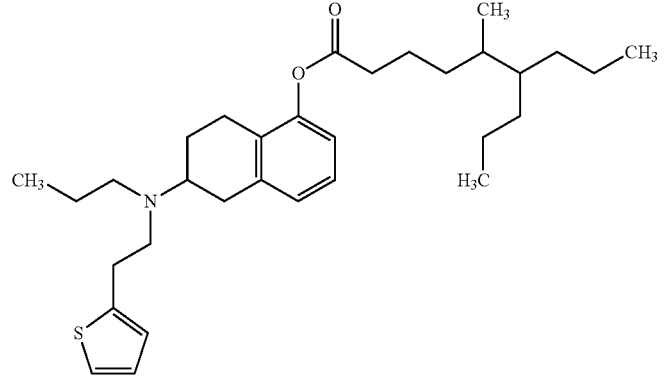 [SMILES: CCCC(CCC)C(C)CCCC(=O)Oc1cccc2c1CCC(N(CCC)CCc1cccs1)C2] | 10.51 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
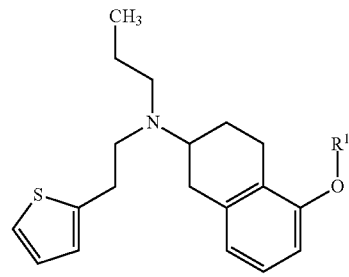
| Compound | R¹ | Structure | ClogP |
|---|---|---|---|
| A57 | Methyl Laurate (C13) | 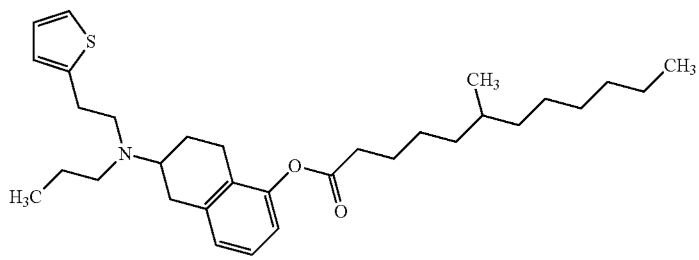 [SMILES: CCCCCCC(C)CCCCC(=O)Oc1cccc2c1CCC(N(CCC)CCc1cccs1)C2] | 10.70 ± 0.36 |
| A58 | Propyl Caprate (C13) | 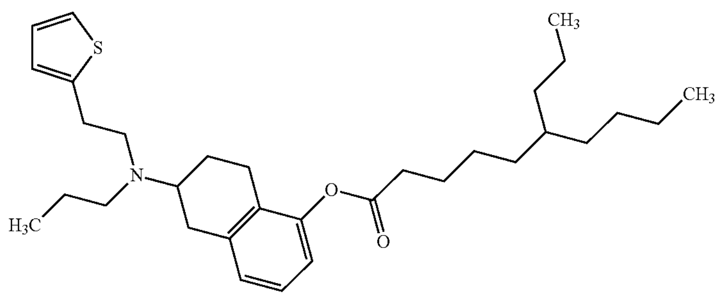 [SMILES: CCCCC(CCC)CCCCC(=O)Oc1cccc2c1CCC(N(CCC)CCc1cccs1)C2] | 10.70 ± 0.36 |
| A59 | Ethyl Propyl Caprylate (C13) | 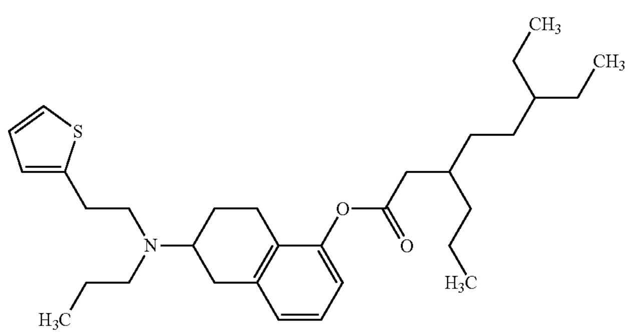 [SMILES: CCCC(CCC(CC)CC)CC(=O)Oc1cccc2c1CCC(N(CCC)CCc1cccs1)C2] | 10.70 ± 0.36 |
| A60 | Methyl, Butyl Caprylate (C13) | 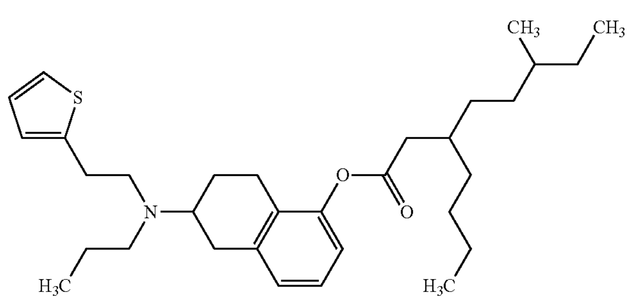 [SMILES: CCCCC(CCC(C)CC)CC(=O)Oc1cccc2c1CCC(N(CCC)CCc1cccs1)C2] | 10.51 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
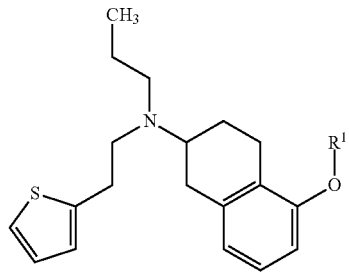
| Compound | R¹ | Structure | ClogP |
|---|---|---|---|
| A61 | Dipropyl caprylate (C14) | 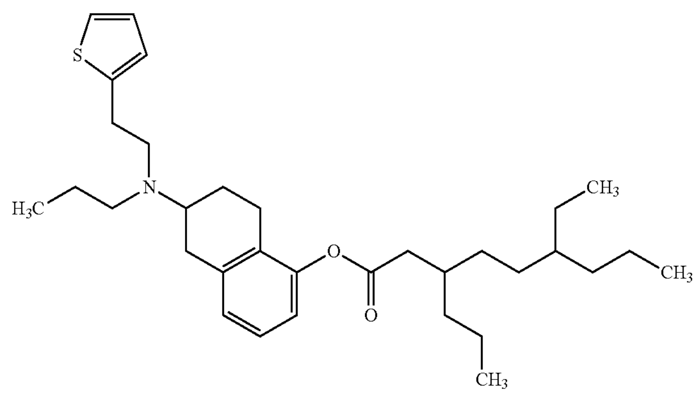 [SMILES: CCCC(CC)CCC(CCC)CC(=O)Oc1cccc2c1CCC(N(CCC)CCc1cccs1)C2] | 11.05 ± 0.36 |
| A62 | Heptyl Caproate (C13) | 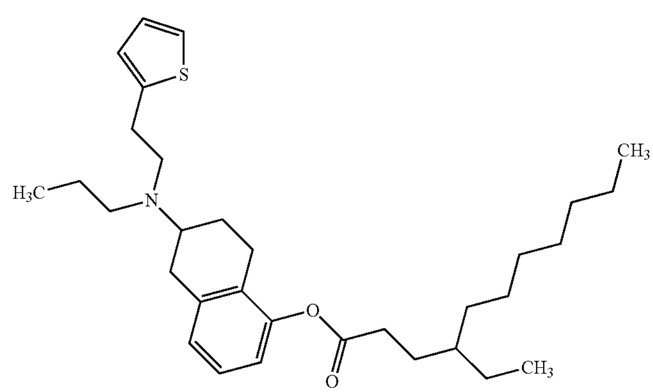 [SMILES: CCCCCCCC(CC)CCC(=O)Oc1cccc2c1CCC(N(CCC)CCc1cccs1)C2] | 10.70 ± 0.36 |
| A63 | Butyl, Propyl Enanthate (C13) | 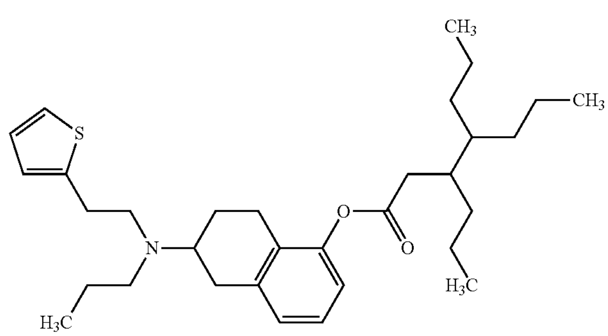 [SMILES: CCCC(CCC)C(CCC)CC(=O)Oc1cccc2c1CCC(N(CCC)CCc1cccs1)C2] | 10.51 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
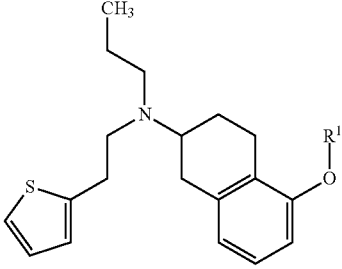
| Compound | R[1] | Structure | ClogP |
|---|---|---|---|
| A64 | Methyl Isolaurate (C13) | 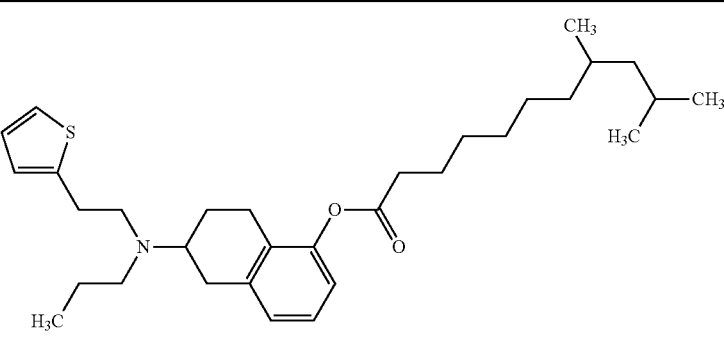 | 10.51 ± 0.36 |
| A65 | Isomyristate (C14) | 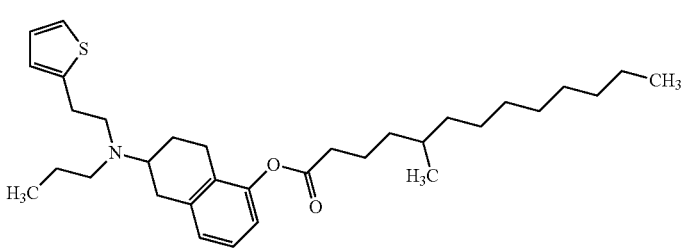 | 11.23 ± 0.36 |
| A66 | Methyl Tridecanoate (C14) | 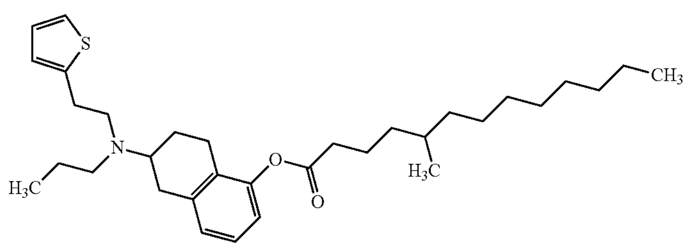 [SMILES: CCCCCCCCC(C)CCCC(=O)Oc1cccc2c1CCC(N(CCC)CCc1cccs1)C2] | 11.23 ± 0.36 |
| A67 | Dimethyl Isolaurate (C14) | 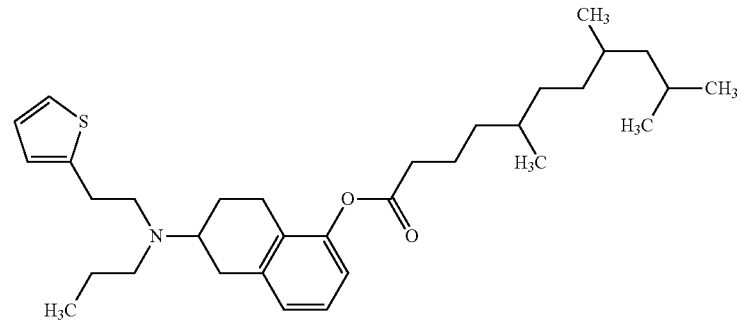 [SMILES: CCCN(CCc1cccs1)C1CCc2c(cccc2OC(=O)CCCC(C)CCC(C)CC(C)C)C1] | 10.86 ± 0.37 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
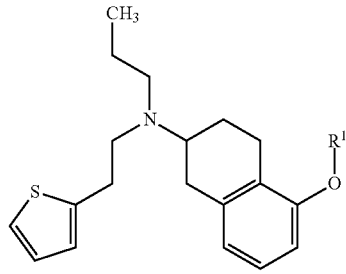
| Compound | R[1] | Structure | ClogP |
|---|---|---|---|
| A68 | Dimethyl Laurate (C14) | 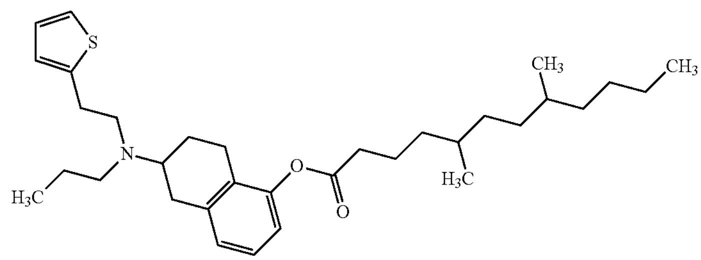 [SMILES: CCCCC(C)CCC(C)CCCC(=O)Oc1cccc2c1CCC(N(CCC)CCc1cccs1)C2] | 11.05 ± 0.36 |
| A69 | Ethyl Laurate (C14) | 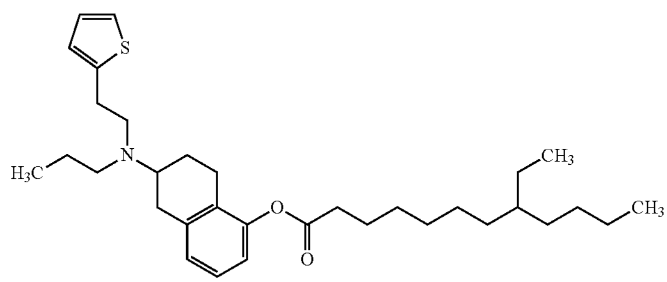 [SMILES: CCCCC(CC)CCCCCCC(=O)Oc1cccc2c1CCC(N(CCC)CCc1cccs1)C2] | 11.23 ± 0.36 |
| A70 | Propyl Undecanoate (C14) | 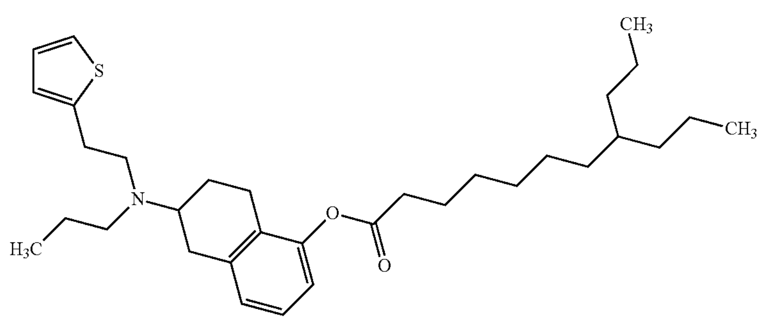 [SMILES: CCCC(CCC)CCCCCCC(=O)Oc1cccc2c1CCC(N(CCC)CCc1cccs1)C2] | 11.23 ± 0.36 |
| A71 | Trimethyl Undecanoate (C14) | 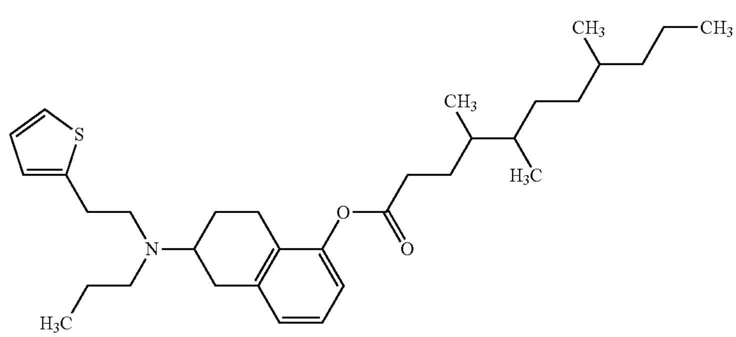 [SMILES: CCCC(C)CCC(C)C(C)CCC(=O)Oc1cccc2c1CCC(N(CCC)CCc1cccs1)C2] | 10.86 ± 0.37 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
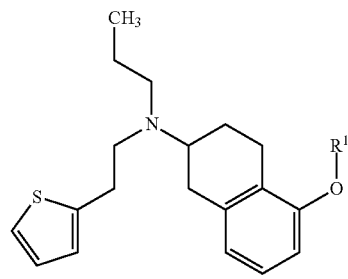
| Compound | R¹ | Structure | ClogP |
|---|---|---|---|
| A72 | Methyl, Ethyl Undecanoate (C14) | 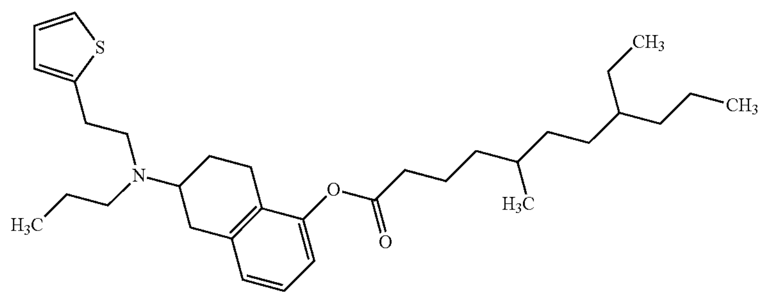 [SMILES: CCCC(CC)CCC(C)CCCC(=O)Oc1cccc2c1CCC(N(CCC)CCc1cccs1)C2] | 11.05 ± 0.36 |
| A73 | Butyl Caprate (C14) | 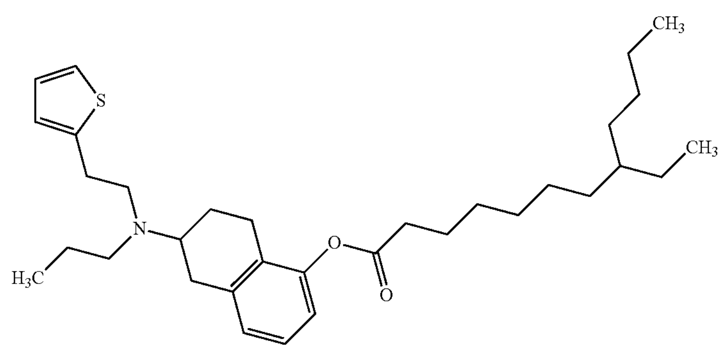 [SMILES: CCCCC(CC)CCCCCCC(=O)Oc1cccc2c1CCC(N(CCC)CCc1cccs1)C2] | 11.23 ± 0.36 |
| A74 | Diethyl Caprate (C14) | 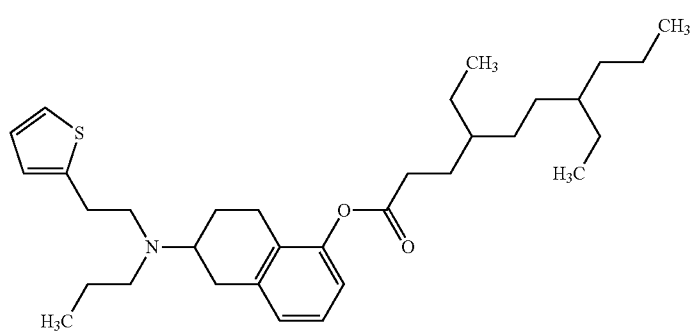 [SMILES: CCCC(CC)CCC(CC)CCC(=O)Oc1cccc2c1CCC(N(CCC)CCc1cccs1)C2] | 11.05 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
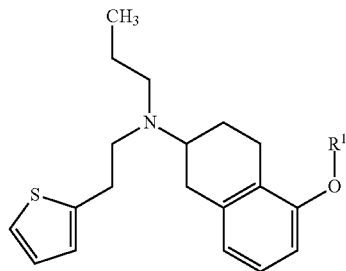
| Compound | R¹ | Structure | ClogP |
|---|---|---|---|
| A75 | Methyl Propyl Caprate (C14) | 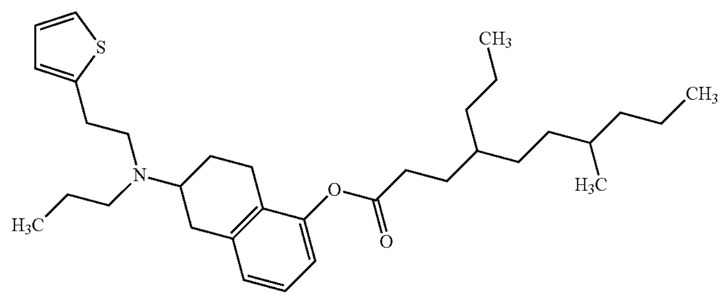 [SMILES: CCCC(C)CCC(CCC)CCC(=O)Oc1cccc2c1CCC(N(CCC)CCc1cccs1)C2] | 11.05 ± 0.36 |
| A76 | Tetramethyl Caprate (C14) | 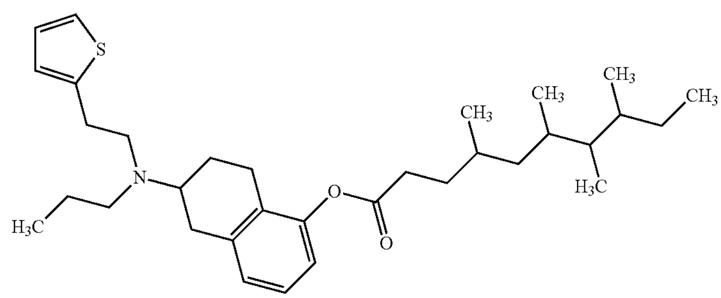 [SMILES: CCCN(CCc1cccs1)C1CCc2c(cccc2OC(=O)CCC(C)CC(C)C(C)C(C)CC)C1] | 10.68 ± 0.37 |
| A77 | Ethyl, Propyl Nanoate (C14) | 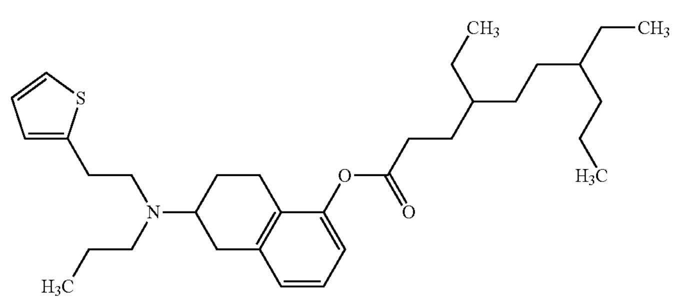 [SMILES: CCCC(CC)CCC(CC)CCC(=O)Oc1cccc2c1CCC(N(CCC)CCc1cccs1)C2] | 11.05 ± 0.36 |
| A78 | Methyl, Butyl Nanoate (C14) | 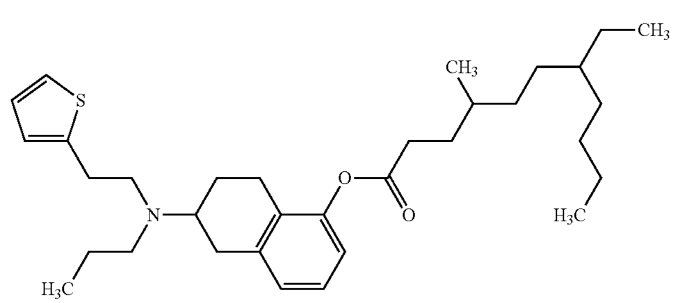 [SMILES: CCCCC(CC)CCC(C)CCC(=O)Oc1cccc2c1CCC(N(CCC)CCc1cccs1)C2] | 11.05 ± 0.36 |

APPENDIX A-continued

Rotigotine (A1) and Non-Limiting Examples of the Bioreversible Derivatives of Rotigotine (A2-A113) According to one Embodiment of the Disclosure, and their Corresponding Calculated logP (ClogP)

| Compound | R¹ | Structure | ClogP |
|---|---|---|---|
| A79 | Pentyl Nanoate (C14) | 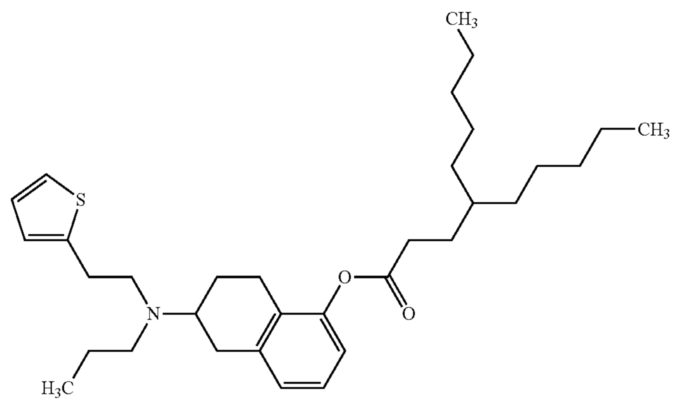 [SMILES: CCCCCC(CCCCC)CCC(=O)Oc1cccc2c1CCC(N(CCC)CCc1cccs1)C2] | 11.23 ± 0.36 |
| A80 | Dipropyl Caprylate (C14) | 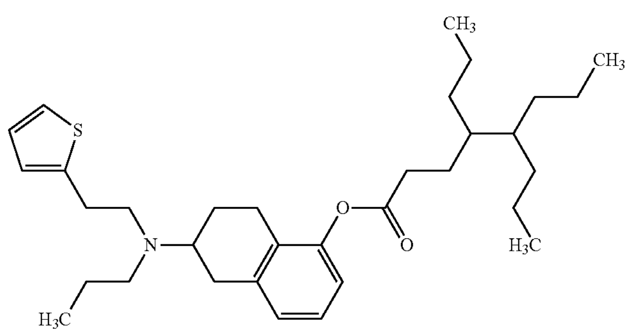 [SMILES: CCCC(CCC)C(CCC)CCC(=O)Oc1cccc2c1CCC(N(CCC)CCc1cccs1)C2] | 11.05 ± 0.36 |
| A81 | Dibutyl Caproate (C14) | 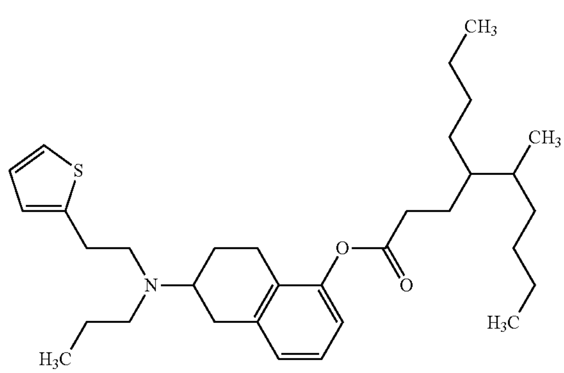 [SMILES: CCCCC(C)C(CCCC)CCC(=O)Oc1cccc2c1CCC(N(CCC)CCc1cccs1)C2] | 11.05 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
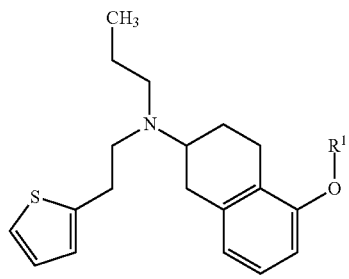
| Compound | R¹ | Structure | ClogP |
|---|---|---|---|
| A82 | Propyl, Butyl Enanthate (C14) | 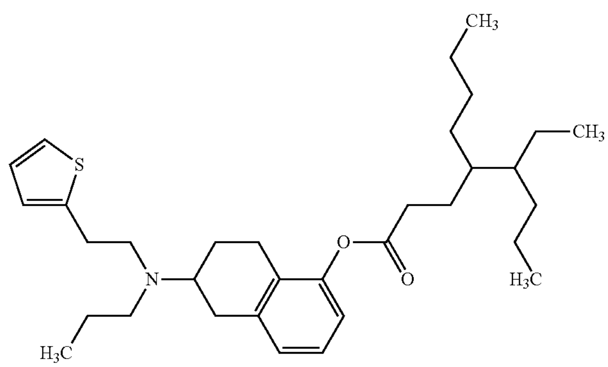 [SMILES: CCCCC(CCC(=O)Oc1cccc2c1CCC(N(CCC)CCc1cccs1)C2)C(CC)CCC] | 11.05 ± 0.36 |
| A83 | Methyl Myristate (C15) | 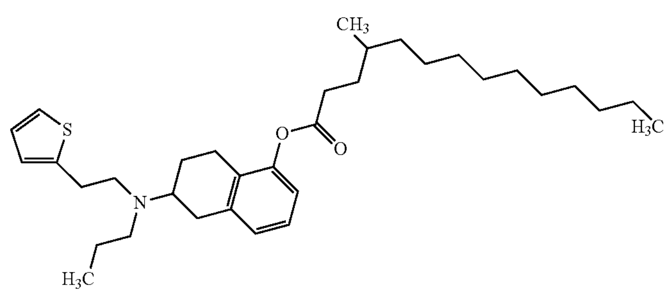 [SMILES: CCCCCCCCCCC(C)CCC(=O)Oc1cccc2c1CCC(N(CCC)CCc1cccs1)C2] | 11.76 ± 0.36 |
| A84 | Ethyl Myristate (C16) | 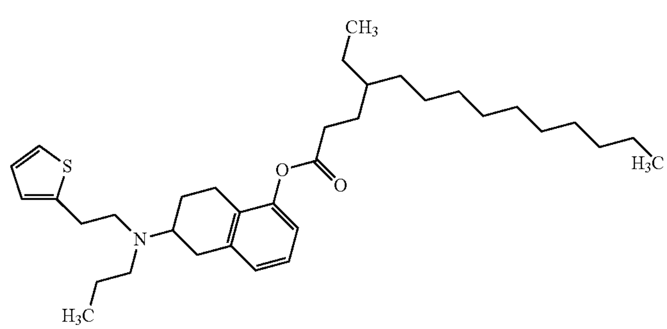 [SMILES: CCCCCCCCCCC(CC)CCC(=O)Oc1cccc2c1CCC(N(CCC)CCc1cccs1)C2] | 12.29 ± 0.36 |

APPENDIX A-continued

Rotigotine (A1) and Non-Limiting Examples of the Bioreversible Derivatives of Rotigotine (A2-A113) According to one Embodiment of the Disclosure, and their Corresponding Calculated logP (ClogP)

| Compound | R[1] | Structure | ClogP |
|---|---|---|---|
| A85 | Cyclohexanoate (C7) | 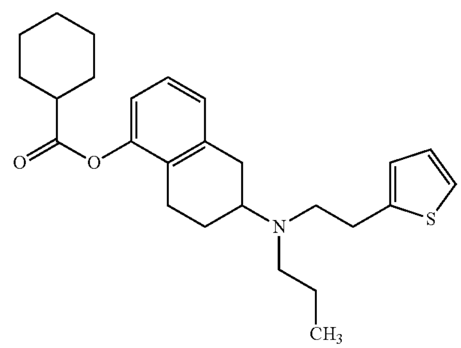 [SMILES: CCCN(CCc1cccs1)C1CCc2c(cccc2OC(=O)C2CCCCC2)C1] | 7.10 ± 0.36 |
| A86 | Cyclohexyl Pentanoate (C11) | 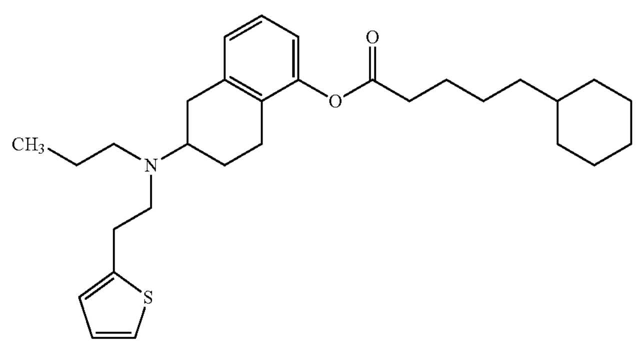 [SMILES: CCCN(CCc1cccs1)C1CCc2c(cccc2OC(=O)CCCCC2CCCCC2)C1] | 9.22 ± 0.36 |
| A87 | Cyclohexyl Heptanoate (C13) | 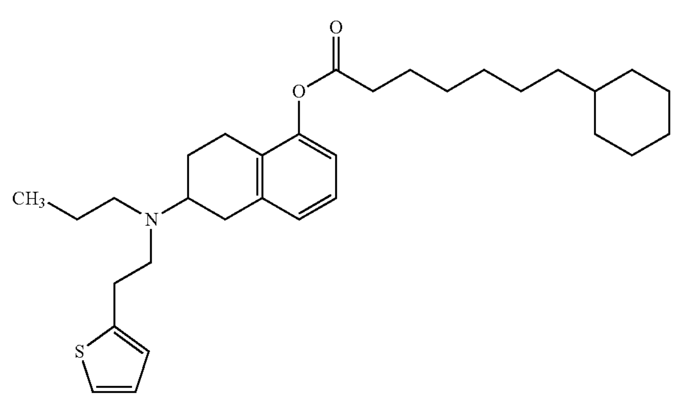 [SMILES: CCCN(CCc1cccs1)C1CCc2c(cccc2OC(=O)CCCCCCC2CCCCC2)C1] | 10.29 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
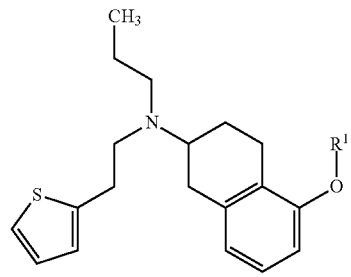
| Compound | R¹ | Structure | ClogP |
|---|---|---|---|
| A88 | 2,4,6-Trimethyl Cyclohexyl Propionate (C12) | 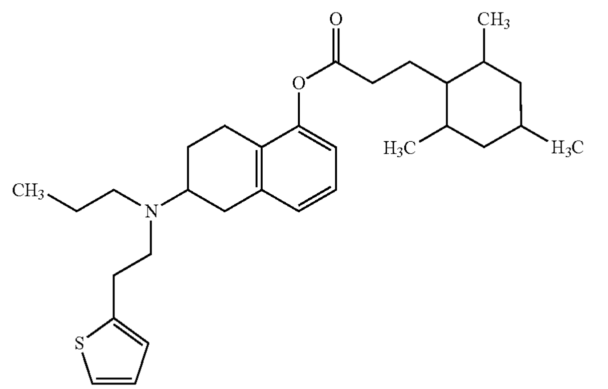 [SMILES: CCCN(CCc1cccs1)C1CCc2c(cccc2OC(=O)CCC2C(C)CC(C)CC2C)C1] | 9.64 ± 0.37 |
| A89 | 2,4,6-Triethyl Cyclohexyl Propionate (C15) | 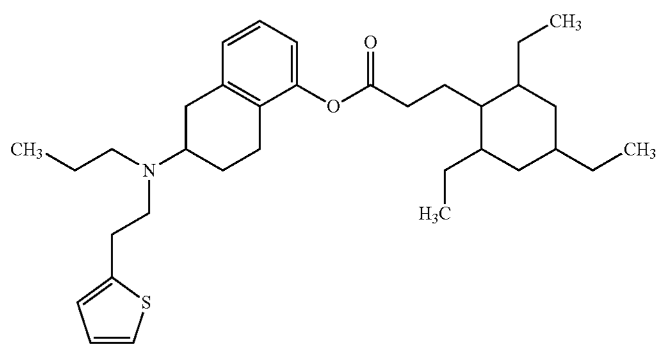 [SMILES: CCCN(CCc1cccs1)C1CCc2c(cccc2OC(=O)CCC2C(CC)CC(CC)CC2CC)C1] | 11.23 ± 0.37 |
| A90 | 2,4,6-Trimethyl Cyclohexanoate (C10) | 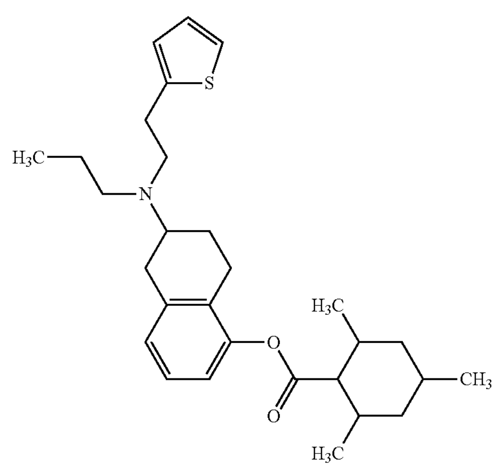 [SMILES: CCCN(CCc1cccs1)C1CCc2c(cccc2OC(=O)C2C(C)CC(C)CC2C)C1] | 8.57 ± 0.37 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
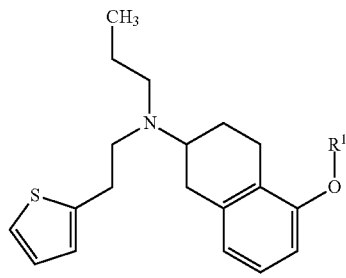
| Compound | R¹ | Structure | ClogP |
|---|---|---|---|
| A91 | 2,4,6-Triethyl Cyclohexanoate (C13) | | 10.17 ± 0.37 |
| A92 | 2,4,6-Tripropyl Cyclohexanoate (C16) | | 11.76 ± 0.37 |
| A93 | Mono-unsaturated Enanthate (C7) | | 7.37 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
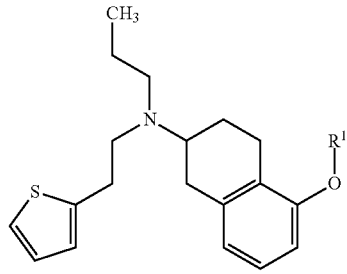
| Compound | R¹ | Structure | ClogP |
|---|---|---|---|
| A94 | Mono-unsaturated Decanoate (C10) | 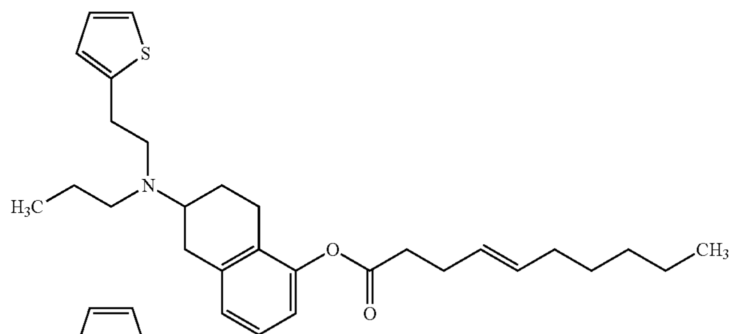 [SMILES: CCCCC/C=C/CCC(=O)Oc1cccc2c1CCC(N(CCC)CCc1cccs1)C2] | 8.96 ± 0.36 |
| A95 | Diunsaturated Decanoate (C10) | 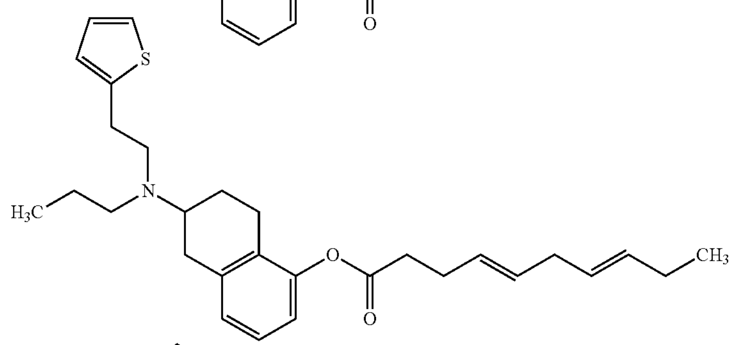 | 8.44 ± 0.42 |
| A96 | Myristoleate (C14) | 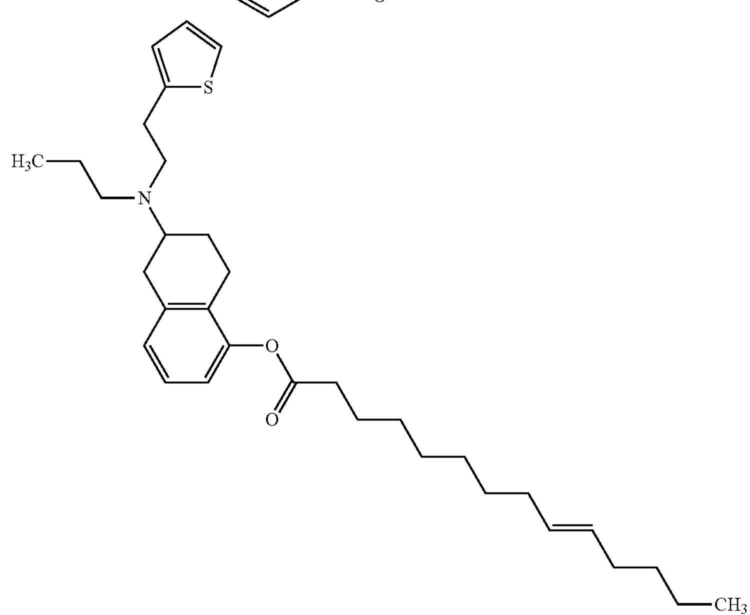 | 10.90 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
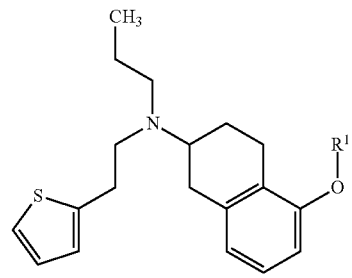
| Compound | R¹ | Structure | ClogP |
|---|---|---|---|
| A97 | Palmitolinoleate (C16) | 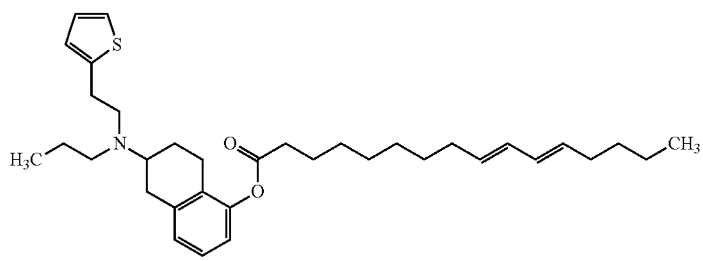 [SMILES: CCCC/C=C/C=C/CCCCCCCC(=O)Oc1cccc2c1CCC(N(CCC)CCc1cccs1)C2] | 11.44 ± 0.37 |
| A98 | Lauraoleate (C12) | 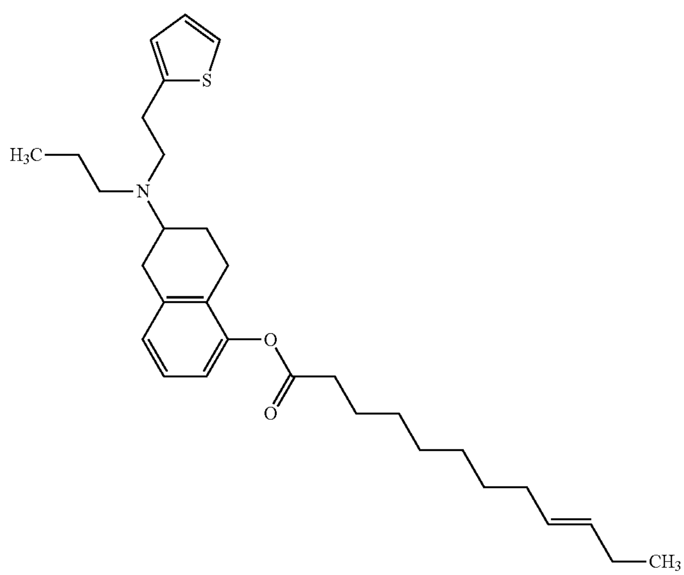 [SMILES: CC/C=C/CCCCCCCC(=O)Oc1cccc2c1CCC(N(CCC)CCc1cccs1)C2] | 9.83 ± 0.36 |
| A99 | Carbamate | 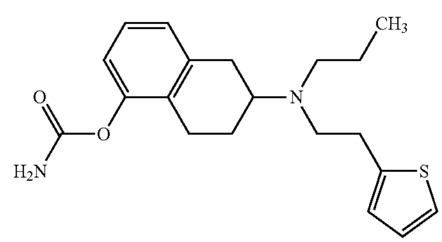 [SMILES: CCCN(CCc1cccs1)C1CCc2c(cccc2OC(N)=O)C1] | 4.56 ± 0.43 |

APPENDIX A-continued
Rotigotine (A1) and Non-Limiting Examples of the Bioreversible Derivatives of Rotigotine
(A2-A113) According to one Embodiment of the Disclosure, and their Corresponding
Calculated logP (ClogP)
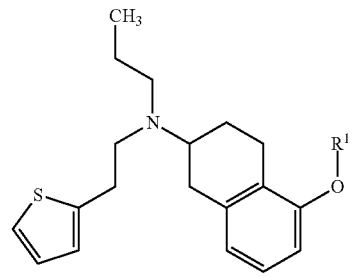
| Compound | R¹ | Structure | ClogP |
|---|---|---|---|
| A100 | Propyl Carbamate | 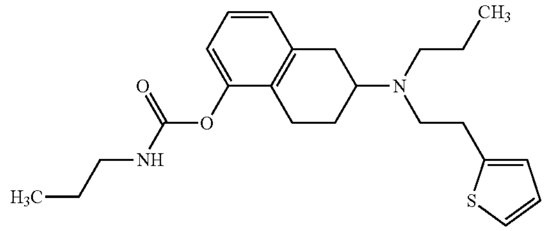 [SMILES: CCCNC(=O)Oc1cccc2c1CCC(N(CCC)CCc1cccs1)C2] | 5.71 ± 0.35 |
| A101 | Dipropyl Carbamate | 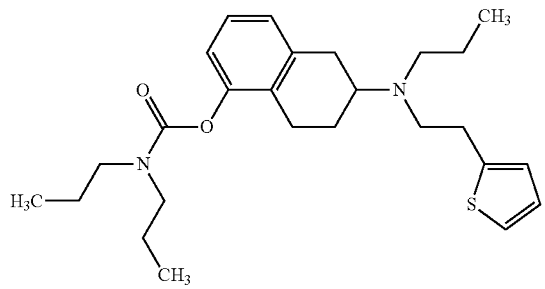 [SMILES: CCCN(CCC)C(=O)Oc1cccc2c1CCC(N(CCC)CCc1cccs1)C2] | 7.11 ± 0.36 |
| A102 | Dibutyl Carbamate | 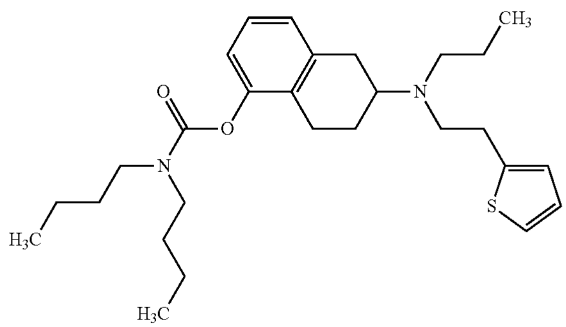 [SMILES: CCCCN(CCCC)C(=O)Oc1cccc2c1CCC(N(CCC)CCc1cccs1)C2] | 8.17 ± 0.36 |
| A103 | Dihexyl Carbamate | 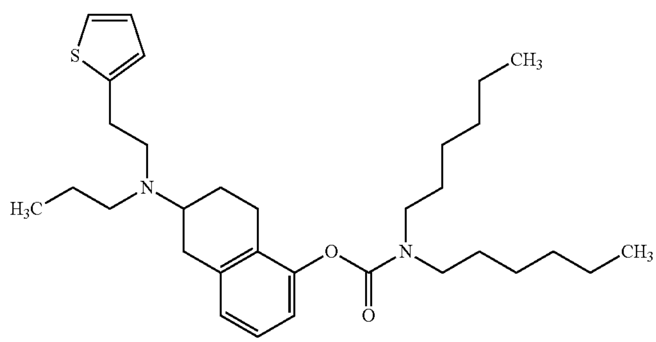 [SMILES: CCCCCCN(CCCCCC)C(=O)Oc1cccc2c1CCC(N(CCC)CCc1cccs1)C2] | 10.30 ± 0.36 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
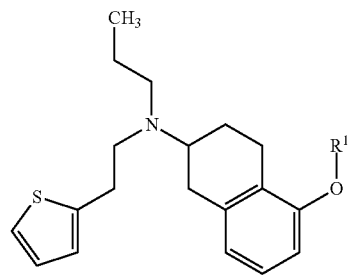
| Compound | R¹ | Structure | ClogP |
|---|---|---|---|
| A104 | Buciclate (C12) | 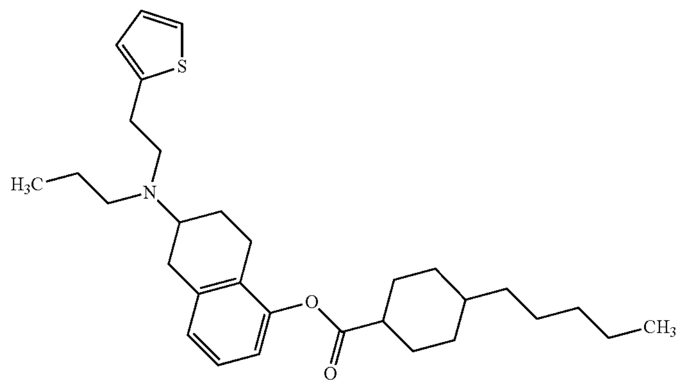 [SMILES: CCCCCC1CCC(C(=O)Oc2cccc3c2CCC(N(CCC)CCc2cccs2)C3)CC1] | 9.71 ± 0.36 |
| A105 | Cypionate (C9) | 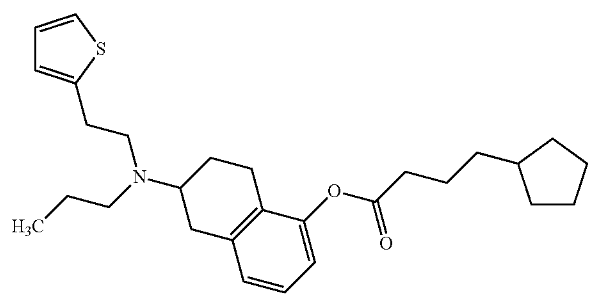 [SMILES: CCCN(CCc1cccs1)C1CCc2c(cccc2OC(=O)CCCC2CCCC2)C1] | 8.13 ± 0.36 |
| A106 | Benzoate (C7) | 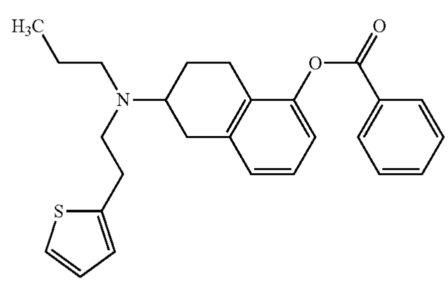 [SMILES: CCCN(CCc1cccs1)C1CCc2c(cccc2OC(=O)c2ccccc2)C1] | 7.07 ± 0.44 |
| A107 | 2-Methyl Benzoate (C8) | 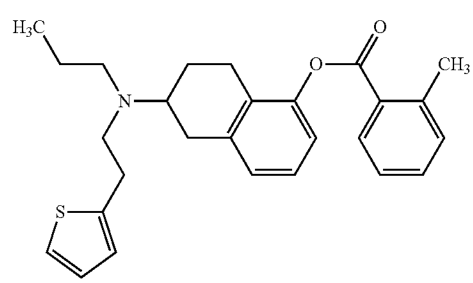 [SMILES: CCCN(CCc1cccs1)C1CCc2c(cccc2OC(=O)c2ccccc2C)C1] | 7.53 ± 0.45 |

APPENDIX A-continued

Rotigotine (A1) and Non-Limiting Examples of the Bioreversible Derivatives of Rotigotine (A2-A113) According to one Embodiment of the Disclosure, and their Corresponding Calculated logP (ClogP)

| Compound | R¹ | Structure | ClogP |
|---|---|---|---|
| A108 | 2-Dimethyl Benzoate (C9) | 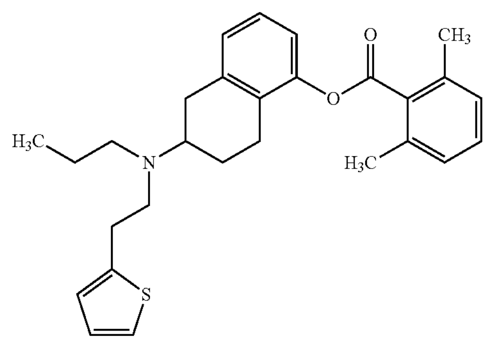 [SMILES: CCCN(CCc1cccs1)C1CCc2c(cccc2OC(=O)c2c(C)cccc2C)C1] | 7.99 ± 0.45 |
| A109 | 2,4,6-Trimethyl Benzoate (C10) | 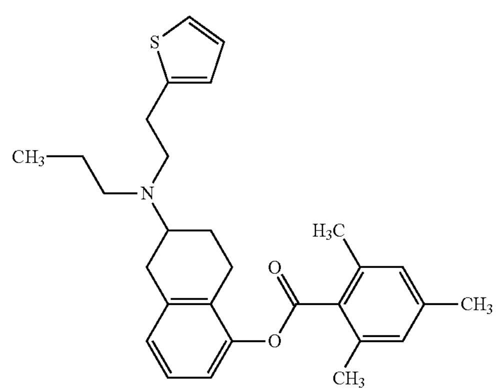 [SMILES: CCCN(CCc1cccs1)C1CCc2c(cccc2OC(=O)c2c(C)cc(C)cc2C)C1] | 8.45 ± 0.45 |
| A110 | 2-Amino Benzoate (Anthranilicate) | 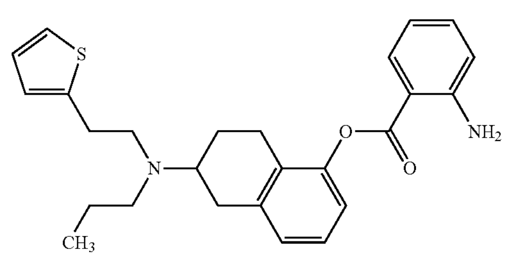 [SMILES: CCCN(CCc1cccs1)C1CCc2c(cccc2OC(=O)c2ccccc2N)C1] | 6.83 ± 0.49 |

APPENDIX A-continued
Rotigotine (A1) and Non-Limiting Examples of the Bioreversible Derivatives of Rotigotine (A2-A113) According to one Embodiment of the Disclosure, and their Corresponding Calculated logP (ClogP)
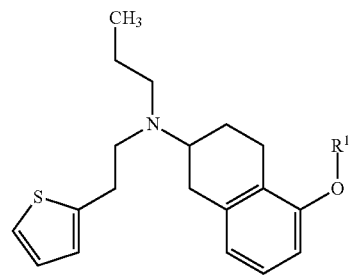
| Compound | R[1] | Structure | ClogP |
|---|---|---|---|
| A111 | Dipentyl Carbamate | | 9.23 ± 0.36 |
| A112 | 2-Methoxy Benzoate (C7) | | 6.80 ± 0.46 |
| A113 | 2-Butoxy Benzoate (C10) | | 8.40 ± 0.46 |

APPENDIX B
(S)-(-)-5-Hydroxy-N-propyl-2-aminotetralin (B1) and Non-Limiting Examples of the Bioreversible Derivatives (B2-B7)
According to one Embodiment of the Disclosure, and their Corresponding Calculated logP (ClogP)
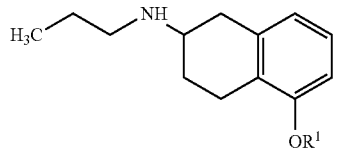
| Cpd. | $R^1$ | Structure | ClogP |
|---|---|---|---|
| B1 | H | 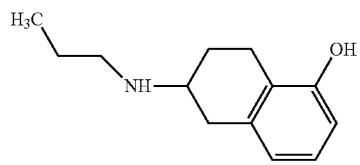 | 2.52 ± 0.29 |
| B2 | Laurate (C12) | 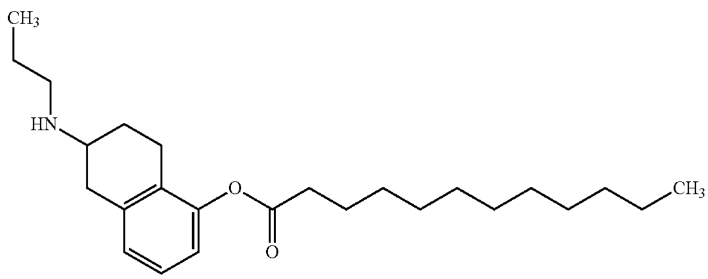 [SMILES: CCCCCCCCCCCC(=O)Oc1cccc2c1CCC(NCCC)C2] | 7.91 ± 0.30 |
| B3 | Tridecanoate (C13) | 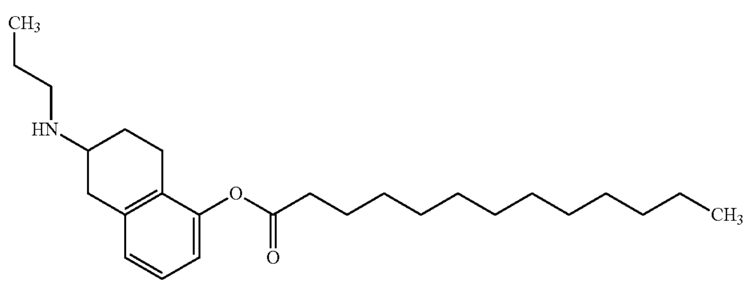 [SMILES: CCCCCCCCCCCCC(=O)Oc1cccc2c1CCC(NCCC)C2] | 8.45 ± 0.30 |
| B4 | Myristate (C14) | 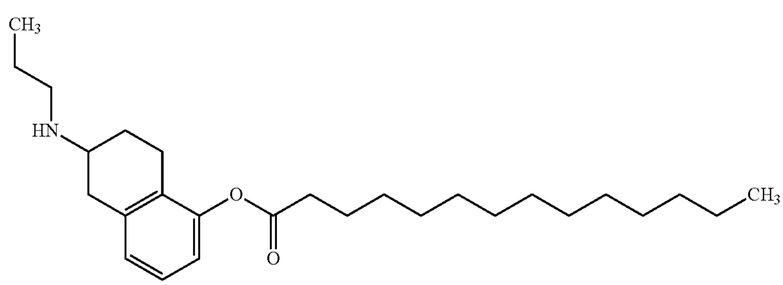 [SMILES: CCCCCCCCCCCCCC(=O)Oc1cccc2c1CCC(NCCC)C2] | 8.97 ± 0.30 |
| B5 | Palmitate (C16) | 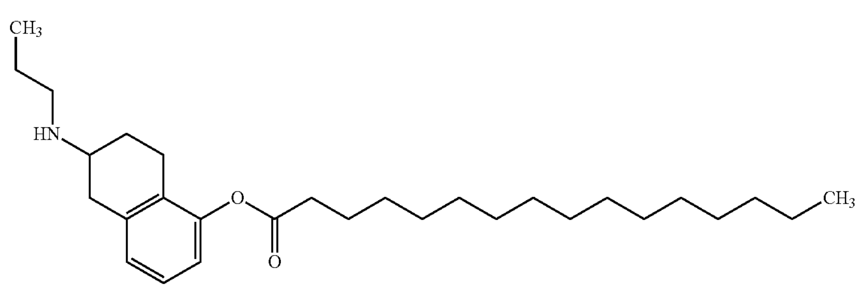 [SMILES: CCCCCCCCCCCCCCCC(=O)Oc1cccc2c1CCC(NCCC)C2] | 10.03 ± 0.30 |

APPENDIX B-continued (S)-(-)-5-Hydroxy-N-propyl-2-aminotetralin (B1) and Non-Limiting Examples of the Bioreversible Derivatives (B2-B7) According to one Embodiment of the Disclosure, and their Corresponding Calculated logP (ClogP)

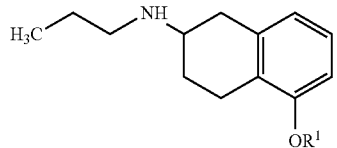

| Cpd. | R[1] | Structure | ClogP |
|---|---|---|---|
| B6 | Stearate (C18) | 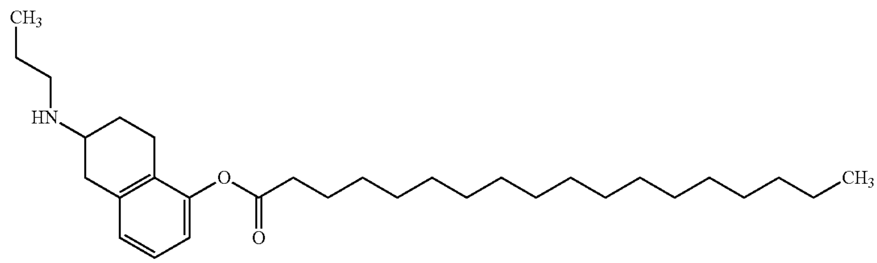 [SMILES: CCCCCCCCCCCCCCCCCC(=O)Oc1cccc2c1CCC(NCCC)C2] | 11.09 ± 0.30 |
| B7 | Oleate (C18) | 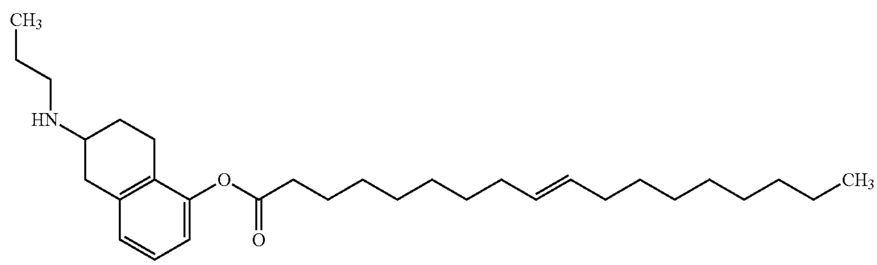 [SMILES: CCCCCCCC/C=C/CCCCCCCC(=O)Oc1cccc2c1CCC(NCCC)C2] | 10.58 ± 0.31 |

APPENDIX C

8-OH-DPAT (C1), 5-OH-DPAT (C2), 7-OH-DPAT (C3), and Bioreversible Derivatives C4-C10 of 8-OH-DPAT and the Calculated logP (ClogP) which is also applicable to 5-OH DPAT (C2) and 7-OH DPAT (C3).

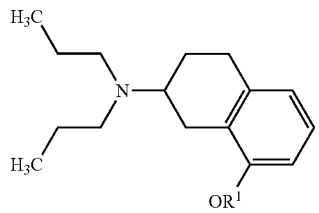

Bioreversible Derivatives C4-C10 of 8-OH-DPAT

| Example | Name | Structure | ClogP |
|---|---|---|---|
| C1 | 8-OH-DPAT | 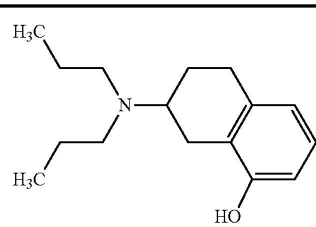 | 4.28 ± 0.25 |

APPENDIX C-continued
8-OH-DPAT (C1), 5-OH-DPAT (C2), 7-OH-DPAT (C3), and Bioreversible Derivatives C4-C10 of 8-OH-DPAT and the Calculated logP (ClogP) which is also applicable to 5-OH DPAT (C2) and 7-OH DPAT (C3).
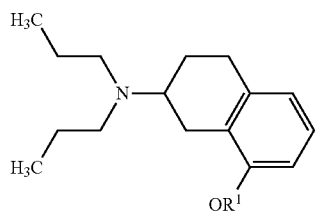
Bioreversible Derivatives C4-C10 of 8-OH-DPAT
| Example | Name | Structure | ClogP |
|---|---|---|---|
| C2 | 7-OH-DPAT | | 4.28 ± 0.25 |
| C3 | 5-OH-DPAT | | 4.28 ± 0.25 |
| C4 | Caprylate (C8) Ester of 8-OH-DPAT | | 7.54 ± 0.25 |
| C5 | Decanoate (C10) Ester of 8-OH-DPAT | | 8.60 ± 0.25 |
| C6 | Undecanoate (C11) Ester of 8-OH-DPAT | | 9.13 ± 0.25 |

APPENDIX C-continued
8-OH-DPAT (C1), 5-OH-DPAT (C2), 7-OH-DPAT (C3), and Bioreversible Derivatives C4-C10 of 8-OH-DPAT and the Calculated logP (ClogP) which is also applicable to 5-OH DPAT (C2) and 7-OH DPAT (C3).
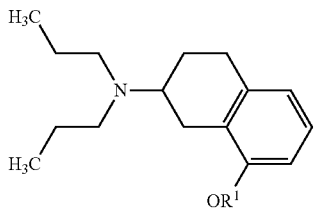
Bioreversible Derivatives C4-C10 of 8-OH-DPAT
| Example | Name | Structure | ClogP |
|---|---|---|---|
| C7 | Laurate (C12) Ester of 8-OH-DPAT | | 9.66 ± 0.25 |
| C8 | Tridecanoate (C13) Ester of 8-OH-DPAT | | 10.19 ± 0.25 |
| C9 | Myristate (C14) Ester of 8-OH-DPAT | | 10.72 ± 0.25 |

APPENDIX C-continued

8-OH-DPAT (C1), 5-OH-DPAT (C2), 7-OH-DPAT (C3), and Bioreversible Derivatives C4-C10 of 8-OH-DPAT and the Calculated logP (ClogP) which is also applicable to 5-OH DPAT (C2) and 7-OH DPAT (C3).

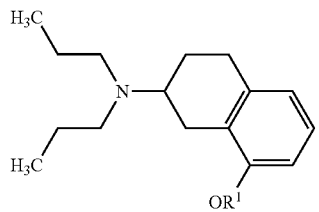

Bioreversible Derivatives C4-C10 of 8-OH-DPAT

| Example | Name | Structure | ClogP |
|---|---|---|---|
| C10 | Palmitate (C16) Ester of 8-OH-DPAT | 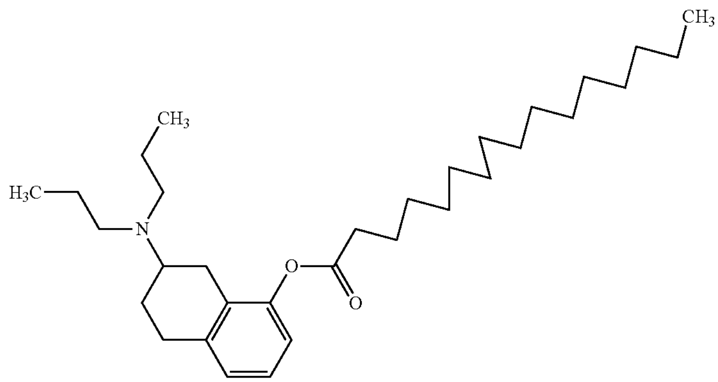 [SMILES: CCCCCCCCCCCCCCCC(=O)Oc1cccc2c1CC(N(CCC)CCC)CC2] | 11.79 ± 0.25 |
| C11 | Cypionate Ester of 8-OH-DPAT (C9) | 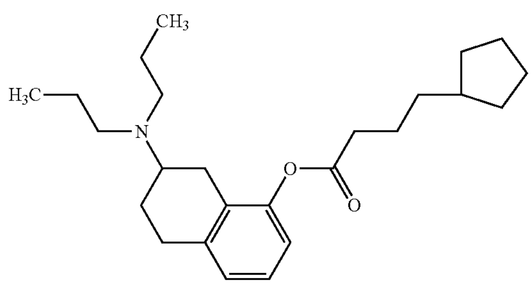 [SMILES: CCCN(CCC)C1CCc2cccc(OC(=O)CCCC3CCCC3)c2C1] | 7.44 ± 0.26 |
| C12 | Buciclate Ester of 8-OH-DPAT (C12) | 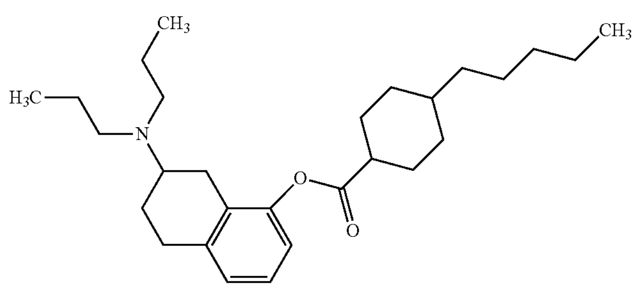 [SMILES: CCCCCC1CCC(C(=O)Oc2cccc3c2CC(N(CCC)CCC)CC3)CC1] | 9.03 ± 0.26 |
| C13 | Butyl Nanoate Ester of 8-OH-DPAT (C13) | 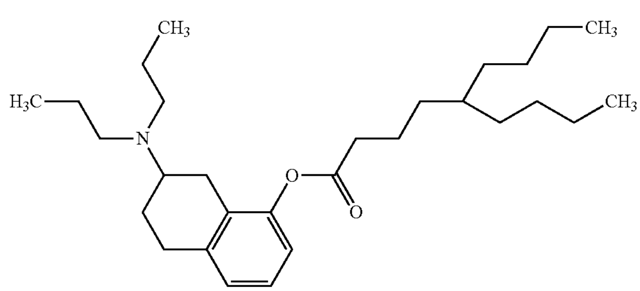 [SMILES: CCCCC(CCCC)CCCC(=O)Oc1cccc2c1CC(N(CCC)CCC)CC2] | 10.01 ± 0.26 |

The invention claimed is:
1. A composition comprising:
a bioreversible derivative of Formula I:

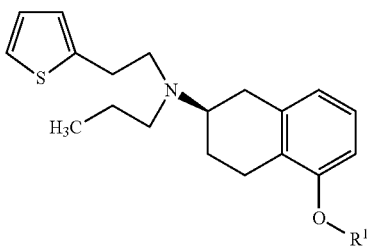

or an enantiomer or salt of said bioreversible derivative; and
a pharmaceutically acceptable carrier,
wherein $R^1$ is selected from the group consisting of butyl enanthate, methyl isocaprate, methyl caprate, isoundecanoate, diethyl enanthate, methyl propyl enanthate, ethyl propyl caproate, R-methyl undecanoate, dipropyl caproate, ethyl propyl enanthate, diethyl caprylate, propyl methyl caprylate, methyl isoundecanoate, isolaurate, dimethyl caprate, methyl isolaurate, isotridecanoate, methyl ethyl caprate, butyl nanoate ester, diethyl nanoate, methyl propyl nanoate, methyl laurate, ethyl propyl caprylate, methyl butyl caprylate, dipropyl caprylate, heptyl caproate, butyl propyl enanthate, methyl isolaurate, isomyristate, methyl tridecanoate, dimethyl isolaurate, dimethyl laurate, ethyl laurate, propyl undecanoate, trimethyl undecanoate, methyl ethyl undecanoate, butyl caprate, diethyl caprate, methyl propyl caprate, tetramethyl caprate, ethyl propyl nanoate, methyl butyl nanoate, pentyl nanoate, dipropyl caprylate, dibutyl caproate, propyl butyl enanthate, methyl myristate, ethyl myristate, cyclohexanoate, cyclohexyl pentanoate, cyclohexyl heptanoate, 2,4,6-trimethyl cyclohexyl propionate, 2,4,6-triethyl cyclohexyl propionate, 2,4,6-trimethyl cyclohexanoate, 2,4,6-triethyl cyclohexanoate, 2,4,6-tripropyl cyclohexanoate, mono-unsaturated enanthate, mono-unsaturated decanoate, diunsaturated decanoate, myristoleate, palmitolinoleate, lauraoleate, carbamate, dipropyl carbamate, dibutyl carbamate, dihexyl carbamate, benzoate, 2-methyl benzoate, 2-dimethyl benzoate, 2,4,6-trimethyl benzoate, 2-amino benzoate, dipentyl carbamate, 2-methoxy benzoate, 2-butoxy benzoate, propyl carbamate, tridecanoate, cypionate, buciclate, propyl caprate, undecanoate, laurate, myristate, and palmitate.

2. The composition of claim 1, wherein the bioreversible derivative has an intrinsic lipophilicity C log P value of about 7 to about 11.5.

3. The composition of claim 1, wherein the pharmaceutically acceptable carrier comprises at least one additive selected from the group consisting of lipophilic additives and hydrophilic additives.

4. The composition of claim 3, wherein the lipophilic additive includes a constituent selected from the group consisting of lipophilic surfactant(s), triglyceride(s), oil(s), fatty acid(s), fatty acid glyceride(s), tocopherol(s), tocopherol derivative(s), and mixtures comprising any thereof.

5. The composition of claim 1, wherein the pharmaceutically acceptable carrier comprises at least one constituent selected from the group consisting of hydrophilic triglyceride, hydrophilic surfactant(s), cellulose(s), polyvinyl pyrrolidone, polyvinyl acetate, polyvinyl alcohol, polyvinylpyrrolidone, vinylpyrrolidone-vinyl acetate copolymer, polyethylene glycol, and combinations comprising any thereof.

6. The composition of claim 1, further comprising at least one other active agent selected from the group consisting of an anticonvulsant, an opioid, a CGRP antagonist, a NMDA receptor blocker, a cannabinoid, a bradykinin antagonist, acetaminophen, dextromethorphan, a NSAID, a COX-2 selective inhibitor, a sedative, an antidepressant, a tranquilizer, a neuroprotective agent, an antipsychotic, an anxiolytic, an anti-migraine agent, and mixtures of any thereof.

7. The composition of claim 1, wherein the composition is orally bioavailable when administered to a human subject.

8. The composition of claim 1, wherein the bioreversible derivative has an apparent lipophilicity log $D_{7.4}$ value at pH 7.4 of about 4 to about 9.

9. The composition of claim 1, wherein
$R^1$ is selected from the group consisting of laurate, myristate, and the palmitate.

10. The composition of claim 1, wherein
$R^1$ is the undecanoate.

11. The composition of claim 1, wherein $R^1$ is selected from the group consisting of myristoleate, tridecanoate, cypionate, buciclate, lauraoleate, undecanoate, laurate, myristate, and benzoate.

12. The composition of claim 11, wherein $R^1$ is myristoleate.

13. The composition of claim 11, wherein $R^1$ is tridecanoate.

14. The composition of claim 11, wherein $R^1$ is cypionate.

15. The composition of claim 11, wherein $R^1$ is buciclate.

16. The composition of claim 11, wherein $R^1$ is lauraoleate.

17. The composition of claim 11, wherein $R^1$ is undecanoate.

18. The composition of claim 11, wherein $R^1$ is laurate.

19. The composition of claim 11, wherein $R^1$ is myristate.

20. The composition of claim 11, wherein $R^1$ is benzoate.

21. A method of treating a human subject for Parkinson's disease and/or restless leg syndrome, the method comprising:
orally administering to the human subject the composition of claim 1.

22. A method of treating a subject for Parkinson's disease and/or restless leg syndrome, the method comprising:
orally administering to the subject the composition of claim 1.

* * * * *

UNITED STATES PATENT AND TRADEMARK OFFICE
CERTIFICATE OF CORRECTION

PATENT NO. : 9,956,201 B2
APPLICATION NO. : 14/337037
DATED : May 1, 2018
INVENTOR(S) : William I. Higuchi and Firoozeh Aminian Patel It is certified that error appears in the above-identified patent and that said Letters Patent is hereby corrected as shown below:

In the Specification
Column 7, Line 9, change "or (6 S) - (–)-5-hy-" to --or (6S) - (–)-5-hy- --
Column 18, Line 10, change "rotigotine transdennal" to --rotigotine transdermal--
Column 25, Line 65, change "lethylamine, ethanol amine" to --lethylamine, ethanolamine--
Column 27, Line 54, change "dosage faint. the" to --dosage form, the--
Column 46, Line 18, change "cabergoline, carrnoxirole," to --cabergoline, carmoxirole,--

Signed and Sealed this
Fourteenth Day of August, 2018

Andrei Iancu
*Director of the United States Patent and Trademark Office*